(12) United States Patent
Yokota et al.

(10) Patent No.: US 11,851,654 B2
(45) Date of Patent: Dec. 26, 2023

(54) NUCLEIC ACID WITH REDUCED TOXICITY

(71) Applicant: NATIONAL UNIVERSITY CORPORATION TOKYO MEDICAL AND DENTAL UNIVERSITY, Tokyo (JP)

(72) Inventors: Takanori Yokota, Tokyo (JP); Tetsuya Nagata, Tokyo (JP); Kotaro Yoshioka, Tokyo (JP)

(73) Assignee: NATIONAL UNIVERSITY CORPORATION TOKYO MEDICAL AND DENTAL UNIVERSITY, Tokyo (JP)

( * ) Notice: Subject to any disclaimer, the term of this patent is extended or adjusted under 35 U.S.C. 154(b) by 36 days.

(21) Appl. No.: 16/982,274

(22) PCT Filed: Mar. 19, 2019

(86) PCT No.: PCT/JP2019/011464
§ 371 (c)(1),
(2) Date: Sep. 18, 2020

(87) PCT Pub. No.: WO2019/181946
PCT Pub. Date: Sep. 26, 2019

(65) Prior Publication Data
US 2021/0010000 A1 Jan. 14, 2021

(30) Foreign Application Priority Data
Mar. 19, 2018 (JP) .................. 2018-051338

(51) Int. Cl.
C07H 21/04 (2006.01)
C12N 15/113 (2010.01)
A61P 25/00 (2006.01)
A61K 9/00 (2006.01)

(52) U.S. Cl.
CPC .......... *C12N 15/113* (2013.01); *A61K 9/0085* (2013.01); *A61P 25/00* (2018.01); *C12N 2310/11* (2013.01)

(58) Field of Classification Search
None
See application file for complete search history.

(56) References Cited

U.S. PATENT DOCUMENTS

| 11,116,843 | B2 | 9/2021 | Seth et al. | |
| 2014/0302603 | A1 | 10/2014 | Yokota et al. | |
| 2016/0130583 | A1 | 5/2016 | Yokota et al. | |
| 2016/0287714 | A1 | 10/2016 | Kataoka et al. | |
| 2016/0355808 | A1* | 12/2016 | Khvorova | A61K 31/713 |
| 2018/0256729 | A1 | 9/2018 | Seth et al. | |
| 2019/0240352 | A1 | 8/2019 | Yokota et al. | |
| 2019/0247414 | A1* | 8/2019 | Yokota | C12N 15/09 |
| 2022/0023429 | A1 | 1/2022 | Seth et al. | |

FOREIGN PATENT DOCUMENTS

| CN | 1687101 A | 10/2005 |
| EP | 3521430 A1 | 8/2019 |
| JP | 2012521977 A | 9/2012 |
| JP | 2013049714 A | 3/2013 |
| JP | 2014534244 A | 12/2014 |
| JP | 2015-502134 A | 1/2015 |
| JP | 2016508367 A | 3/2016 |
| WO | 2007022470 A2 | 2/2007 |
| WO | 2010109212 A2 | 9/2010 |
| WO | 2010148249 A1 | 12/2010 |
| WO | 2011119852 A1 | 9/2011 |
| WO | 2011/123468 A1 | 10/2011 |
| WO | 2013075035 A1 | 5/2013 |
| WO | 2013089283 A1 | 6/2013 |
| WO | 2014118267 A1 | 8/2014 |
| WO | 2014132671 A1 | 9/2014 |
| WO | 2014192310 A1 | 12/2014 |
| WO | 2014203518 A1 | 12/2014 |
| WO | 2015/075942 A1 | 5/2015 |
| WO | 2015069906 A2 | 5/2015 |
| WO | 2015179525 A1 | 11/2015 |
| WO | 2016161374 A1 | 10/2016 |
| WO | 2018056442 A1 | 3/2018 |
| WO | 2018062510 A1 | 4/2018 |

OTHER PUBLICATIONS

Jain, K. "Intrathecal administration of drugs." MedLink Neurology. San Diego, CA: MedLink Corporation. Medlink website. Available at http://www. medlink. com. Accessed May 31, 2008.*
Barclay, Jane, et al. "Functional downregulation of P2X3 receptor subunit in rat sensory neurons reveals a significant role in chronic neuropathic and inflammatory pain." Journal of neuroscience 22.18 (2002): 8139-8147.*
Dorn, Gabriele, et al. "siRNA relieves chronic neuropathic pain." Nucleic acids research 32.5 (2004): e49-e49.*
Yokota, Takanori. "DNA/RNA heteroduplex oligonucleotide for highly efficient gene silencing." Clinical and Experimental Neuroimmunology 7.2 (2016): 108-109.*
Nishina, Kazutaka, et al. "DNA/RNA heteroduplex oligonucleotide for highly efficient gene silencing." Nature communications 6.1 (2015): 7969 p. 2).*
Nishina et al., "DNA/RNA heteroduplex oligonucleotide for highly efficient gene silencing", Nature Communications, 2015, vol. 6, No. 7969, pp. 1-13.

(Continued)

*Primary Examiner* — Kimberly Chong
(74) *Attorney, Agent, or Firm* — Lucas & Mercanti, LLP

(57) ABSTRACT

An object of the invention is to provide a low toxicity antisense nucleic acid medicine that can modulate expression of a target transcriptional product in the central nervous system and other sites of a subject. Provided is a low toxicity composition for modulating expression of a target transcriptional product in a site such as the central nervous system of a subject, having a nucleic acid complex formed by annealing together a first nucleic acid strand having an antisense oligonucleotide region with respect to the target transcriptional product, and a second nucleic acid strand having a complementary region that is complementary to at least part of the first nucleic acid strand.

15 Claims, 15 Drawing Sheets
Specification includes a Sequence Listing.

(56) References Cited

OTHER PUBLICATIONS

Asami et al., "Drug delivery system of therapeutic oligonucleotides", Drug Discoveries & Therapeutics, 2016, vol. 10, No. 5, pp. 256-262.
Ohyagi et al., "Oligonucleotide therapeutics for treatment of neurological degenerative diseases", Seitai no Kagaku, 2016, vol. 67, No. 4, pp. 349-353, Partial English translation 2 pages.
Kuwahara et al., "Modulation of blood-brain barrier function by a heteroduplex oligonucleotide in vivo", Scientifc Reports, 2018, vol. 8, No. 4377, pp. 1-25.
Kunieda et al., "Novel double-stranded nucleic acid medicine: overhung double-stranded nucleic acid", Lecture abstracts of the 2nd annual conference of Nucleic Acids Therapeutics Society of Japan, 2016, pp. 1-3.
International Search Report for Corresponding International Application No. PCT/JP2019/011464 (dated Jun. 11, 2019) (2 Pages).
Modarresi et al., "Knockdown of BACE1-AS Nonprotein-Coding Transcript Modulates Beta-Amyloid-Related Hippocampal Neurogenesis", International Journal of Alzheimer's Disease, 2011, vol. 2011, pp. 1-11.
Wang et al.,"Therapeutic Gene Silencing Delivered by a Chemically Modified Small Interfering RNA against Mutant SOD1 Slows Amyotrophic Lateral Sclerosis Progression", The Journal of Biological Chemistry, 2008, vol. 283, No. 23, pp. 15845-15852.
Supplementary European Search Report for Corresponding European Application No. 19770584.1, 12 pages, dated Apr. 4, 2022.
Uno, Y. et al., Efficient In vivo delivery of siRNA to the Brain by Conjugation of alpha-Tocopherol, 32th The Annual Meeting of the Molecular Biology Society of Japan: abstracts, 2009, p. 248, IP-0816, entire text.
Uno, Y. et al., Efficient In vivo delivery of siRNA to the Brain by Conjugation of alpha-Tocopherol, Molecular Therapy, 2009, vol. 17, Supplement 1, p. S197, 515, entire text.
Nishina, K. et al., Novel oligonucleotide based on DNA/RNA heteroduplex structures, 57th Annual Meeting of the Japanese Society of Neurology: abstracts, May 2016, p. 194, entire text, non-official translation.
Julia F. Alterman, et al., "Hydrophobically Modified Sirnas Silence Huntingtin . . . ", Molecular Therapy-Nucleic Acids, vol. 4, No. 12, pp. e266, 2015.
Yoshitaka Uno, et al., "High-Density Lipoprote Facilitates in Vivo Delivery . . . ", Human Gene Therapy, vol. 22, No. 6, pp. 711-719, 2011.
Kazutaka Nishina, et al., "DNA/RNA Heteroduplex Oligonucleotide for Highly Efficient Gene Silencing", Nature Communications, vol. 6, No. 7969, pp. 1-13, 2015.
Supplemental European Search Report corresponding to European Application No. 17853209.9 dated Apr. 28, 2020 (5 pages).
"TTR transthyretin [*Homo sapiens* (human)]-Gene-NCBI", https://www.ncbi.nlm.nih.gov/gene/7276#gene-expression, pp. 1-9. [Gene ID: 7276, updated on Nov. 28, 2021].
"Brain tissue expression of TTR-Summary—The Human Protein Atlas", https://www.proteinatlas.org/ENSG00000118271-TTR/brain, pp. 1-3.
Jan Krutzfeldt et al., "Silencing of microRNAs in vivo with 'antagomirs'", Nature, vol. 438, pp. 685-689, 2005. [Letters].
Pardridge, "Transport of small molecules through the blood-brain barrier: biology and methodology", Advanced Drug Delivery Reviews, 1995, vol. 15, pp. 5-36.
Siomi et al., "On the road to reading the RNA-interference code", Nature, 2009, vol. 457, pp. 396-404.
Ono et al., "Separation-related rapid nuclear transport of DNA/RNA heteroduplex oligonucleotide: unveiling distinctive intracellular trafficking", Molecular Therapy: Nucleic Acids, 2020, vol. 23, pp. 1360-1370.
Yokota et al "Gene Therapy with therapeutic oligonucleotides", Department of Neurology and Neurological Science, Graduate School, Tokyo Medical and Dental University, 2016, vol. 33, Issue 3, pp. 303-306, Partial English Translation 1 Page.

\* cited by examiner

Fig. 1
(a)
First nucleic acid strand
Second nucleic acid strand
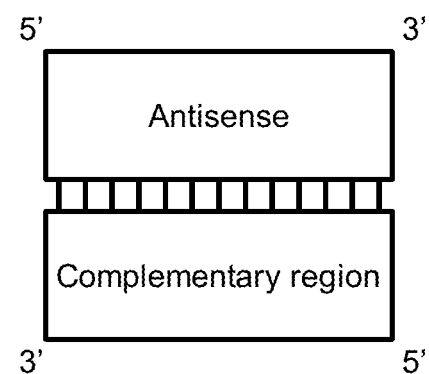
(b)
First nucleic acid strand
Second nucleic acid strand
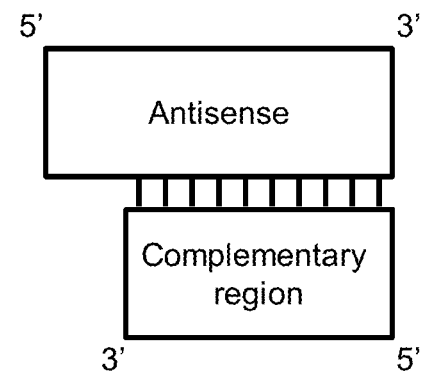

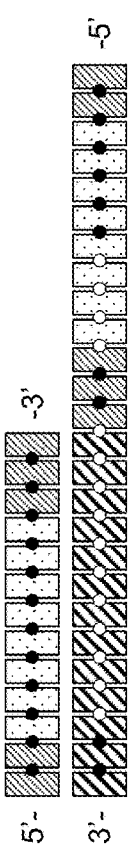
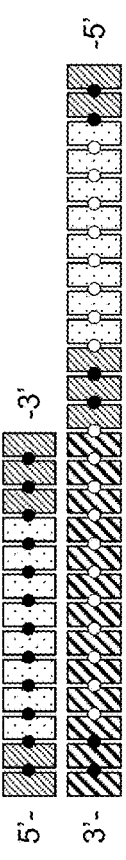
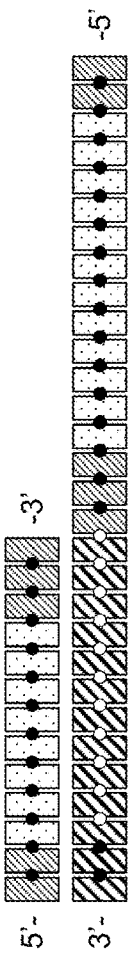
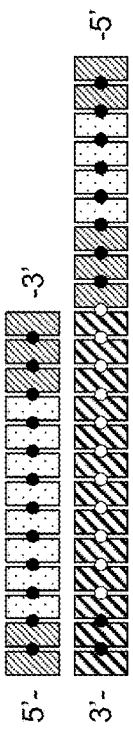
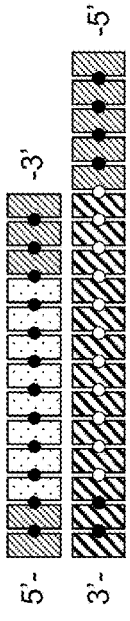
Fig. 10

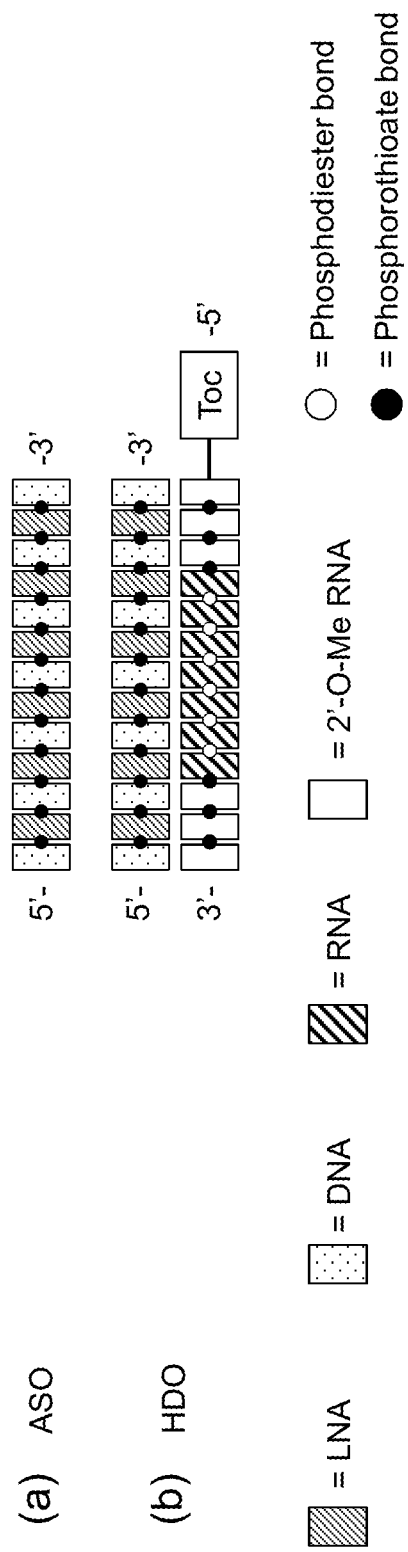

SEQUENCE LISTING

<160> NUMBER OF SEQ ID NOS: 33

<210> SEQ ID NO 1
<211> LENGTH: 4178
<212> TYPE: DNA
<213> ORGANISM: Mus musculus

<400> SEQUENCE: 1

```
ggaaaagcaa aaaccctttg gctttgacag ccaccgccac aagcctttcc gcctccccag      60
cctgcctagg tgctgggagc tgggagctgg attatggtgg cctgagcagc cgacgcagcc     120
gtaggagccc ggagtccctg tcggtcccca agctgcaaag cccgcctgga agaccccgaa     180
agctacgggc tcggatagcc atgcccgccc ctcccagccc cacaagggc ccgatccccc      240 cgctggcggc cggcgtccag atgtagctgg gtccctgga tcgccatcgt cgtctcctct      300
cgtgcgctac ggatttctcc tgcccactct ccgccgcctg gaccgggaac tgagcgaggg     360
gcctgcagac tctgcagtcc tgatgccgcc gaggccgctc tcctgagaga agccaccacc     420
acccagactt aggggcaggc aagagggaca gtcaccaacc ggaccacaag gcccgggctc     480
actatggccc cagcgctgca ctggctcctg ctatgggtgg gctcgggaat gctgcctgcc     540
cagggaaccc atctcggcat ccggctgccc cttcgcagcg gcctggcagg gccacccctg     600
ggcctgaggc tgccccggga gaccgacgag gaatcggagg agcctggccg gagaggcagc     660
tttgtggaga tggtggacaa cctgagggga aagtccggcc agggctacta tgtggagatg     720
accgtaggca gccccccaca gacgctcaac atcctggtgg acacgggcag tagtaacttt     780
gcagtggggg ctgccccaca cccttttcctg catcgctact accagaggca gctgtccagc     840
```

```
acatatcgag acctccgaaa gggtgtgtat gtgccctaca cccagggcaa gtgggagggg      900
gaactgggca ccgacctggt gagcatccct catggcccca acgtcactgt gcgtgccaac      960
attgctgcca tcactgaatc ggacaagttc ttcatcaatg gttccaactg ggagggcatc     1020
ctagggctgg cctatgctga gattgccagg cccgacgact cttggagcc cttctttgac      1080 tccctggtga agcagaccca cattcccaac atcttttccc tgcagctctg tggcgctggc     1140
ttccccctca accagaccga ggcactggcc tcggtgggag ggagcatgat cattggtggt     1200
atcgaccact cgctatacac gggcagtctc tggtacacac ccatccggcg ggagtggtat     1260
tatgaagtga tcattgtacg tgtggaaatc aatggtcaag atctcaagat ggactgcaag     1320
gagtacaact acgacaagag cattgtggac agtgggacca ccaaccttcg cttgcccaag     1380
aaagtatttg aagctgccgt caagtccatc aaggcagcct cctcgacgga gaagttcccg     1440
gatggctttt ggctagggga gcagctggtg tgctggcaag caggcacgac cccttggaac     1500
atttccccag tcatttcact ttacctcatg ggtgaagtca ccaatcagtc cttccgcatc     1560
accatccttc ctcagcaata cctacggccg gtggaggacg tggccacgtc ccaagacgac     1620
tgttacaagt tcgctgtctc acagtcatcc acgggcactg ttatgggagc cgtcatcatg     1680
gaaggtttct atgtcgtctt cgatcgagcc cgaaagcgaa ttggctttgc tgtcagcgct     1740
tgccatgtgc acgatgagtt caggacgcg gcagtggaag gtccgtttgt tacggcagac      1800
atggaagact gtggctacaa cattccccag acagatgagt caacacttat gaccatagcc     1860
tatgtcatgg cggccatctg cgccctcttc atgttgccac tctgcctcat ggtatgtcag     1920
tggcgctgcc tgcgttgcct cgccaccag cacgatgact ttgctgatga catctccctg      1980
ctcaagtaag gaggcccgtg ggcagatgat ggagacgccc ctggaccaca tctgggtggt     2040 tcccttggt cacatgagtt ggagctatgg atggtacctg tggccagagc acctcaggac      2100
cctcaccaac ctgccaatgc ttctggcgtg acagaacaga gaaatcaggc aagctggatt     2160
acagggcttg cacctgtagg acacaggaga gggaaggaag cagcgttctg gtggcaggaa     2220
tatccttaga caccacaaac ttgagttgga aattttgctg cttgaagctt cagccctgac     2280
cctctgccca gcatccttta gagtctccaa cctaaagtat tctttatgtc cttcagaag     2340 tactggcgtc atactcaggc tacccggcat gtgtccctgt ggtaccctgg cagagaaagg     2400
gccaatctca ttccctgctg gccaaagtca gcagaagaaa gtgaagtttg ccagttgctt     2460
tagtgatagg gactgcagac tcaagcctac actggtacaa agactgcgtc ttgagataaa     2520
caagaaccta tgcgatgcga atgtttatac tcctgggggc agtcaagatg aggagacagg     2580
ataggataga gacaggaagg agatggtagc aaaactggga aaggcagaac tctgatcact     2640
ttctagttcc aagtttagac tcatctccaa gacagaagcc catctggact aagaggtatc     2700
attccccaat gtgcctgtgg ttgtagtctg aactgaaatg aaatggggga aaagggctt      2760 attagccaaa gagctctttt taacactctt agagaacag tgctcatgag aaaagtccca      2820
ctggacagat gaattcctat cttgttaatt ctgtctctct ctgcttcttc aacatgctaa     2880
gtggcaccaa aatgacccaa ccccaaggtc ttaggtgccc tatgggacaa cagttagaat     2940
attgtagggc tagggatggt cttcccagca taggttcact ccaaccaagg tgctaaaagg     3000
aacagacagg agagtcctcc tctctgatcc acaaaggcag agccctcaag attcatccag     3060
cagggttagg gctgatgcat ttgcctctgc ctggattttg tttttatttt ctttcttttt     3120
gcccagtggt acaaaacgat aagctcttta tggaatactg agtgggttca ttcctctctt     3180
```

| | |
|---|---|
| gccctctcca atggcccctc tatttatctg gctaaggaaa caccacgcat tggctagtat | 3240 |
| taaacagcaa ctgtaagata gagggctttc tgttctatgt cattgccttc agtatcaagg | 3300 |
| ctgcctggag aaaggatggc agcctcaggg cttccttact ttcttctcct ttcctgacag | 3360 |
| agcagccttt ctgtcctgct ctctgctgcc cctcccaata taatccatgg gtacccaggc | 3420 |
| tggttcttgg gctaggttgt gggggccaca ctcacctctt ccctgccagt tctaacacga | 3480 |
| cagacatgaa gccagtgtta gtgggaagag ctgggttttc ccaggatgac cactgcatcc | 3540 |
| tctcctggta cgctctacac tgcttttcagg ctggggacct gccaagtgtg ggacagttga | 3600 |
| tgaggaagag acattagcag ggcctctgga gttgctggcc cagccagctg cccacaagcc | 3660 |
| ataaaccaat aaaataagaa tcctgcgtca cagtttccag ctgggtcctc ttccttgccc | 3720 |
| tcgcactggt gctgctctgg ctgagtagga atacacccac agactgccag gaagatggag | 3780 |
| actgtccgct tccggctcag aactacagtg taattaagct tccaggatca ctaccatgaa | 3840 |
| aacgccgcat tctgctttat catttctacc catgttggga aaaactggct tttccccat | 3900 |
| ttctttacag ggcaaaaaaa aaaaaaaaa aagggagaga gagagagaac tcaacctagt | 3960 |
| tgttatttac cctagtaact ggtgttctat tttttttaa aggggaaaa tttgcattta | 4020 |
| ttttctttt gatggttaac tcctttgtat cataaaatta tgaactctga tatgtaaaac | 4080 |
| agaaaaaaat cttgacaaca gcttctcgct tgtaaaaata tgtattatac agctctattt | 4140 |
| tcaaagtctc ctgaaaaatg actgacctat ctccactg | 4178 |

<210> SEQ ID NO 2
<211> LENGTH: 5864
<212> TYPE: DNA
<213> ORGANISM: Homo sapiens

<400> SEQUENCE: 2

| | |
|---|---|
| acaagtctttt ccgcctcccc agcccgcccg ggagctgcga gccgcgagct ggattatggt | 60 |
| ggcctgagca gccaacgcag ccgcaggagc ccggagcccc tgcccctgcc cgcgccgccg | 120 |
| cccgccgggg ggaccaggga agccgccacc ggcccgccat gcccgcccct cccagccccg | 180 |
| ccgggagccc cgcgcccgct gcccaggctgg ccgccgccgt gccgatgtag cgggctccgg | 240 |
| atcccagcct ctcccctgct cccgtgctct gcggatctcc cctgaccgct ctccacagcc | 300 |
| cggacccggg ggctggccca gggccctgca ggccctggcg tcctgatgcc cccaagctcc | 360 |
| ctctcctgag aagccaccag caccacccag acttgggggc aggcgccagg gacggacgtg | 420 |
| ggccagtgcg agcccagagg gcccgaaggc cggggcccac catggcccaa gccctgccct | 480 |
| ggctcctgct gtggatgggc gcgggagtgc tgcctgccca cggcacccag cacggcatcc | 540 |
| ggctgccccct cgcagcggc ctgggggcg ccccctggg gctgcggctg cccgggagga | 600 |
| ccgacgaaga gcccgaggag cccggccgga ggggcagctt tgtggagatg gtggacaacc | 660 |
| tgagggggcaa gtcggggcag ggctactacg tggagatgac cgtgggcagc ccccgcaga | 720 |
| cgctcaacat cctggtggat acaggcagca gtaactttgc agtgggtgct gcccccccacc | 780 |
| ccttcctgca tcgctactac cagaggcagc tgtccagcac ataccgggac tccggaaagg | 840 |
| gtgtgtatgt gcctacacc cagggcaagt gggaagggga gctgggcacc gacctggtaa | 900 |
| gcatcccca tggccccaac gtcactgtgc gtgccaacat tgctgccatc actgaatcag | 960 |
| acaagttctt catcaacggc tccaactggg aaggcatcct ggggctggcc tatgctgaga | 1020 |
| ttgccaggcc tgacgactcc ctggagcctt tctttgactc tctggtaaag cagacccacg | 1080 |
| ttcccaacct cttctccctg cagctttgtg gtgctggctt cccctcaac cagtctgaag | 1140 |

-continued

```
tgctggcctc tgtcggaggg agcatgatca ttggaggtat cgaccactcg ctgtacacag    1200
gcagtctctg gtatacaccc atccggcggg agtggtatta tgaggtgatc attgtgcggg    1260
tggagatcaa tggacaggat ctgaaaatgg actgcaagga gtacaactat gacaagagca    1320
ttgtggacag tggcaccacc aaccttcgtt tgcccaagaa agtgtttgaa gctgcagtca    1380
aatccatcaa ggcagcctcc tccacggaga agttccctga tggtttctgg ctaggagagc    1440
agctggtgtg ctggcaagca ggcaccaccc cttggaacat tttcccagtc atctcactct    1500
acctaatggg tgaggttacc aaccagtcct tccgcatcac catccttccg cagcaatacc    1560
tgcggccagt ggaagatgtg gccacgtccc aagacgactg ttacaagttt gccatctcac    1620
agtcatccac gggcactgtt atgggagctg ttatcatgga gggcttctac gttgtctttg    1680
atcgggcccg aaaacgaatt ggctttgctg tcagcgcttg ccatgtgcac gatgagttca    1740
ggacggcagc ggtggaaggc cctttttgtca ccttggacat ggaagactgt ggctacaaca    1800
ttccacagac agatgagtca accctcatga ccatagccta tgtcatggct gccatctgcg    1860
ccctcttcat gctgccactc tgcctcatgg tgtgtcagtg gcgctgcctc cgctgcctgc    1920
gccagcagca tgatgacttt gctgatgaca tctccctgct gaagtgagga ggcccatggg    1980
cagaagatag agattcccct ggaccacacc tccgtggttc actttggtca caagtaggag    2040
acacagatgg cacctgtggc cagagcacct caggaccctc cccacccacc aaatgcctct    2100
gccttgatgg agaaggaaaa ggctggcaag gtgggttcca gggactgtac ctgtaggaaa    2160
cagaaaagag aagaaagaag cactctgctg gcgggaatac tcttggtcac ctcaaattta    2220
agtcgggaaa ttctgctgct tgaaacttca gccctgaacc tttgtccacc attcctttaa    2280
attctccaac ccaaagtatt cttcttttct tagtttcaga agtactggca tcacacgcag    2340
gttaccttgg cgtgtgtccc tgtggtaccc tggcagagaa gagaccaagc ttgtttccct    2400
gctggccaaa gtcagtagga gaggatgcac agtttgctat ttgctttaga gacagggact    2460
gtataaacaa gcctaacatt ggtgcaaaga ttgcctcttg aattaaaaaa aaaaactaga    2520
ttgactattt atacaaatgg gggcggctgg aaagaggaga aggagaggga gtacaaagac    2580
agggaatagt gggatcaaag ctaggaaagg cagaaacaca accactcacc agtcctagtt    2640
ttagacctca tctccaagat agcatcccat ctcagaagat gggtgttgtt ttcaatgttt    2700
tcttttctgt ggttgcagcc tgaccaaaag tgagatggga agggcttatc tagccaaaga    2760 gctcttttt agctctctta aatgaagtgc ccactaagaa gttccactta acacatgaat    2820
ttctgccata ttaatttcat tgtctctatc tgaaccaccc tttattctac atatgatagg    2880
cagcactgaa atatcctaac cccctaagct ccaggtgccc tgtgggagag caactggact    2940
atagcagggc tgggctctgt cttcctggtc ataggctcac tctttccccc aaatcttcct    3000
ctggagcttt gcagccaagg tgctaaaagg aataggtagg agacctcttc tatctaatcc    3060
ttaaaagcat aatgttgaac attcattcaa cagctgatgc cctataaccc ctgcctggat    3120
ttcttcctat taggctataa gaagtagcaa gatctttaca taattcagag tggtttcatt    3180
gccttcctac cctctctaat ggcccctcca tttatttgac taaagcatca cacagtggca    3240
ctagcattat accaagagta tgagaaatac agtgctttat ggctctaaca ttactgcctt    3300
cagtatcaag gctgcctgga gaaaggatgg cagcctcagg gcttccttat gtcctccacc    3360
acaagagctc cttgatgaag gtcatctttt tcccctatcc tgttcttccc ctccccgctc    3420
ctaatggtac gtgggtaccc aggctggttc ttgggctagg tagtggggac caagttcatt    3480
```

```
acctccctat cagttctagc atagtaaact acggtaccag tgttagtggg aagagctggg    3540
ttttcctagt atacccactg catcctactc ctacctggtc aacccgctgc ttccaggtat    3600
gggacctgct aagtgtggaa ttacctgata agggagaggg aaatacaagg agggcctctg    3660
gtgttcctgg cctcagccag ctgcccacaa gccataaacc aataaaacaa gaatactgag    3720
tcagttttttt atctgggttc tcttcattcc cactgcactt ggtgctgctt tggctgactg    3780
ggaacacccc ataactacag agtctgacag gaagactgga gactgtccac ttctagctcg    3840
gaacttactg tgtaaataaa cttctcagaac tgctaccatg aagtgaaaat gccacatttt    3900
gctttataat ttctacccat gttgggaaaa actggctttt tcccagccct ttccagggca    3960
taaaactcaa ccccttcgat agcaagtccc atcagcctat tattttttta aagaaaactt    4020
gcacttgttt ttcttttttac agttacttcc ttcctgcccc aaaattataa actctaagtg    4080
taaaaaaaag tcttaacaac agcttcttgc ttgtaaaaat atgtattata catctgtatt    4140
tttaaattct gctcctgaaa aatgactgtc ccattctcca ctcactgcat ttggggcctt    4200
tcccattggt ctgcatgtct tttatcattg caggccagtg gacagaggga aagggagaa    4260
caggggtcgc caacacttgt gttgctttct gactgatcct gaacaagaaa gagtaacact    4320
gaggcgctcg ctcccatgca caactctcca aaacacttat cctcctgcaa gagtgggctt    4380
tccagggtct ttactgggaa gcagttaagc cccctcctca cccccttcctt ttttctttct    4440
ttactccttt ggcttcaaag gattttggaa aagaaacaat atgctttaca ctcattttca    4500
atttctaaat ttgcagggga tactgaaaaa tacggcaggt ggcctaaggc tgctgtaaag    4560
ttgaggggag aggaaatctt aagattacaa gataaaaaac gaatcccta aacaaaaga    4620
acaatagaac tggtcttcca ttttgccacc tttcctgttc atgacagcta ctaacctgga    4680
gacagtaaca tttcattaac caagaaagt gggtcacctg acctctgaag agctgagtac    4740
tcaggccact ccaatcaccc tacaagatgc caaggaggtc ccaggaagtc cagctcctta    4800
aactgacgct agtcaataaa cctgggcaag tgaggcaaga gaaatgagga agaatccatc    4860
tgtgaggtga caggcaagga tgaaagacaa agaaggaaaa gagtatcaaa ggcagaaagg    4920
agatcattta gttgggtctg aaaggaaaag tcttttgctat ccgacatgta ctgctagtac    4980
ctgtaagcat tttaggtccc agaatggaaa aaaaaatcag ctattggtaa tataataatg    5040
tccttttccct ggagtcagtt ttttttaaaaa gttaactctt agtttttact tgtttaattc    5100
taaaagagaa gggagctgag gccattccct gtaggagtaa agataaaagg ataggaaaag    5160
attcaaagct ctaatagagt cacagctttc ccaggtataa aacctaaaat taagaagtac    5220
aataagcaga ggtggaaaat gatctagttc ctgatagcta cccacagagc aagtgattta    5280
taaatttgaa atccaaacta cttttcttaat atcacttttgg tctccatttt tcccaggaca    5340
ggaaatatgt ccccccctaa ctttcttgct tcaaaaatta aaatccagca tcccaagatc    5400
attctacaag taattttgca cagacatctc ctcaccccag tgcctgtctg gagctcaccc    5460
aaggtcacca aacaacttgg ttgtgaacca actgccttaa ccttctgggg gagggggatt    5520
agctagacta ggagaccaga agtgaatggg aaagggtgag gacttcacaa tgttggcctg    5580
tcagagcttg attagaagcc aagacagtgg cagcaaagga agacttggcc caggaaaaac    5640
ctgtgggttg tgctaatttc tgtccagaaa ataggggtgga cagaagcttg tggggtacat    5700
ggaggaattg ggacctggtt atgttgttat tctcggactg tgaatttttgg tgatgtaaaa    5760
cagaatattc tgtaaaccta atgtctgtat aaataatgag cgttaacaca gtaaaatatt    5820
caataagaag tcaaactact agggttaaaa aaaaaaaaaa aaaa                    5864
```

<210> SEQ ID NO 3
<211> LENGTH: 5396
<212> TYPE: DNA
<213> ORGANISM: Mus musculus

<400> SEQUENCE: 3

```
ccgccggcct ccagaacgcg ctttctcggc cgcgcgcgct ctcagtctcc gccacccacc      60
agctccagca ccagcagcag cgccgccgcc accgcccacc ttctgccgcc gccgccacaa     120
ccaccttctc ctccgctgtc ctcttctgtc ctcgccttct gtcgattatc aggctttgaa     180
ccagtatggc tgaccctcgc caggagtttg acacaatgga agaccatgct ggagattaca     240
ctctgctcca agaccaagaa ggagacatgg accatggctt aaaagagtct cccccacagc     300
cccccgccga tgatggagcg gaggaaccag ggtcggagac ctccgatgct aagagcactc     360
caactgctga agacgtgact gcgcccctag tggatgagag agctcccgac aagcaggccg     420
ctgcccagcc ccacacggag atcccagaag gaattacagc cgaagaagca ggcatcggag     480
acaccccgaa ccaggaggac caagccgctg gcatgtgact caagctcgt gtggccagca     540
aagacaggac aggaaatgac gagaagaaag ccaagggcgc tgatggcaaa accggggcga     600
agatcgccac acctcgggga gcagcctctc cggcccagaa gggcacgtcc aacgccacca     660
ggatcccggc caagaccacg cccagcccta agactcctcc agggtcaggt gaaccaccaa     720
aatccggaga acgaagcggc tacagcagcc ccggctctcc cggaacgcct ggcagtcgct     780
cgcgcacccc atccctacca acaccgccca cccgggagcc caagaaggtg cagtggtcc      840
gcactccccc taagtcacca tcagctagta agagccgcct gcagactgcc cctgtgccca     900
tgccagacct aaagaatgtc aggtcgaaga ttggctctac tgagaacctg aagcaccagc     960
caggaggtgg caaggtgcag ataattaata agaagctgga tcttagcaac gtccagtcca    1020
agtgtggctc gaaggataat atcaaacacg tcccggtgg aggcagtgtg caaatagtct     1080
acaagccggt ggacctgagc aaagtgacct ccaagtgtgg ctcgttaggg aacatccatc    1140
acaagccagg aggtgccag gtggaagtaa aatcagagaa gctggacttc aaggacagag     1200
tccagtcgaa gattggctcc ttggataata tcacccacgt ccctggagga gggaataaga    1260
agattgaaac ccacaagctg accttcaggg agaatgccaa agccaagaca gaccatggag    1320
cagaaattgt gtataagtca cccgtggtgt ctggggacac atctccacgg cacctcagca    1380
atgtgtcttc cacgggcagc atcgacatgg tggactcacc acagcttgcc acactagccg    1440
atgaagtgtc tgcttccttg gccaagcagg gtttgtgatc aggctcccag gcagtcaat     1500
aatcatggag agaagagaga gtgagagtgt ggaaaaaaaa aaaaaaaaag aatgatctgg    1560
ccccttgccc tctgccctcc ccgctgctcc tcatagacag gctgacctgc ttgtcaccta    1620
acctgctttt gtggctcgga tttggctcgg acttcaaaaa tcagtgatgg gaaaagtaca    1680
tttcatcttt ccaaattgat ttgtgggcta aaaataaaac atatttaagg gaaaaaaaa     1740
catgtaaaaa catggccaaa aaatttcctt gggcaattgc taattgattt ccccccctg     1800
accccgccct ccctctctga gtattagagg gtgaagaagg ctctggaggc tgcttctggg    1860
gagtggctga gggactaggg cagctaattg cccatagccc catcctaggg gcttcaggga    1920
cagtggcagc aatgagagat ttgagacttg tgtgttcgt ggggccgtag gcaggtgctg      1980
ttaacttgtg tgggtgtgag tggggactga acagcgaca gcgaaggctg agagatggat     2040
gggtggactg agttagagga cagaggtgag gaaggcaggt tgggagaggg gacactggct    2100
```

```
ccttgccaag tagcttgggg aggacagggt gctgcagctg cctgcagcag tcctagctag    2160
ctcagatgcc tgcttgataa agcactgtgg gggtaacgtg ggtgtgtgtg ccccttctgc    2220
agggcagcct gtgggagaag gggtattggg cagaaggaag gtaagccagc aggtggtacc    2280
ttgtagattg gttctcttga aggctgctct tgacatccca gggcactggc ttcttcctcc    2340
ctccccgcaa ggtgggaggt cctgagcgag gtgtttccct tcgctcccac aggaaaagct    2400
gctttactga gttctcaagt ttggaactac agccatgatt tggccaccat tacagacctg    2460
ggactttagg gctaaccaga tctttgtaag gacttgtgcc tcttggggga cctctgcctg    2520
ttctcatgct tggccctctg gcacttctgt agtgggaggg atgggggggtg gtattctggg   2580
atgtgggtcc caggcctccc atccctcaca cagccactgt atccctctc tctgtcctat     2640
catgcccacg tctgccacga gagctagtca ctgccgtccg tacatcacgt ctcactgtcc    2700
tgagtgccat gcctctccca gccccatcc ctggcccctg ggtagatatg ggcaatatct     2760
gctctacact aggggttgga gtccaggaa ggcaaagatt tgggcctcag tctctagtcc     2820
tacgttccac gaatccaacc agtgtgcctc ccacaaggaa ccttacgacc ttgtttggtt    2880
cactccatta cttcctatcc tggatggaa ctggtgtgtg cctgcctggg gatgaccttg     2940
gacctctgcc ttttcttta tctaagtgga tgcctcctag gcctgactcc ttgtgttgag     3000
ctggaggcag ccaagtcagg tgccaatgtc ttggcatcag taagaacagt caagagtccc    3060
agggcagggc cacacttctc ccatctttcg cttccacccc agcttgtgat cgctagcctc    3120
ccagagctca gctgccatta agtccccatg cacgtaatca gtctccacac cccagtttgg    3180
ggaacatacc cccttgattg aagtgttttt ttcctccggt cccatggaaa ccatgctgcc    3240
tgccctgctg gagcagacgg ccacctccat agatgcagcc cttcttcc cgtcttcgcc      3300
ctgttacgtt gtagttggat ttgtctgttt gtctgggttc accagagtga ctatgatagt    3360
gaaagaaaa gaaagaaaaa gaaaaaaaa aaaaaaaga aaagaaaaa ggaaaaaaaa        3420
aaggacgcat gtatcttgaa atatttgtca aaaggttcta gcccaccacg tgatggagag    3480
tctggatatc tccttcctga cgtggctcca ggccagtgca gtgctaacct gctgggacat    3540
cccatgtttt gaagggtttc ttctgcatct gggacctcac agacactgga ttgtgacatt    3600
ggaggtctgt gacattggag gtcaatggca ttggccaagg cctgaagcac aggaccagct    3660
agaggcagca ggctccgagt gccagggaga gcttgtggct ggcctgtttt gtatgaagat    3720
ggtcctttct gatcacgact tcaaatccca cagtagccct gaaagacatc taagaactcc    3780
tgcatcacaa gagaaaagga caccagtacc agcaggaga gctgtgaccc tagaaattcc    3840
atgacgaccc agtagatatc cttgggccct ctccaagcct gggcttttc accatagagt    3900
ttgggatgga ctgtcccact gatgaagggg acatcttagg agactcctt ggtttccaag   3960
ctgtcagccc cctgaacttg cacgacctcc tacagcttca gggactaggc cttttgaagat  4020
taggaacctc aggcccacat cagccacttc tgatgtacag ttaaggacaa tgtgagact     4080
aggaggaagc agccagcctt tcccattaaa gaactcttga gtgcccaggg ctacctattg    4140
tgagcttccc cactgataag actttagctg tccatagaag tgagtccgag ggaggaaaag    4200
tgtggtttct tcatcatggt tacctgtcgt ggttctctct cttacaccca tttacccatc    4260
ccgcagttcc tgtccttgaa tggggggtgg ggtgctctgc ctatctcttg tggggtgatc    4320
agcccaaaaa tcatgatttg gagtgatctg atcagtgctg ataggcagtt tacaaaggga    4380
ttctggcttg tgacttcagt gaggacaatc ccccagggcc ctttctttcc atgcctctcc    4440
aactcagagc caatgtcttt gggtgggcta gatagatagg gcatacaatt ggcctggttc    4500
```

-continued

```
ctccaagctc ttaattcact ttatcaatag ttccatttaa attgacttca atgataagag    4560
tgtatcccat ttgagattgc ttgcgttgtg ggggagggg aggaggaaca cattaagata     4620
attcacatgg gcaaagggag gtcttggagt gtagccgtta agccatcttg taacccatt     4680 catgattttg accacctgct agagagaaga ggtgccaaga gactagaact tggaggcttg    4740
gctgtcccac taataggctt tcgcaaggca gaggtagcca gctaggtccc tgccttccca    4800
gccaggtaca gctctcaggt ttgtggaggt aatctgtgaa cttctcttcc tgctgccttc    4860
ttgtgatgtc cagagcccac agtcaaatac ctcctaagaa ccctggcttc cttccctcta    4920
atccactggc acatgactat cacctctgga ttgacctcag atccatagcc tacacactgc    4980
tagcagtggc caagatcact tcctttatct ccatctgttc tgttctccag gaaagtaagt    5040
ggggatgagg gtggaggtgg taatcaactg tagatctgtg gctttatgag ccttcagact    5100
tctctctggc ttcttctgga agggttacta ttggcagtat tgcaatctca ccctcctgat    5160
gaactgtagc ctgtgccgtt actgtgctgg gcatgatctc cagtgcttgc aagtcccatg    5220
atttctttgg tgattttgag ggtgggggga gggacacaaa tcagcttagc ttagcttcct    5280
gtctgtgaat gtccatatag tgtattgtgt tttaacaaat gatctacact gactgttgct    5340
gtaaaagtga atttggaaat aaagttatta ctctgaataa aaaaaaaaa aaaaaa        5396
```

<210> SEQ ID NO 4
<211> LENGTH: 6762
<212> TYPE: DNA
<213> ORGANISM: Homo sapiens

<400> SEQUENCE: 4

```
ggacggccga gcggcagggc gctcgcgcgc gcccactagt ggccggagga gaaggctccc      60
gcggaggccg cgctgcccgc cccctcccct ggggaggctc gcgttcccgc tgctcgcgcc     120
tgcgccgccc gccggcctca ggaacgcgcc ctcttcgccg gcgcgcgccc tgcagtcac     180 cgccacccac cagctccggc accaacagca gcgccgctgc caccgccacc cttctgccgc    240
cgccaccaca gccaccttct cctcctccgc tgtcctctcc cgtcctcgcc tctgtcgact    300
atcaggtgaa ctttgaacca ggatggctga gcccgccag gagttcgaag tgatggaaga    360
tcacgctggg acgtacgggt tggggacag gaaagatcag ggggctaca ccatgcacca     420 agaccaagag ggtgacacgg acgctggcct gaaagaatct ccctgcaga cccccactga     480 ggacggatct gaggaaccgg gctctgaaac ctctgatgct aagagcactc aacagcgga     540 agatgtgaca gcacccttag tggatgaggg agctccggc aagcaggctg ccgcgcagcc     600
ccacacggag atcccagaag gaaccacagc tgaagaagca ggcattggag acacccccag    660
cctggaagac gaagctgctg gtcacgtgac ccaagagcct gaaagtggta aggtggtcca    720
ggaaggcttc ctccgagagc caggcccccc aggtctgagc caccagctca tgtccggcat    780
gcctggggct cccctcctgc ctgagggccc cagagaggcc acgccaac cttcgggga      840 aggacctgag gacacagagg gcggccgcca cgcccctgag ctgctcaagc accagcttct    900
aggagacctg caccaggagg ggccgccgct gaagggggca ggggcaaag agaggccggg     960 gagcaaggag gaggtggatg aagaccgcga cgtcgatgag tcctcccccc aagactcccc    1020 tcctccaag gcctcccag cccaagatgg gcggcctccc cagacagccg ccagagaagc      1080
caccagcatc ccaggcttcc cagcggaggg tgccatcccc ctccctgtgg atttcctctc     1140 caaagttcc acagagatcc cagcctcaga gcccgacggg cccagtgtag ggcgggccaa      1200
```

```
agggcaggat gcccccctgg agttcacgtt tcacgtggaa atcacaccca acgtgcagaa  1260
ggagcaggcg cactcggagg agcatttggg aagggctgca tttccagggg cccctggaga  1320
ggggccagag gcccggggcc cctctttggg agaggacaca aaagaggctg accttccaga  1380
gccctctgaa aagcagcctg ctgctgctcc gcggggaag cccgtcagcc gggtccctca   1440
actcaaagct cgcatggtca gtaaaagcaa agacgggact ggaagcgatg acaaaaaagc  1500
caagacatcc acacgttcct ctgctaaaac cttgaaaaat aggccttgcc ttagccccaa  1560
acaccccact cctggtagct cagaccctct gatccaaccc tccagccctg ctgtgtgccc  1620
agagccacct tcctctccta aatacgtctc ttctgtcact cccgaactg gcagttctgg    1680 agcaaaggag atgaaactca aggggctga tggtaaaacg aagatcgcca caccgcgggg    1740
agcagcccct ccaggccaga agggccaggc caacgccacc aggattccag caaaaacccc   1800
gcccgctcca aagacaccac ccagctctgg tgaacctcca aaatcagggg atcgcagcgg   1860
ctacagcagc cccggctccc caggcactcc cggcagccgc tcccgcaccc cgtcccttcc   1920
aaccccaccc acccgggagc caagaaggt ggcagtggtc cgtactccac ccaagtcgcc    1980
gtcttccgcc aagagccgcc tgcagacagc cccgtgccc atgccagacc tgaagaatgt   2040
caagtccaag atcggctcca ctgagaacct gaagcaccag ccgggaggcg gaaggtgca    2100 gataattaat aagaagctgg atcttagcaa cgtccagtcc aagtgtggct caaggataa    2160 tatcaaaaac gtcccgggag gcggcagtgt gcaaatagtc tacaaaccag ttgacctgag   2220
caaggtgacc tccaagtgtg gctcattagg caacatccat cataaaccag gaggtggcca   2280
ggtggaagta aaatctgaga agcttgactt caaggacaga gtccagtcga agattgggtc   2340
cctggacaat atcacccacg tccctggcgg aggaaataaa aagattgaaa cccacaagct   2400
gaccttccgc gagaacgcca aagccaagac agaccacggg gcggagatcg tgtacaagtc   2460
gccagtggtg tctggggaca cgtctccacg gcatctcagc aatgtctcct ccaccggcag   2520
catcgacatg gtagactcgc cccagctcgc cacgctagct gacgaggtgt ctgcctccct   2580
ggccaagcag ggtttgtgat caggcccctg gggcggtcaa taattgtgga gaggagagaa   2640
tgagagagtg tggaaaaaaa aagaataatg acccggcccc cgccctctgc ccccagctgc   2700
tcctcgcagt tcggttaatt ggttaatcac ttaacctgct tttgtcactc ggctttggct   2760
cgggacttca aaatcagtga tgggagtaag agcaaatttc atctttccaa attgatgggt   2820
gggctagtaa taaatatttt aaaaaaaaac attcaaaaac atggccacat ccaacatttc   2880
ctcaggcaat tccttttgat tctttttttct tcccccctcca tgtagaagag ggagaaggag   2940
aggctctgaa agctgcttct gggggatttc aagggactgg gggtgccaac cacctctggc   3000
cctgttgtgg gggtgtcaca gaggcagtgg cagcaacaaa ggatttgaaa cttggtgtgt   3060
tcgtggagcc acaggcagac gatgtcaacc ttgtgtgagt gtgacggggg ttggggtggg   3120 gcggaggcc acggggagg ccgaggcagg ggctgggcag aggggagagg aagcacaaga    3180
agtgggagtg ggagaggaag ccacgtgctg gagagtagac atcccctcc ttgccgctgg   3240 gagagccaag gcctatgcca cctgcagcgt ctgagcggcc gcctgtcctt ggtggccggg   3300
ggtgggggcc tgctgtgggt cagtgtgcca ccctctgcag ggcagcctgt gggagaaggg   3360
acagcgggta aaagagaag gcaagctggc aggagggtgg cacttcgtgg atgacctcct   3420
tagaaaagac tgaccttgat gtcttgagag cgctggcctc ttcctccctc cctgcagggt  3480
agggggcctg agttgagggg cttccctctg ctccacagaa accctgtttt attgagttct  3540
gaaggttgga actgctgcca tgattttggc cactttgcag acctgggact ttagggctaa  3600
```

```
ccagttctct tgtaaggac ttgtgcctct tgggagacgt ccacccgttt ccaagcctgg    3660
gccactggca tctctggagt gtgtgggggt ctggggaggca ggtcccgagc cccctgtcct    3720
tcccacggcc actgcagtca ccccgtctgc gccgctgtgc tgttgtctgc cgtgagagcc    3780
caatcactgc ctatacccct catcacacgt cacaatgtcc cgaattccca gcctcaccac    3840
cccttctcag taatgaccct ggttggttgc aggaggtacc tactccatac tgagggtgaa    3900
attaagggaa ggcaaagtcc aggcacaaga gtgggacccc agcctctcac tctcagttcc    3960
actcatccaa ctgggaccct caccacgaat ctcatgatct gattcggttc cctgtctcct    4020
cctcccgtca cagatgtgag ccagggcact gctcagctgt gacccctaggt gtttctgcct    4080 tgttgacatg gagagagccc tttccctga gaaggcctgg cccttcctg tgctgagccc    4140 acagcagcag gctgggtgtc ttggttgtca gtggtggcac caggatggaa gggcaaggca    4200
cccagggcag gcccacagtc ccgctgtccc ccacttgcac cctagcttgt agctgccaac    4260
ctcccagaca gcccagcccg ctgctcagct ccacatgcat agtatcagcc ctccacaccc    4320
gacaaagggg aacacacccc cttggaaatg gttcttttcc cccagtccca gctggaagcc    4380
atgctgtctg ttctgctgga gcagctgaac atatacatag atgttgccct gcctccccca    4440
tctgcaccct gttgagttgt agttggattt gtctgtttat gcttggattc accagagtga    4500
ctatgatagt gaaagaaaaa aaaaaaaaaa aaaaggacgc atgtatcttg aaatgcttgt    4560
aaagaggttt ctaacccacc ctcacgaggt gtctctcacc cccacactgg gactcgtgtg    4620
gcctgtgtgg tgccaccctg ctggggcctc ccaagttttg aaaggctttc ctcagcacct    4680
gggacccaac agagaccagc ttctagcagc taaggaggcc gttcagctgt gacgaaggcc    4740
tgaagcacag gattaggact gaagcgatga tgtccccttc cctacttccc cttgggctc    4800 cctgtgtcag ggcacagact aggtcttgtg gctggtctgg cttgcggcgc gaggatggtt    4860
ctctctggtc atagcccgaa gtctcatggc agtcccaaag gaggcttaca actcctgcat    4920
cacaagaaaa aggaagccac tgccagctgg ggggatctgc agctcccaga agctccgtga    4980
gcctcagcca ccctcagac tgggttcctc tccaagctcg ccctctggag gggcagcgca    5040
gcctcccacc aagggccctg cgaccacagc agggattggg atgaattgcc tgtcctggat    5100
ctgctctaga ggcccaagct gcctgcctga ggaaggatga cttgacaagt caggagacac    5160
tgttcccaaa gccttgacca gagcacctca gcccgctgac cttgcacaaa ctccatctgc    5220
tgccatgaga aaagggaagc cgcctttgca aaacattgct gcctaaagaa actcagcagc    5280
ctcaggccca attctgccac ttctggtttg ggtacagtta aaggcaaccc tgagggactt    5340
ggcagtagaa atccagggcc tccctggg ctggcagctt cgtgtgcagc tagagcttta    5400
cctgaaagga agtctctggg cccagaactc tccaccaaga gcctccctgc cgttcgctga    5460
gtcccagcaa ttctcctaag ttgaagggat ctgagaagga aaggaaatg tggggtagat    5520 ttggtggtgg ttagagatat gccccctca ttactgccaa cagttcggc tgcatttctt    5580 cacgcacctc ggttcctctt cctgaagttc ttgtgccctg ctcttcagca ccatgggcct    5640
tcttatacgg aaggctctgg gatctccccc ttgtggggca ggctcttggg gccagcctaa    5700
gatcatggtt tagggtgatc agtgctggca gataaattga aaaggcacgc tggcttgtga    5760
tcttaaatga ggacaatccc cccagggctg ggcactcctc ccctcccctc acttctccca    5820
cctgcagagc cagtgtcctt gggtgggcta gataggatat actgtatgcc ggctccttca    5880
agctgctgac tcactttatc aatagttcca tttaaattga cttcagtggt gagactgtat    5940
```

```
cctgtttgct attgcttgtt gtgctatggg gggaggggg aggaatgtgt aagatagtta      6000
acatgggcaa agggagatct tggggtgcag cacttaaact gcctcgtaac ccttttcatg      6060
atttcaacca catttgctag agggagggag cagccacgga gttagaggcc cttgggttt      6120
ctcttttcca ctgacaggct ttcccaggca gctggctagt tcattccctc cccagccagg      6180
tgcaggcgta ggaatatgga catctggttg ctttggcctg ctgccctctt tcagggtcc      6240
taagcccaca atcatgcctc cctaagacct tggcatcctt ccctctaagc cgttggcacc      6300
tctgtgccac ctctcacact ggctccagac acacagcctg tgcttttgga gctgagatca      6360
ctcgcttcac cctcctcatc tttgttctcc aagtaaagcc acgaggtcgg ggcgagggca      6420
gaggtgatca cctgcgtgtc ccatctacag acctgcagct tcataaaact tctgatttct      6480
cttcagcttt gaaaagggtt accctgggca ctggcctaga gcctcacctc ctaatagact      6540
tagccccatg agtttgccat gttgagcagg actatttctg gcacttgcaa gtcccatgat      6600
ttcttcggta attctgaggg tgggggagg acatgaaat catcttagct tagctttctg      6660
tctgtgaatg tctatatagt gtattgtgtg ttttaacaaa tgatttacac tgactgttgc      6720
tgtaaaagtg aatttggaaa taaagttatt actctgatta aa                        6762

<210> SEQ ID NO 5
<211> LENGTH: 6982
<212> TYPE: DNA
<213> ORGANISM: Mus musculus

<400> SEQUENCE: 5
aggcattcag gcagcgagag cagagcagcg tagagcagca cagctgagct cgtgaggcag        60
gagactcagc ccgaggaaat cgcagataag ttttaatta aaaagattga gcagtaaaaa       120
gaattagaac tctaaactta agctaataga gtagcttatc gaaatattac ttagtcttaa       180
taatctaaga agatcttaag agataacatg aaggcttatt taaacagttt gaaaaaggaa       240
atgaggagaa aagtatttgt actgtataat ggaggctgac cagagcagtt taggagattg       300
taaagggagg ttttgtgaag ttctaaaagg ttctagtttg aaggtcggcc ttgtagatta       360
aaacgaaggt tacctaaata gaatctaagt ggcatttaaa acagtaaagt tgtagagaat       420
agtttgaaaa tgaggtgtag ttttaaaaga ttgagaaaag taggttaagt tgacggccgt       480
tataaaaatc cttcgactgg cgcatgtacg tttgaaggca tgagttggaa acagggaaga       540
tggaagtgtt aggctagccg ggcgatggtg gcgcacgcct ttaatcctag cacttgggag       600
gcagaggcag gcggatttct gagttcgagg ccagcctggt ctacagagtg agttccagga       660
cagccagggc tacacagaga aaccctgtct tgaaaaaaca aaaaggttag gctagtattt       720
ggagaaagaa gattagaaaa tggaagtgaa agacgaagaa gacatacagg aaggtgaaga       780
aaaagctgtt agagaagata ggaaaataga agacaaagca tctttagaag acagaaaagg       840
tacttaaagg cacaggtagt aggaagccga agaatagaag atagaaagaa gcaagataga       900
aaaacaaaat ggaagttaag acaactttgg atgccagcat tcaagatagg caaagaagat       960
aagattgagg ccaaaaggtt ggataagata taaagtcaga aggaaattat ctttaaagcc      1020
ataagttcaa atttctgatg gagcgagcag tttagaagag tctttagaca gccacataca      1080
agattgaagc tagcaatcaa agctactagg actgaagtaa aaagttaagg cagaatgcct      1140
ttgaagagtt agaagaatat taaaagcctt aacttgtagc ttaattttgc ttgatgacaa      1200
aaggactttt gataacagtt tcaagattgt cagcattttg cattggactt gagctgaggt      1260
gcttttaaaa tcctaacgac tagcattggc agctgaccca ggtctacaca gaagtgcatt      1320
```

```
cagtgaacta ggaagacagg agcggcagac aggagtcccg aagccagttt ggtgaagcta    1380
ggaaggactg aggagccagc agcagcagtg catggtgaag atagcccagg aaagagtgcg    1440
gttcggtgga ggaagctagg aagaaggagc catacggatg tggtggtgaa gctgggaaag    1500
ggttccagga tggtggagcg agagcgagtt ggtgatgaag ctagctggcg gcttggcttg    1560
tcaactgcgc ggaggaggcg agcaggcatt gtggagagga tagatagcgg ctcctagacc    1620
agcatgccag tgtgcaagaa aggctgcagg gagagcatgc ggtgcggtaa cattccttga    1680
ggtcggcaac atggtggtgg ttttctgtaa cttggatggt aacttgttta ctttgtctta    1740
atagttatgg gggagttgta ggcttctgtg taaagagata tatctggggc tgtatgtagg    1800
cctttgcggg tgttgtaggt ttttcttttt cagggttatg tcctcttgca tcttgtcaga    1860
agcttttgag ggctgactgc caaggcccag aaagaagaat ggtagatggc aagttgtctt    1920
taaccgctca gagggaatg aatggtagag ccagcacaac ctcccagttt tgtaagacgt     1980
tgtagtttga acagatgacc taccacaagc ctcactcctg tgtaggggag gtaattgggc    2040
aaagtgcttt tggggaatg ggggcaaaat atattttgag ttcttttccc cttaggtctg     2100
tctagaatcc taaaggcaga tgactcaagg gaaccagaaa aaaggaaatc cactctcagg    2160
ataagcagag ctcgccaggt ttacagtttg taggaagtag aggatggatg ctagctttca    2220
cactgagtgt ggaggagctg gccatggcgg aattgctggt agtttactct ttccccctcc    2280
cttaatgaga tttgtaaaat cctaaacact tttacttgaa atatttggga gtggtcttaa    2340
cagggaggag tgggtggggg aaacgttttt tttctaagat tttccacaga tgctatagtt    2400
gtgttgacac actgggttag agaaggcgtg tactgctatg ctgttggcac gacaccttca    2460
gggactggag ctgccttttg tccttggaag agttttccca gttgccgctg aagtcagcac    2520
agtgcggctt tggttcacag tcacctcagg agaacctcag gagcttggct aggccagagg    2580
ttgaagttaa gttttacagc accgtgattt aaaatatttc attaaagggg aggggtaaaa    2640
cttagttggc tgtggccttg tgtttgggtg ggtgggggtg ttaggtaatt gtttagttta    2700
tgatttcaga taatcatacc agagaactta aatatttgga aaaacaggaa atctcagctt    2760
tcaagttggc aagtaactcc caatccagtt tttgcttctt ttttcctttt tctttttttg    2820
aggcgggcag ctaaggaagg ttggttcctc tgccggtccc tcgaaagcgt agggcttggg    2880
ggttggtctg gtccactggg atgatgtgat gctacagtgg ggactcttct gaagctgttg    2940
gatgaatata gattgtagtg tgtggttctc ttttgaaatt ttttcaggt gacttaatgt      3000 atcttaataa ctactatagg aacaaaggaa gtggctttaa tgaccctgaa ggaatttctc    3060
ctggtgatag cttttatatt atcaagtaag agatactatc tcagttttgt ataagcaagt    3120 cttttttccta gtgtaggaga aatgattttc cttgtgacta aacaagatgt aaaggtatgc    3180
tttttttctt cttgtgcatt gtatacttgt gtttatttgt aacttataat ttaagaatta    3240
tgataattca gcctgaatgt cttttagagg gtgggctttt gttgatgagg gaggggaaac    3300 ctttttttt ctgtagacct ttttcagata acaccatctg agtcataacc agcctggcag     3360
tgtgatgacg tagatgcaga gggagcagct ccttggtgaa tgagtgataa gtaaaggcag    3420
aaaaaataat gtcatgtctc catggggaat gagcatgagc cagagattgt tcctactgat    3480
gaaaagctgc atatgcaaaa atttaagcaa atgaaagcaa ccagtataaa gttatggcaa    3540
tacctttaaa agttatggct tatctaccaa gctttatcca caaaagtaaa gaattgatga    3600
aaaacagtga agatcaaatg ttcatctcaa aactgctttt acaaaagcag aatagaaatg    3660
```

```
aagtgaaaat gctgcattaa gcctggagta aaaagaagct gagcttgttg agatgagtgg    3720
gatcgagcgg ctgcgaggcg gtgcagtgtg ccaatgtttc gtttgcctca gacaggtttc    3780
tcttcataag cagaagagtt gcttcattcc atctcggagc aggaaacagc agactgctgt    3840
tgacagataa gtgtaacttg gatctgcagt attgcatgtt agggatagat aagtgccttt    3900
tttctctttt tccaaaaaga cctgtagagc tgttgaatgt ttgcagctgg cccctcttag    3960
gcagttcaga attttgagta gttttcccat ccagcctctt aaaaattcct aagccttgca    4020
ccgatgggct ttcatgatgg gatagctaat aggcttttgc atcgtaaact tcaacacaaa    4080
agcctacatg attaatgcct actttaatta cattgcttac aagattaagg aatctttatc    4140
ttgaagaccc catgaaaggg atcattatgt gctgaaaatt agatgttcat attgctaaaa    4200
tttaaatgtg ctccaatgta cttgtgctta aaatcattaa attatacaaa ttaataaaat    4260
acttcactag agaatgtatg tatttagaag gctgtctcct tatttaaata aagtcttgtt    4320
tgttgtctgt agttagtgtg ggcaattttg gggggatgtt cttctctaat cttttcagaa    4380
acttgacttc gaacacttaa gtggaccaga tcaggatttg agccagaaga ccgaaattaa    4440
ctttaaggca ggaaagacaa attttattct ccatgcagtg atgagcattt ataattgca    4500 ggcctggcat agaggccgtc taactaagga ctaagtacct taggcaggtg ggagatgatg    4560
gtcagagtaa aagtaactaa catattttgt ttccagaaag tcaggggtct aatttgacca    4620
tggctaaaca tctagggtaa gacacttttc ccccacattt ccaaatatgc atgttgagtt    4680
taaatgctta cgatcatctc atccacttta gccttttgtc acctcacttg agccacgagt    4740
ggggtcaggc atgtgggttt aaagagtttt cctttgcaga gcctcatttc atccttcatg    4800
gagctgctca ggactttgca tataagcgct tgcctctgtc ttctgttctg ctagtgagtg    4860
tgtgatgtga gaccttgcag tgagtttgtt tttcctggaa tgtggaggga ggggggatg    4920 gggcttactt gttctagctt ttttttaca gaccacacag aatgcaggtg tcttgacttc    4980
aggtcatgtc tgttctttgg caagtaatat gtgcagtact gttccaatct gctgctatta    5040
gaatgcattg tgacgcgact ggagtatgat taaagaaagt tgtgtttccc caagtgtttg    5100
gagtagtggt tgttggagga aaagccatga gtaacaggct gagtgttgag gaaatggctc    5160
tctgcagctt taagtaaccc gtgtttgtga ttggagccga gtccctttgc tgtgctgcct    5220
taggtaaatg ttttttgttca tttctggtga ggggggttgg gagcactgaa gcctttagtc    5280
tcttccagat tcaacttaaa atctgacaag aaataaatca gacaagcaac attcttgaag    5340
aaattttaac tggcaagtgg aaatgttttg aacagttccg tggtctttag tgcattatct    5400
ttgtgtaggt gttctctctc ccctcccttg gtcttaattc ttacatgcag gaacattgac    5460
aacagcagac atctatctat tcaaggggcc agagaatcca gacccagtaa ggaaaaatag    5520
cccatttact ttaaatcgat aagtgaagca gacatgccat tttcagtgtg gggattggga    5580
agccctagtt ctttcagatg tacttcagac tgtagaagga gcttccagtt gaattgaaat    5640
tcaccagtgg acaaaatgag gacaacaggt gaacgagcct tttcttgttt aagattagct    5700
actggtaatc tagtgttgaa tcctctccag cttcatgctg gagcagctag catgtgatgt    5760
aatgttggcc ttggggtgga ggggtgaggt gggcgctaag cctttttta agattttca    5820 ggtaccccctc actaaaggca ctgaaggctt aatgtaggac agcggagcct tcctgtgtgg    5880
caagaatcaa gcaagcagta ttgtatcgag accaaagtgg tatcatggtc ggttttgatt    5940
agcagtgggg actaccctac cgtaacacct tgttggaatt gaagcatcca aagaaaatac    6000
ttgagaggcc ctgggcttgt tttaacatct ggaaaaaagg ctgttttat agcagcggtt    6060
```

| | |
|---|---|
| accagcccaa acctcaagtt gtgcttgcag gggagggaaa aggggggaaag cgggcaacca | 6120 |
| gtttccccag cttttccaga atcctgttac aaggtctccc cacaagtgat ttctctgcca | 6180 |
| catcgccacc atgggccttt ggcctaatca cagacccttc acccctcacc ttgatgcagc | 6240 |
| cagtagctgg atccttgagg tcacgttgca tatcggtttc aaggtaacca tggtgccaag | 6300 |
| gtcctgtggg ttgcaccaga aaaggccatc aatttcccc ttgcctgtaa tttaacatta | 6360 |
| aaaccatagc taagatgttt tatacatagc acctatgcag agtaaacaaa ccagtatggg | 6420 |
| tatagtatgt ttgataccag tgctgggtgg gaatgtagga agtcggatga aaagcaagcc | 6480 |
| tttgtaggaa gttgttgggg tgggattgca aaaattctct gctaagactt tttcaggtgg | 6540 |
| acataacaga cttggccaag ctagcatctt agtggaagca gattcgtcag tagggttgta | 6600 |
| aaggttttc ttttcctgag aaaacaacct tttgttttct caggttttgc ttttttggcct | 6660 |
| ttccctagct ttaaaaaaaa aaaagcaaaa gacgctggtg gctggcactc ctggtttcca | 6720 |
| ggacggggtt caagtccctg cggtgtcttt gcttgactct tatatcatga ggccattaca | 6780 |
| tttttcttgg agggttctaa aggctctggg tatggtagct gatatcactg gaacactccc | 6840 |
| cagcctcagt gttgaactct tgataattaa ctgcattgtc tttcaggtta tgcccaattc | 6900 |
| gtcttattac ctctgagtcg acacacctcc tactatttat tgaatacttt gattttatga | 6960 |
| aataaaaact aaatatctct ca | 6982 |

<210> SEQ ID NO 6
<211> LENGTH: 8758
<212> TYPE: DNA
<213> ORGANISM: Homo sapiens

<400> SEQUENCE: 6

| | |
|---|---|
| gtaaaggact ggggccccgc aactggcctc tcctgccctc ttaagcgcag cgccatttta | 60 |
| gcaacgcaga agcccggcgc cgggaagcct cagctcgcct gaaggcaggt ccctctgac | 120 |
| gcctccggga gcccaggttt cccagagtcc ttggacgca gcgacgagtt gtgctgctat | 180 |
| cttagctgtc cttataggct ggccattcca ggtggtggta tttagataaa accactcaaa | 240 |
| ctctgcagtt tggtcttggg gtttggagga aagcttttat ttttcttcct gctccggttc | 300 |
| agaaggtctg aagctcatac ctaaccaggc ataacacaga atctgcaaaa caaaaacccc | 360 |
| taaaaagca gacccagagc agtgtaaaca cttctgggtg tgtccctgac tggctgccca | 420 |
| aggtctctgt gtcttcggag acaaagccat tcgcttagtt ggtctacttt aaaaggccac | 480 |
| ttgaactcgc tttccatggc gatttgcctt gtgagcactt tcaggagagc ctggaagctg | 540 |
| aaaaacggta gaaaaatttc cgtgcgggcc gtgggggct gcggcaact gggggccgc | 600 |
| agatcagagt gggccactgg cagccaacgg ccccgggc tcaggcgggg agcagctctg | 660 |
| tggtgtggga ttgaggcgtt ttccaagagt gggttttcac gtttctaaga tttcccaagc | 720 |
| agacagcccg tgctgctccg atttctcgaa caaaaaagca aaacgtgtgg ctgtcttggg | 780 |
| agcaagtcgc aggactgcaa gcagttgggg gagaaagtcc gccattttgc cacttctcaa | 840 |
| ccgtccctgc aaggctgggg ctcagttgcg taatggaaag taaagccctg aactatcaca | 900 |
| ctttaatctt ccttcaaaag gtggtaaact atacctactg tccctcaaga gaacacaaga | 960 |
| agtgctttaa gaggtatttt aaaagttccg ggggtttgt gaggtgtttg atgacccgtt | 1020 |
| taaaatatga tttccatgtt tcttttgtct aaagtttgca gctcaaatct ttccacacgc | 1080 |
| tagtaattta agtatttctg catgtgtagt ttgcattcaa gttccataag ctgttaagaa | 1140 |

```
aaatctagaa aagtaaaact agaacctatt tttaaccgaa gaactacttt ttgcctccct    1200
cacaaaggcg gcggaaggtg atcgaattcc ggtgatgcga gttgttctcc gtctataaat    1260
acgcctcgcc cgagctgtgc ggtaggcatt gaggcagcca gcgcaggggc ttctgctgag    1320
ggggcaggcg gagcttgagg aaaccgcaga taagttttttt tctctttgaa agatagagat    1380
taatacaact acttaaaaaa tatagtcaat aggttactaa gatattgctt agcgttaagt    1440
ttttaacgta atttaatag cttaagattt taagagaaaa tatgaagact tagaagagta    1500
gcatgaggaa ggaaaagata aaggtttct aaaacatgac ggaggttgag atgaagcttc     1560
ttcatggagt aaaaaatgta tttaaaagaa aattgagaga aaggactaca gagccccgaa    1620
ttaataccaa tagaagggca atgcttttag attaaaatga aggtgactta aacagcttaa    1680
agtttagttt aaaagttgta ggtgattaaa ataatttgaa ggcgatcttt taaaaagaga    1740
ttaaaccgaa ggtgattaaa agaccttgaa atccatgacg cagggagaat tgcgtcattt    1800
aaagcctagt taacgcattt actaaacgca gacgaaaatg gaaagattaa ttgggagtgg    1860
taggatgaaa caatttggag aagatagaag tttgaagtgg aaaactggaa gacagaagta    1920
cgggaaggcg aagaaaagaa tagagaagat agggaaatta aagataaaa acatactttt     1980 agaagaaaaa agataaattt aaacctgaaa agtaggaagc agaagaaaaa agacaagcta    2040
ggaaacaaaa agctaagggc aaaatgtaca aacttagaag aaaattggaa gatagaaaca    2100
agatagaaaa tgaaaatatt gtcaagagtt tcagatagaa aatgaaaaac aagctaagac    2160
aagtattgga gaagtataga agatagaaaa atataaagcc aaaaattgga taaaatagca    2220
ctgaaaaaat gaggaaatta ttggtaacca atttatttta aaagcccatc aatttaattt    2280
ctggtggtgc agaagttaga aggtaaagct tgagaagatg agggtgttta cgtagaccag    2340
aaccaattta gaagaatact tgaagctaga aggggaagtt ggttaaaaat cacatcaaaa    2400
agctactaaa aggactggtg taatttaaaa aaaactaagg cagaaggctt ttggaagagt    2460
tagaagaatt tggaaggcct taaatatagt agcttagttt gaaaaatgtg aaggactttc    2520
gtaacggaag taattcaaga tcaagagtaa ttaccaactt aatgtttttg cattggactt    2580
tgagttaaga ttatttttta aatcctgagg actagcatta attgacagct gacccaggtg    2640
ctacacagaa gtggattcag tgaatctagg aagacagcag cagacaggat tccaggaacc    2700
agtgtttgat gaagctagga ctgaggagca agcgagcaag cagcagttcg tggtgaagat    2760
aggaaaagag tccaggagcc agtgcgattt ggtgaaggaa gctaggaaga aggaaggagc    2820
gctaacgatt tggtggtgaa gctaggaaaa aggattccag gaaggagcga gtgcaatttg    2880
gtgatgaagg tagcaggcgg cttggcttgg caaccacacg gaggaggcga gcaggcgttg    2940
tgcgtagagc atcctagacc agcatgccag tgtgccaagg ccacagggaa agcgagtggt    3000
tggtaaaaat ccgtgaggtc ggcaatatgt tgttttctg gaacttactt atggtaacct     3060 tttattatt ttctaatata atgggggagt ttcgtactga ggtgtaaagg gatttatatg     3120
gggacgtagg ccgatttccg ggtgttgtag gtttctcttt ttcaggctta tactcatgaa    3180
tcttgtctga agcttttgag ggcagactgc caagtcctgg agaaatagta gatggcaagt    3240
ttgtgggttt tttttttta cacgaatttg aggaaaacca aatgaatttg atagccaaat    3300
tgagacaatt tcagcaaatc tgtaagcagt ttgtatgttt agttggggta atgaagtatt    3360
tcagttttgt gaatagatga cctgttttta cttcctcacc ctgaattcgt tttgtaaatg    3420
tagagtttgg atgtgtaact gaggcggggg ggagttttca gtattttttt ttgtgggggt    3480
gggggcaaaa tatgttttca gttctttttc ccttaggtct gtctagaatc ctaaaggcaa    3540
```

```
atgactcaag gtgtaacaga aaacaagaaa atccaatatc aggataatca gaccaccaca    3600
ggtttacagt ttatagaaac tagagcagtt ctcacgttga ggtctgtgga agagatgtcc    3660
attggagaaa tggctggtag ttactctttt ttccccccac ccccttaatc agactttaaa    3720
agtgcttaac cccttaaact tgttattttt tacttgaagc attttgggat ggtcttaaca    3780
gggaagagag agggtggggg agaaaatgtt tttttctaag attttccaca gatgctatag    3840
tactattgac aaactgggtt agagaaggag tgtaccgctg tgctgttggc acgaacacct    3900
tcagggactg gagctgcttt tatccttgga agagtattcc cagttgaagc tgaaaagtac    3960
agcacagtgc agctttggtt catattcagt catctcagga gaacttcaga agagcttgag    4020
taggccaaat gttgaagtta agttttccaa taatgtgact tcttaaaagt tttattaaag    4080
gggaggggca aatattggca attagttggc agtggcctgt tacggttggg attggtgggg    4140
tgggtttagg taattgttta gtttatgatt gcagataaac tcatgccaga gaacttaaag    4200
tcttagaatg gaaaaagtaa agaaatatca acttccaagt tggcaagtaa ctcccaatga    4260
tttagttttt ttccccccag tttgaattgg gaagctgggg gaagttaaat atgagccact    4320
gggtgtacca gtgcattaat ttgggcaagg aaagtgtcat aatttgatac tgtatctgtt    4380
ttccttcaaa gtatagagct tttggggaag gaaagtattg aactgggggt tggtctggcc    4440
tactgggctg acattaacta caattatggg aaatgcaaaa gttgtttgga tatggtagtg    4500
tgtggttctc ttttggaatt ttttcaggt gatttaataa taatttaaaa ctactataga    4560
aactgcagag caaggaagt ggcttaatga tcctgaaggg atttcttctg atggtagctt    4620
ttgtattatc aagtaagatt ctatttcag ttgtgtgtaa gcaagttttt ttttagtgta    4680
ggagaaatac ttttccattg tttaactgca aacaagatg ttaaggtatg cttcaaaaat    4740
tttgtaaatt gtttattta aacttatctg tttgtaaatt gtaactgatt aagaattgtg    4800
atagttcagc ttgaatgtct cttagagggt gggcttttgt tgatgaggga ggggaaactt    4860
ttttttttc tatagacttt tttcagataa catcttctga gtcataacca gcctggcagt    4920
atgatggcct agatgcagag aaaacagctc cttggtgaat tgataagtaa aggcagaaaa    4980
gattatatgt catacctcca ttggggaata agcataaccc tgagattctt actactgatg    5040
agaacattat ctgcatatgc caaaaaattt taagcaaatg aaagctacca atttaaagtt    5100
acggaatcta ccattttaaa gttaattgct tgtcaagcta taaccacaaa ataatgaat    5160
tgatgagaaa tacaatgaag aggcaatgtc catctcaaaa tactgctttt acaaaagcag    5220
aataaaagcg aaaagaaatg aaaatgttac actacattaa tcctggaata aaagaagccg    5280
aaataaatga gagatgagtt gggatcaagt ggattgagga ggctgtgctg tgtgccaatg    5340
tttcgtttgc ctcagacagg tatctcttcg ttatcagaag agttgcttca tttcatctgg    5400
gagcagaaaa cagcaggcag ctgttaacag ataagtttaa cttgcatctg cagtattgca    5460
tgttagggat aagtgcttat ttttaagagc tgtggagttc ttaaatatca accatggcac    5520
tttctcctga ccccttccct aggggatttc aggattgaga aattttttcca tcgagccttt    5580
ttaaaattgt aggacttgtt cctgtgggct tcagtgatgg gatagtacac ttcactcaga    5640
ggcatttgca tctttaaata atttcttaaa agcctctaaa gtgatcagtg ccttgatgcc    5700
aactaaggaa atttgtttag cattgaatct ctgaaggctc tatgaaagga atagcatgat    5760
gtgctgttag aatcagatgt tactgctaaa atttacatgt tgtgatgtaa attgtgtaga    5820
aaaccattaa atcattcaaa ataataaact attttttatta gagaatgtat acttttagaa    5880
```

```
agctgtctcc ttatttaaat aaaatagtgt ttgtctgtag ttcagtgttg gggcaatctt   5940
gggggggatt cttctctaat cttttcagaaa ctttgtctgc gaacactctt taatggacca   6000
gatcaggatt tgagcggaag aacgaatgta actttaaggc aggaaagaca aattttattc   6060
ttcataaagt gatgagcata taataattcc aggcacatgg caatagaggc cctctaaata   6120
aggaataaat aacctcttag acaggtggga gattatgatc agagtaaaag gtaattacac   6180
attttatttc cagaaagtca ggggtctata aattgacagt gattagagta atacttttc    6240 acatttccaa agtttgcatg ttaactttaa atgcttacaa tcttagagtg gtaggcaatg   6300
ttttacacta ttgaccttat ataggaagg gaggggtgc ctgtgggtt ttaaagaatt      6360 ttcctttgca gaggcatttc atccttcatg aagccattca ggattttgaa ttgcatatga   6420
gtgcttggct cttccttctg ttctagtgag tgtatgagac cttgcagtga gtttatcagc   6480
atactcaaaa ttttttttcct ggaatttgga gggatgggag gaggggggtgg ggcttacttg  6540 ttgtagcttt ttttttttttt acagacttca cagagaatgc agttgtcttg acttcaggtc  6600
tgtctgttct gttggcaagt aaatgcagta ctgttctgat cccgctgcta ttagaatgca   6660
ttgtgaaacg actggagtat gattaaaagt tgtgttcccc aatgcttgga gtagtgattg   6720
ttgaaggaaa aaatccagct gagtgataaa ggctgagtgt tgaggaaatt tctgcagttt   6780
taagcagtcg tatttgtgat tgaagctgag tacattttgc tggtgtattt ttaggtaaaa   6840 tgcttttttgt tcatttctgg tggtgggagg ggactgaagc ctttagtctt ttccagatgc   6900
aaccttaaaa tcagtgacaa gaaacattcc aaacaagcaa cagtcttcaa gaaattaaac   6960
tggcaagtgg aaatgtttaa acagttcagt gatctttagt gcattgttta tgtgtgggtt   7020
tctctctccc ctcccttggt cttaattctt acatgcagga acactcagca gacacacgta   7080
tgcgaagggc cagagaagcc agacccagta agaaaaaata gcctatttac tttaaataaa   7140
ccaaacattc cattttaaat gtggggattg ggaaccacta gttctttcag atggtattct   7200
tcagactata gaaggagctt ccagttgaat tcaccagtgg acaaaatgag gaaaacaggt   7260
gaacaagctt tttctgtatt tacatacaaa gtcagatcag ttatgggaca atagtattga   7320
atagatttca gctttatgct ggagtaactg gcatgtgagc aaactgtgtt ggcgtggggg   7380 tggagggggtg aggtgggcgc taagcctttt tttaagattt ttcaggtacc cctcactaaa   7440
ggcaccgaag gcttaaagta ggacaaccat ggagccttcc tgtggcagga gagacaacaa   7500
agcgctatta tcctaaggtc aagagaagtg tcagcctcac ctgattttta ttagtaatga   7560
ggacttgcct caactccctc tttctggagt gaagcatccg aaggaatgct tgaagtaccc   7620
ctgggcttct cttaacatttt aagcaagctg tttttatagc agctcttaat aataaagccc   7680
aaatctcaag cggtgcttga agggaggga aaggggaaa gcgggcaacc acttttccct     7740
agcttttcca gaagcctgtt aaaagcaagg tctccccaca agcaacttct ctgccacatc   7800
gccaccccgt gccttttgat ctagcacaga cccttcaccc ctcacctcga tgcagccagt   7860
agcttggatc cttgtgggca tgatccataa tcggtttcaa ggtaacgatg gtgtcgaggt   7920
ctttggtggg ttgaactatg ttagaaaagg ccattaattt gcctgcaaat tgttaacaga   7980
agggtattaa aaccacagct aagtagctct attataatac ttatccagtg actaaaacca   8040 acttaaaacca gtaagtggag aaataacatg ttcaagaact gtaatgctgg gtgggaacat   8100
gtaacttgta gactggagaa gataggcatt tgagtggctg agagggcttt tgggtgggaa   8160
tgcaaaaatt ctctgctaag acttttttcag gtgaacataa cagacttggc caagctagca   8220
tcttagcgga agctgatctc caatgctctt cagtagggtc atgaaggttt ttcttttcct   8280
```

```
gagaaaacaa cacgtattgt tttctcaggt tttgcttttt ggccttttc tagcttaaaa    8340 aaaaaaaaag caaagatgc tggtggttgg cactcctggt ttccaggacg gggttcaaat    8400
ccctgcggcg tctttgcttt gactactaat ctgtcttcag gactctttct gtatttctcc    8460
ttttctctgc aggtgctagt tcttggagtt ttggggaggt gggaggtaac agcacaatat    8520
ctttgaacta tatacatcct tgatgtataa tttgtcagga gcttgacttg attgtatatt    8580
catatttaca cgagaaccta atataactgc cttgtctttt tcaggtaata gcctgcagct    8640
ggtgttttga gaagccctac tgctgaaaac ttaacaattt tgtgtaataa aaatggagaa    8700
gctctaaatt gttgtggttc ttttgtgaat aaaaaatct tgattgggga aaaaaaaa      8758
```

```
<210> SEQ ID NO 7
<211> LENGTH: 13
<212> TYPE: DNA
<213> ORGANISM: Artificial
<220> FEATURE:
<223> OTHER INFORMATION: Synthetic

<400> SEQUENCE: 7
ctaggtcatg cgt                                                       13

<210> SEQ ID NO 8
<211> LENGTH: 17
<212> TYPE: DNA
<213> ORGANISM: Artificial
<220> FEATURE:
<223> OTHER INFORMATION: Synthetic

<400> SEQUENCE: 8
ctaggtcatg ttttcgt                                                   17

<210> SEQ ID NO 9
<211> LENGTH: 9
<212> TYPE: DNA
<213> ORGANISM: Artificial
<220> FEATURE:
<223> OTHER INFORMATION: Synthetic

<400> SEQUENCE: 9 ctaggtcgt                                                             9

<210> SEQ ID NO 10
<211> LENGTH: 5
<212> TYPE: DNA
<213> ORGANISM: Artificial
<220> FEATURE:
<223> OTHER INFORMATION: Synthetic

<400> SEQUENCE: 10 ctcgt                                                                 5

<210> SEQ ID NO 11
<211> LENGTH: 13
<212> TYPE: DNA
<213> ORGANISM: Artificial
<220> FEATURE:
<223> OTHER INFORMATION: Synthetic

<400> SEQUENCE: 11
gtaggtcatg cgt                                                       13

<210> SEQ ID NO 12
```

-continued

```
<211> LENGTH: 13
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (11)..(13)
<223> OTHER INFORMATION: LNA

<400> SEQUENCE: 12
gtattgctga gga                                                          13

<210> SEQ ID NO 13
<211> LENGTH: 13
<212> TYPE: RNA
<213> ORGANISM: Artificial
<220> FEATURE:
<223> OTHER INFORMATION: Synthetic

<400> SEQUENCE: 13
uccucagcaa uac                                                          13

<210> SEQ ID NO 14
<211> LENGTH: 13
<212> TYPE: DNA
<213> ORGANISM: Artificial
<220> FEATURE:
<223> OTHER INFORMATION: Synthetic

<400> SEQUENCE: 14
tcctcagcaa tac                                                          13

<210> SEQ ID NO 15
<211> LENGTH: 12
<212> TYPE: RNA
<213> ORGANISM: Artificial
<220> FEATURE:
<223> OTHER INFORMATION: Synthetic

<400> SEQUENCE: 15
uccucagcaa ua                                                           12

<210> SEQ ID NO 16
<211> LENGTH: 11
<212> TYPE: RNA
<213> ORGANISM: Artificial
<220> FEATURE:
<223> OTHER INFORMATION: Synthetic

<400> SEQUENCE: 16
uccucagcaa u                                                            11

<210> SEQ ID NO 17
<211> LENGTH: 10
<212> TYPE: RNA
<213> ORGANISM: Artificial
<220> FEATURE:
<223> OTHER INFORMATION: Synthetic

<400> SEQUENCE: 17
uccucagcaa                                                              10
```

```
<210> SEQ ID NO 18
<211> LENGTH: 26
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (14)..(26)
<223> OTHER INFORMATION: RNA

<400> SEQUENCE: 18
ctaggtcatg cgtuccucag caauac                                    26

<210> SEQ ID NO 19
<211> LENGTH: 30
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (15)..(17)
<223> OTHER INFORMATION: LNA
<220> FEATURE:
<221> NAME/KEY: misc_feature
<222> LOCATION: (18)..(30)
<223> OTHER INFORMATION: RNA

<400> SEQUENCE: 19
ctaggtcatg ttttcgtucc ucagcaauac                                30

<210> SEQ ID NO 20
<211> LENGTH: 22
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (7)..(9)
<223> OTHER INFORMATION: LNA
<220> FEATURE:
<221> NAME/KEY: misc_feature
<222> LOCATION: (10)..(22)
<223> OTHER INFORMATION: RNA

<400> SEQUENCE: 20
ctaggtcgtu ccucagcaau ac                                        22

<210> SEQ ID NO 21
```

```
<211> LENGTH: 18
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(5)
<223> OTHER INFORMATION: LNA
<220> FEATURE:
<221> NAME/KEY: misc_feature
<222> LOCATION: (6)..(18)
<223> OTHER INFORMATION: RNA

<400> SEQUENCE: 21
ctcgtuccuc agcaauac                                         18

<210> SEQ ID NO 22
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (14)..(16)
<223> OTHER INFORMATION: LNA

<400> SEQUENCE: 22
atagtcactc tggtga                                           16

<210> SEQ ID NO 23
<211> LENGTH: 16
<212> TYPE: RNA
<213> ORGANISM: Artificial
<220> FEATURE:
<223> OTHER INFORMATION: Synthetic

<400> SEQUENCE: 23
ucaccagagu gacuau                                           16

<210> SEQ ID NO 24
<211> LENGTH: 29
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (14)..(29)
<223> OTHER INFORMATION: RNA

<400> SEQUENCE: 24
gtaggtcatg cgtucaccag agugacuau                             29

<210> SEQ ID NO 25
<211> LENGTH: 26
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
```

```
<222> LOCATION: (1)..(2)
<223> OTHER INFORMATION: LNA
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (14)..(24)
<223> OTHER INFORMATION: RNA
<220> FEATURE:
<221> NAME/KEY: misc_feature
<222> LOCATION: (25)..(26)
<223> OTHER INFORMATION: 2'-O-Me RNA

<400> SEQUENCE: 25
gtaggtcatg cgtuccucag caauac                                          26

<210> SEQ ID NO 26
<211> LENGTH: 13
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (11)..(13)
<223> OTHER INFORMATION: LNA

<400> SEQUENCE: 26
ctaggtcatg cgt                                                        13

<210> SEQ ID NO 27
<211> LENGTH: 26
<212> TYPE: DNA
<213> ORGANISM: Artificial
<220> FEATURE:
<223> OTHER INFORMATION: Synthetic
<220> FEATURE:
<223> OTHER INFORMATION: DNA/RNA molecule
<220> FEATURE:
<221> NAME/KEY: misc_feature
<222> LOCATION: (1)..(2)
<223> OTHER INFORMATION: LNA
<220> FEATURE:
<221> NAME/KEY: misc_feature
<222> LOCATION: (11)..(13)
<223> OTHER INFORMATION: LNA
<220> FEATURE:
<221> NAME/KEY: misc_feature
<222> LOCATION: (14)..(24)
<223> OTHER INFORMATION: RNA
<220> FEATURE:
<221> NAME/KEY: misc_feature
<222> LOCATION: (25)..(26)
<223> OTHER INFORMATION: 2'-O-Me RNA

<400> SEQUENCE: 27
gtattgctga ggaacgcaug accuag                                          26

<210> SEQ ID NO 28
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3)
```

```
<223> OTHER INFORMATION: LNA
<220> FEATURE:
<221> NAME/KEY: misc_feature
<222> LOCATION: (14)..(16)
<223> OTHER INFORMATION: LNA

<400> SEQUENCE: 28
ctagttcact gaatgc                                                         16

<210> SEQ ID NO 29
<211> LENGTH: 16
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-O-Me RNA
<220> FEATURE:
<221> NAME/KEY: misc_feature
<222> LOCATION: (14)..(16)
<223> OTHER INFORMATION: 2'-O-Me RNA

<400> SEQUENCE: 29
gcauucagug aacuag                                                         16

<210> SEQ ID NO 30
<211> LENGTH: 16
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3)
<223> OTHER INFORMATION: LNA
<220> FEATURE:
<221> NAME/KEY: misc_feature
<222> LOCATION: (14)..(16)
<223> OTHER INFORMATION: LNA

<400> SEQUENCE: 30
agtactatag catctg                                                         16

<210> SEQ ID NO 31
<211> LENGTH: 16
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-O-Me RNA
<220> FEATURE:
<221> NAME/KEY: misc_feature
<222> LOCATION: (14)..(16)
<223> OTHER INFORMATION: 2'-O-Me RNA

<400> SEQUENCE: 31
cagaugcuau aguacu                                                         16

<210> SEQ ID NO 32
<211> LENGTH: 13
<212> TYPE: DNA
<213> ORGANISM: Artificial
<220> FEATURE:
<223> OTHER INFORMATION: Synthetic
<220> FEATURE:
<221> NAME/KEY: misc_feature
```

```
<222> LOCATION: (2)..(2)
<223> OTHER INFORMATION: LNA
<220> FEATURE:
<221> NAME/KEY: misc_feature
<222> LOCATION: (4)..(4)
<223> OTHER INFORMATION: LNA
<220> FEATURE:
<221> NAME/KEY: misc_feature
<222> LOCATION: (6)..(6)
<223> OTHER INFORMATION: LNA
<220> FEATURE:
<221> NAME/KEY: misc_feature
<222> LOCATION: (8)..(8)
<223> OTHER INFORMATION: LNA
<220> FEATURE:
<221> NAME/KEY: misc_feature
<222> LOCATION: (10)..(10)
<223> OTHER INFORMATION: LNA
<220> FEATURE:
<221> NAME/KEY: misc_feature
<222> LOCATION: (12)..(12)
<223> OTHER INFORMATION: LNA

<400> SEQUENCE: 32
aacctcggct tac                                                          13

<210> SEQ ID NO 33
<211> LENGTH: 13
<212> TYPE: RNA
<213> ORGANISM: Artificial
<220> FEATURE:
<223> OTHER INFORMATION: Synthetic
<220> FEATURE:
<221> NAME/KEY: misc_feature
<222> LOCATION: (1)..(3)
<223> OTHER INFORMATION: 2'-O-Me RNA
<220> FEATURE:
<221> NAME/KEY: misc_feature
<222> LOCATION: (11)..(13)
<223> OTHER INFORMATION: 2'-O-Me RNA

<400> SEQUENCE: 33
guaagccgag guu                                                          13
```

NUCLEIC ACID WITH REDUCED TOXICITY

CROSS-REFERENCE TO RELATED APPLICATIONS

This application is a 371 of PCT/JP2019/011464, filed Mar. 19, 2019, which claims the benefit of Japanese Patent Application No. 2018-051338, filed Mar. 19, 2018.

TECHNICAL FIELD

The present invention relates to a low toxicity antisense nucleic acid medicine that can modulate expression of a target transcriptional product. More specifically, this invention relates to a low toxicity antisense nucleic acid medicine that can modulate expression of a target transcriptional product in the central nervous system and other sites of a subject.

BACKGROUND ART

In recent years, an oligonucleotide has been drawing attention in the ongoing development of pharmaceuticals called nucleic acid medicines, and in particular, development of a nucleic acid medicine utilizing the antisense method is actively pushed forward from the viewpoint of e.g., high selectivity to target genes. The antisense method includes a method of selectively modifying or inhibiting expression of a protein encoded by a target gene by introducing an oligonucleotide complementary to a partial sequence of mRNA (sense strand) of the target gene (e.g., antisense oligonucleotide, i.e., ASO) into a cell. Similarly, an antisense method also targets a miRNA and functions to modify the activity of such a miRNA.

As a nucleic acid utilizing the antisense method, the present inventors have developed a double-stranded nucleic acid complex (heteroduplex oligonucleotide, HDO) formed by annealing an antisense oligonucleotide and a complementary strand thereto (Patent Literature 1, Non Patent Literatures 1 and 2). The inventors have also developed a double-stranded antisense nucleic acid (Patent Literature 2) having an exon skipping effect, a short gapmer-antisense oligonucleotide, in which an additional nucleotide is added to the 5' end, the 3' end, or both the 5' end and the 3' end of a gapmer (antisense oligonucleotide) (Patent Literature 3), and a double-stranded agent (hetero-chimera-duplex oligonucleotide, HCDO) for delivering a therapeutic oligonucleotide (Patent Literature 4).

Nusinersen is an antisense nucleic acid medicine for intrathecal administration for the treatment of spinal muscular atrophy, which is approved in the United States in December 2016. Nusinersen is a chemically modified nucleic acid in which the 2' position of the sugar moiety of a nucleic acid is replaced with 2'-O-(2-methoxyethyl) (2'-MOE). Spinal muscular atrophy is caused by an inactivating mutation in the SMN1 gene coding for a survival motor neuron (SMN) protein, while nusinersen modulates alternative splicing of the SMN2 gene to change it into the SMN1 gene, increases the amount of the survival motor neuron protein in the central nervous system, and thereby improves the symptoms of spinal muscular atrophy (Patent Literature 5). However, in some cases nusinersen causes side effects such as various neurotoxicities when administered intrathecally. It is expected that the development of chemically modified nucleic acid medicines for the treatment of neurological diseases by intrathecal administration as in the case of nusinersen will be the mainstream of future drug development. However, for this purpose, it is necessary to decrease possible side effects (toxicity) which may occur in administration into the central nervous system to improve the safety.

CITATION LIST

Patent Literature

Patent Literature 1: International Publication No. WO 2013/089283
Patent Literature 2: International Publication No. WO 2014/203518
Patent Literature 3: International Publication No. WO 2014/132671
Patent Literature 4: International Publication No. WO 2014/192310
Patent Literature 5: International Publication No. WO 2010/148249
Patent Literature 6: PCT/JP2017/035553
Patent Literature 7: PCT/JP2017/034561

Non Patent Literature

Non Patent Literature 1: Nishina K, et al., "DNA/RNA heteroduplex oligonucleotide for highly efficient gene silencing", Nature Communication, 2015, 6: 7969.
Non Patent Literature 2: Asami Y, et al., "Drug delivery system of therapeutic oligonucleotides", Drug Discoveries & Therapeutics, 2016; 10(5): 256-262.

SUMMARY OF INVENTION

Technical Problem

An object of the present invention is to provide a low toxicity antisense nucleic acid medicine that can modulate expression of a target transcriptional product in the central nervous system and other sites of a subject.

Solution to Problem

To achieve the above object, the present inventors have studied intensively and found that when an antisense oligonucleotide is administered as part of a nucleic acid complex having a double-stranded structure to a subject, an antisense effect can be obtained in the central nervous system and other sites with low toxicity and expression of a target transcriptional product can be modulated, and eventually completed the invention.

That is, the present invention encompasses the following.

[1] A low toxicity composition for administration to a central nervous system for modulating expression of a target transcriptional product in the central nervous system of a subject, comprising a nucleic acid complex formed by annealing together a first nucleic acid strand comprising an antisense oligonucleotide region with respect to the target transcriptional product, and a second nucleic acid strand comprising a complementary region that is complementary to at least part of the first nucleic acid strand.

[2] The composition according to [1], wherein the toxicity is neurotoxicity.

[3] The composition according to [2], wherein the neurotoxicity produces a symptom selected from death, breathing abnormality, cardiovascular abnormality, headache, nausea or vomiting, unresponsiveness or low responsiveness, impaired consciousness, mental disorder, personality change, hallucination, delusion, cognitive dysfunction, abnormal posture, involuntary movement, tremor, convulsion, hyperactivity, disturbance of motor function, paralysis, sensory abnormality, and autonomic nervous system dysfunction.

[4] The composition according to any one of [1] to [3], wherein the first nucleic acid strand is 9 to 50 base in length.

[5] The composition according to any one of [1] to [4], wherein said antisense oligonucleotide region in the first nucleic acid strand is 7 to 20 base in length.

[6] The composition according to any one of [1] to [5], wherein the second nucleic acid strand is 9 to 50 base in length.

[7] The composition according to any one of [1] to [6], wherein said complementary region in the second nucleic acid strand is complementary to at least part of said antisense oligonucleotide region in the first nucleic acid strand.

[8] The composition according to any one of [1] to [7], wherein the first nucleic acid strand is a nucleic acid strand comprising: (a) at least four contiguous DNA nucleotides or modified DNA nucleotides recognized by RNase H when hybridized to said transcriptional product, and further comprising: (b) a 5' wing region comprising one or multiple modified nucleotides placed on the 5' end side of said at least four contiguous DNA nucleotides or modified DNA nucleotides recognized by RNase H; and/or (c) a 3' wing region comprising one or multiple modified nucleotides placed on the 3' end side of said at least four contiguous DNA nucleotides or modified DNA nucleotides recognized by RNase H.

[9] The composition according to any one of [1] to [8], wherein the second nucleic acid strand is a nucleic acid strand comprising (a) at least four contiguous RNA nucleosides, and further comprising: (b) one or multiple modified nucleotides placed on the 5' end side of said at least four contiguous RNA nucleosides, and/or (c) one or multiple modified nucleotides placed on the 3' end side of said at least four contiguous RNA nucleosides.

[10] The composition according to any one of [7] to [9], wherein the second nucleic acid strand further comprises at least one overhanging region located on one or both of the 5' end side and the 3' end side of said complementary region.

[11] The composition according to [10], wherein the overhanging region in the second nucleic acid strand is at least 5 base in length.

[12] The composition according to any one of [1] to [6], wherein the first nucleic acid strand further comprises a complementary RNA region, and said complementary RNA region has at least two contiguous RNA nucleotides that can be recognized by RNase H when the first nucleic acid strand is hybridized with the second nucleic acid strand, said complementary region in the second nucleic acid strand is a complementary DNA region, and said complementary DNA region can hybridize with the complementary RNA region in the first nucleic acid strand to promote the recognition of at least two contiguous RNA nucleotides in the first nucleic acid strand by RNase H, and further said antisense oligonucleotide region in the first nucleic acid strand cannot hybridize with the second nucleic acid strand.

[13] The composition according to any one of [1] to [12] wherein the administration to the central nervous system is intrathecal administration or intraventricular administration.

[14] The composition according to any one of [1] to [13], wherein the expression modulation of the target transcriptional product is reduction of the amount of the target transcriptional product.

[15] The composition according to any one of [1] to [14] for treating a central nervous system disease.

[16] The composition according to any one of [1] to [15], wherein the antisense oligonucleotide region is a gapmer type antisense oligonucleotide region, or a mixmer type antisense oligonucleotide region.

[17] The composition according to any one of [1] to [16], wherein the antisense oligonucleotide region comprises an LNA nucleoside.

[18] Use of a nucleic acid strand comprising a complementary region that is complementary to at least part of an antisense oligonucleotide for reducing the toxicity of the antisense oligonucleotide.

[19] A method for administering a low toxicity antisense nucleic acid medicine to the central nervous system of a subject comprising a step of administering the composition according to any one of [1] to [17] to the central nervous system of a subject.

[20] The method according to [19], which is a method for treating a central nervous system disease of a subject.

[21] A method for producing a low toxicity antisense nucleic acid medicine comprising (i) a step of preparing a first nucleic acid strand comprising an antisense oligonucleotide region with respect to a target transcriptional product; (ii) a step of preparing a second nucleic acid strand comprising a complementary region that is complementary to at least part of the first nucleic acid strand; (iii) a step of forming a nucleic acid complex by annealing together the first nucleic acid strand and the second nucleic acid strand; and (iv) a step of preparing an antisense nucleic acid medicine containing the nucleic acid complex.

[22] A low toxicity composition for modulating expression of a target transcriptional product in a subject, comprising a nucleic acid complex formed by annealing together a first nucleic acid strand comprising an antisense oligonucleotide region with respect to the target transcriptional product, and a second nucleic acid strand comprising a complementary region that is complementary to at least part of the first nucleic acid strand.

[23] The composition according to [22], wherein the toxicity is neurotoxicity or nephrotoxicity.

[24] The composition according to [22] or [23] for intravenous administration or subcutaneous administration.

This description encompasses the disclosures of Japanese Patent Application No. 2018-051338, which is the basis for the priority of the present application.

Advantageous Effects of Invention

The present invention provides a low toxicity antisense nucleic acid medicine that can modulate expression of a target transcriptional product in a subject.

BRIEF DESCRIPTION OF DRAWINGS

FIGS. 1(a) and (b) are each a schematic diagram showing an example of a basic configuration of a specific embodiment of a nucleic acid complex according to the present invention.

FIG. 10 shows schematic diagrams of the structures of the nucleic acids used in Example 4.

FIG. 15 shows schematic diagrams of the structures of the nucleic acids used in Example 9. The "Toc" indicates tocopherol.

DESCRIPTION OF EMBODIMENTS

The present invention is described in detail below.
<Nucleic Acid Complex>

The present invention uses a nucleic acid complex in which a first nucleic acid strand and a second nucleic acid strand comprising (or consisting of) a complementary region that is complementary to at least part of the first nucleic acid strand are annealed via hydrogen bonds of complementary base pairs. The nucleic acid complex has a double-stranded structure produced by the annealing of the first nucleic acid strand with the second nucleic acid strand. It is not necessary that all of the first nucleic acid strand and all of the second nucleic acid strand are annealed, rather part of the first nucleic acid strand and all of the second nucleic acid strand may be annealed, or all of the first nucleic acid strand and part of the second nucleic acid strand may be annealed. Alternatively, part of the first nucleic acid strand and part of the second nucleic acid strand may be annealed.

The first nucleic acid strand is a nucleotide strand comprising or consisting of an antisense oligonucleotide region with respect to a target transcriptional product. An "antisense oligonucleotide" or an "antisense nucleic acid" means a single-stranded oligonucleotide which comprises a base sequence that is capable of hybridizing (namely complementary) to at least part of a target transcriptional product (mainly a transcriptional product of a target gene), and is able to produce an antisense effect on a target transcriptional product. According to the present invention, the antisense oligonucleotide region in the first nucleic acid strand can produce an antisense effect on a target transcriptional product.

Figure 5:
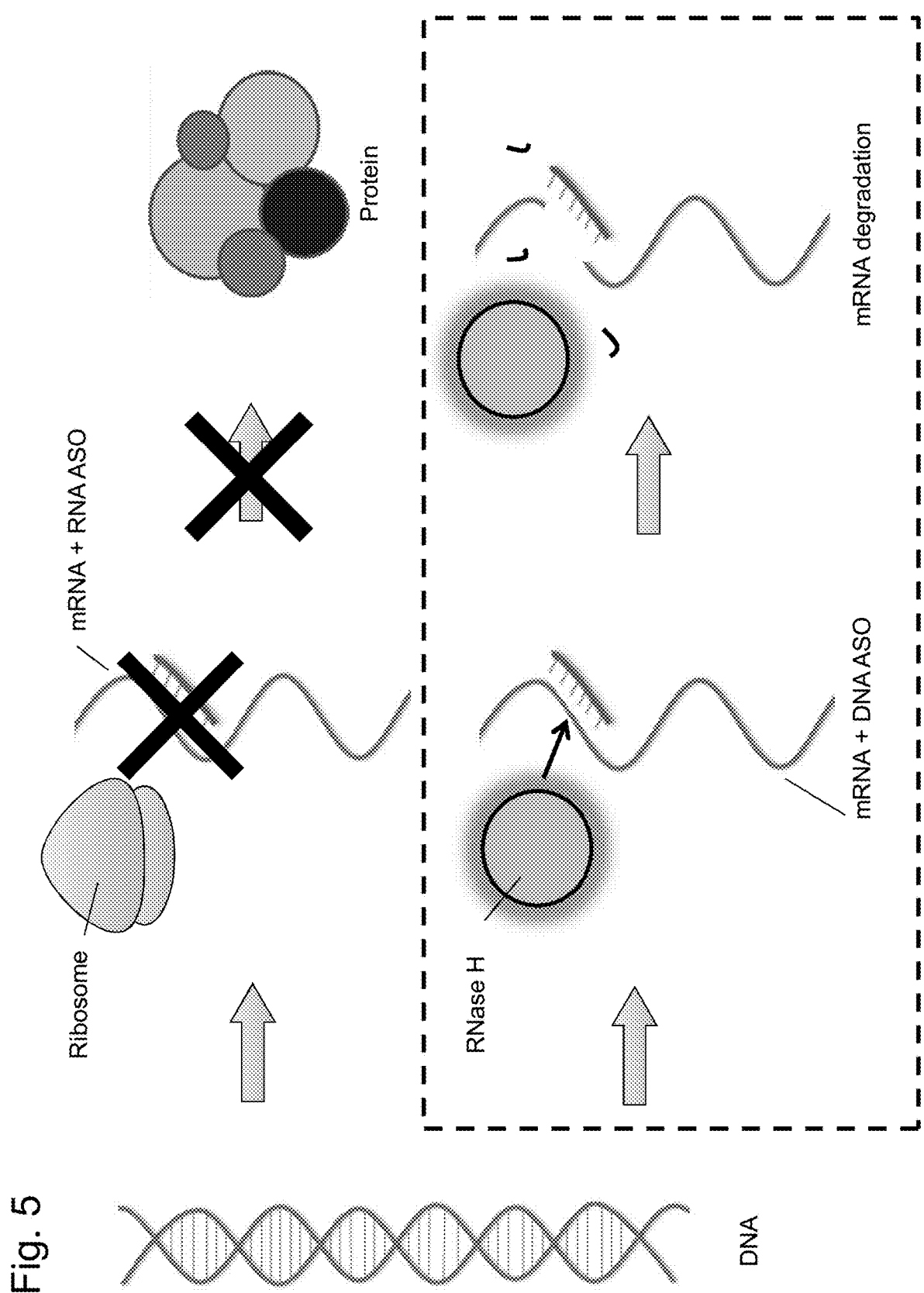
FIG. 5 is a diagram showing an example of a general mechanism of the antisense method.

An "antisense effect" means the modulation of expression of a target transcriptional product, which results from hybridization of the target transcriptional product (RNA-sense strand) with a strand (e.g., DNA strand) that is complementary to a partial sequence of a transcriptional product or the like, and designed to produce an antisense effect. The modulation of expression of a target transcriptional product includes inhibition or reduction of expression of a target gene, or the level (expression amount) of a target transcriptional product, or in a certain example inhibition of translation or inhibitory effect on nucleic acid-protein binding, for example splicing function modification effect, for example, exon skipping, or degradation of a transcriptional product (see FIG. 5). For example, in inhibition of translation, when an oligonucleotide comprising RNA is introduced into a cell as an antisense oligonucleotide (ASO), the ASO binds to a transcriptional product (mRNA) of the target gene to form a partial double strand. This partial double strand serves as a cover to prevent translation by a ribosome, thus expression of a protein encoded by the target gene is inhibited on the translational level (FIG. 5, x marks outside the dashed line). Meanwhile, when an oligonucleotide comprising DNA is introduced into a cell as ASO, a partial DNA-RNA heteroduplex is formed. This heteroduplex structure is recognized by RNase H, and as a result the mRNA of the target gene is degraded, and consequently expression of the protein encoded by the target gene is inhibited on the expression level (FIG. 5, inside the dashed line). This is called "RNase H-dependent pathway". Further, in a certain example, an antisense effect may also be brought about by targeting an intron of a mRNA precursor. An antisense effect may also be brought about by targeting miRNA, and in this case the function of the miRNA is inhibited, and expression of a gene whose expression is normally regulated by the miRNA may increase. In an embodiment, the modulation of expression of a target transcriptional product may be reduction of the amount of the target transcriptional product.

Although there is no particular restriction on the "target gene" whose expression is modulated (for example, suppressed, altered, or modified) by an antisense effect, examples thereof include a gene derived from an organism to which a nucleic acid complex of the invention is introduced, such as a gene whose expression increases in a variety of diseases. Further, a "transcriptional product of a target gene" is a mRNA transcribed from the genomic DNA encoding the target gene, and also includes a mRNA without a base modification, an unprocessed mRNA precursor, or the like. A "target transcriptional product" may include not only a mRNA, but also a non-coding RNA (ncRNA) such as a miRNA. Further, in general, a transcriptional product may be any RNA synthesized by a DNA-dependent RNA polymerase.

In an embodiment, a "target transcriptional product" may be, for example, β-secretase 1 (BACE1) mRNA, microtubule-associated protein tau (Tau) mRNA, metastasis associated lung adenocarcinoma transcript 1 (MALAT1) non-coding RNA, or dystrophin mRNA. The base sequences of murine and human BACE1 mRNA are shown in SEQ ID NO: 1 and 2 respectively (the base sequence of mRNA is shown as the base sequence of DNA). In addition, the base sequences of murine and human Tau mRNA are shown in SEQ ID NO: 3 and 4 respectively (the base sequence of mRNA is shown as the base sequence of DNA). Further, the base sequences of murine and human MALAT1 non-coding RNA are shown in SEQ ID NO: 5 and 6, respectively (the base sequence of RNA is shown as the base sequence of DNA). The base sequences of genes and transcriptional products are available from public databases, such as the NCBI (U.S. National Center for Biotechnology Information) database.

The antisense oligonucleotide region in the first nucleic acid strand comprises a base sequence that can hybridize to at least part of a target transcriptional product (for example, any target region). The target region may include a 3' UTR, a 5' UTR, an exon, an intron, a coding region, a translation initiation region, a translation termination region, or any other nucleic acid region. The target region of a target transcriptional product may comprise, for example, the base sequence of positions 1569 to 1581 of SEQ ID NO: 1 in the case of murine BACE1 mRNA, the base sequence of positions 3339 to 3354 of SEQ ID NO: 3 in the case of murine Tau mRNA, and the base sequence of positions 1316 to 1331 of SEQ ID NO: 5 in the case of murine MALAT1 non-coding RNA.

The term "nucleic acid" or "nucleic acid molecule" as used herein may refer to a monomer of a nucleotide or a nucleoside, or may mean an oligonucleotide consisting of a plurality of monomers. The term "nucleic acid strand" or "strand" is also used herein to refer to an oligonucleotide. A nucleic acid strand can be produced as a full-length strand, or a partial strand by a chemical synthesis method (for example, with an automated synthesis apparatus) or by an enzymatic process (for example, but not limited to, by a polymerase, ligase, or a restriction reaction).

The term "nucleobase" or "base" as used herein means a base component (heterocyclic moiety) constituting a nucleic acid, and primarily adenine, guanine, cytosine, thymine, and uracil are known.

The term "complementary" as used herein means a relationship in which nucleobases can form so-called Watson-Crick base pairs (natural type base pair), or non-Watson-Crick base pairs (Hoogsteen type base pairs, or the like) via hydrogen bonds. In the present invention, it is not necessarily required that the antisense oligonucleotide region in the first nucleic acid strand is completely complementary to at least a part of a target transcriptional product (e.g., the transcriptional product of a target gene), but it is permitted that the base sequence has a complementarity of at least 70%, preferably at least 80%, and more preferably at least 90% (e.g., 95%, 96%, 97%, 98%, or 99% or more). An antisense oligonucleotide region in the first nucleic acid strand can hybridize to a target transcriptional product, when the base sequences are complementary (typically, when a base sequence is complementary to at least part of the base sequence of the target transcriptional product). Similarly, it is not necessarily required that the complementary region in the second nucleic acid strand is completely complementary to at least part of the first nucleic acid strand, but it is permitted that the base sequence has a complementarity of at least 70%, preferably at least 80%, and more preferably at least 90% (e.g., 95%, 96%, 97%, 98%, or 99% or more). When the base sequence of the complementary region in the second nucleic acid strand is complementary to at least part of the first nucleic acid strand, the region can be annealed thereto. The complementarity of a base sequence can be determined using a BLAST program or the like. One skilled in the art can easily determine the conditions (temperature, salt concentration, etc.) under which the two strands can be annealed or hybridized to each other, taking into account the complementarity between the strands. Further, one skilled in the art can easily design an antisense nucleic acid that is complementary to the target transcriptional product based on, for example, information on the base sequence of a target gene.

Hybridization conditions may include a variety of stringent conditions, such as a low-stringent condition and a high-stringent condition. As for a low-stringent condition, a condition with a relatively low temperature, and a high salt concentration, for example, 30° C., 2×SSC, and 0.1% SDS, may be acceptable. As for a high-stringent condition, a condition with a relatively high temperature, and a low salt concentration, for example, 65° C., 0.1×SSC, and 0.1% SDS, may be acceptable. The stringency of hybridization can be adjusted by varying the conditions, such as temperature and salt concentration. In this regard, 1×SSC contains 150 mM of sodium chloride and 15 mM of sodium citrate.

The antisense oligonucleotide region in the first nucleic acid strand may be usually, but not limited to, at least 7 base in length, at least 8 base in length, at least 9 base in length, at least 10 base in length, at least 11 base in length, at least 12 base in length, or at least 13 base in length. The antisense oligonucleotide region in the first nucleic acid strand may be 35 base in length or less, 30 base in length or less, 25 base in length or less, 24 base in length or less, 23 base in length or less, 22 base in length or less, 21 base in length or less, 20 base in length or less, 19 base in length or less, 18 base in length or less, 17 base in length or less, or 16 base in length or less. The antisense oligonucleotide region in the first nucleic acid strand may be, for example, from 7 to 35 base in length, from 7 to 30 base in length, from 7 to 25 base in length, from 7 to 20 base in length, from 8 to 20 base in length, from 9 to 20 base in length, from 10 to 20 base in length, from 11 to 18 base in length, or from 12 to 16 base in length.

Although there is no particular restriction, the first nucleic acid strand may be at least 7 base in length, at least 8 base in length, at least 9 base in length, at least 10 base in length, at least 11 base in length, at least 12 base in length, or at least 13 base in length. The first nucleic acid strand may be 50 base in length or less, 45 base in length or less, 40 base in length or less, 35 base in length or less, 30 base in length or less, 28 base in length or less, 26 base in length or less, 24 base in length or less, 22 base in length or less, 20 base in length or less, 18 base in length or less, or 16 base in length or less. The first nucleic acid strand may be, for example, from 9 to 50 base in length, from 10 to 40 base in length, from 11 to 35 base in length, or from 12 to 30 base in length.

The complementary region in the second nucleic acid strand may be usually, but not limited to, at least 7 base in length, at least 8 base in length, at least 9 base in length, at least 10 base in length, at least 11 base in length, at least 12 base in length, or at least 13 base in length. The complementary region in the second nucleic acid strand may be 35 base in length or less, 30 base in length or less, 25 base in length or less, 24 base in length or less, 23 base in length or less, 22 base in length or less, 21 base in length or less, 20 base in length or less, 19 base in length or less, 18 base in length or less, 17 base in length or less, or 16 base in length or less. The complementary region in the second nucleic acid strand may be, for example, from 9 to 35 base in length, from 9 to 30 base in length, from 10 to 25 base in length, from 10 to 20 base in length, from 11 to 18 base in length, or from 12 to 16 base in length.

Although there is no particular restriction, the second nucleic acid strand may be at least 7 base in length, at least 8 base in length, at least 9 base in length, at least 10 base in length, at least 11 base in length, at least 12 base in length, or at least 13 base in length. The second nucleic acid strand may be 50 base in length or less, 45 base in length or less, 40 base in length or less, 35 base in length or less, 30 base in length or less, 28 base in length or less, 26 base in length or less, 24 base in length or less, 22 base in length or less, 20 base in length or less, 18 base in length or less, or 16 base in length or less. The second nucleic acid strand may be, for example, from 9 to 50 base in length, from 10 to 40 base in length, from 11 to 35 base in length, or from 12 to 30 base in length. The length is generally selected especially according to the balance between the strength of the antisense effect and the specificity of the nucleic acid strand with respect to the target among other factors, such as cost, and synthesis yield.

The second nucleic acid strand comprises or consists of a complementary region that is complementary to at least part of the first nucleic acid strand.

In an embodiment, the complementary region in the second nucleic acid strand can be complementary to at least part of the antisense oligonucleotide region in the first nucleic acid strand. The complementary region in the second nucleic acid strand may be complementary to all of the antisense oligonucleotide region in the first nucleic acid strand. The complementary region in the second nucleic acid strand may be complementary additionally to a part of the first nucleic acid strand other than the antisense oligonucleotide region. An example of this embodiment is a heteroduplex oligonucleotide (HDO) disclosed in International Publication No. WO 2013/089283.

In an embodiment, the second nucleic acid strand consisting of a complementary region may have the same length as the first nucleic acid strand consisting of an antisense oligonucleotide region (FIG. 1(a)), or shorter than the first nucleic acid strand (e.g., shorter by 3 base in length, 2 base in length, or 1 base in length) (FIG. 1(b)).

In a further embodiment, the second nucleic acid strand may comprise at least one overhanging region located on one or both of the 5' end side and the 3' end side of the complementary region. An example of this embodiment is described in PCT/JP2017/035553. An "overhanging region" means a region adjacent to the complementary region, where the 5' end of the second nucleic acid strand extends beyond the 3' end of the first nucleic acid strand, and/or the 3' end of the second nucleic acid strand extends beyond the 5' end of the first nucleic acid strand, when the first nucleic acid strand and the second nucleic acid strand anneal to form a double-stranded structure. In other words, it means nucleotide region(s) in the second nucleic acid strand, protruded from the double-stranded structure. The overhanging region in the second nucleic acid strand may be located on the 5' end side of the complementary region (FIG. 2(a)), or on the 3' end side (FIG. 2(b)). The overhanging regions in the second nucleic acid strand may be located on the 5' end side and the 3' end side of the complementary region (FIG. 2(c)).

In an embodiment, the overhanging region in the second nucleic acid strand does not comprise a base sequence that is complementary to the first nucleic acid strand. The overhanging region may comprise a base sequence having a complementarity of 50% or less, 40% or less, 30% or less, 25% or less, 20% or less, 15% or less, 10% or less, 5% or less, or 0% with the base sequence of the first nucleic acid strand.

In an embodiment, it is preferable that the overhanging region in the second nucleic acid strand is substantially not able to hybridize to a transcriptional product in the cell, and does not affect gene expression. For example, it is preferable that the overhanging region does not include a therapeutic oligonucleotide, such as an antisense oligonucleotide, a microRNA inhibitor (antimiR), a splice-switching oligonucleotide, a single-stranded siRNA, a microRNA, and a pre-microRNA.

The base sequence of an overhanging region may comprise a base sequence having an identity of at least 70%, at least 80%, at least 85%, at least 90%, at least 93%, at least 95%, at least 98%, or 100% with a base sequence shown in any one of SEQ ID NOs: 7 to 11, or a base sequence in which at least some of the T's of the base sequence are replaced with U. The overhanging region may comprise a natural nucleotide and/or a non-natural nucleotide including the above base sequence.

The overhanging region in a nucleic acid complex of the present invention is preferably a single-stranded region.

The overhanging region in the second nucleic acid strand may be at least 5 base in length, at least 6 base in length, at least 7 base in length, at least 8 base in length, at least 9 base in length, at least 10 base in length, at least 11 base in length, at least 12 base in length, or at least 13 base in length, but not limited thereto. The overhanging region is 30 base in length or less, 29 base in length or less, 28 base in length or less, 27 base in length or less, 26 base in length or less, 25 base in length or less, 24 base in length or less, 23 base in length or less, 22 base in length or less, 21 base in length or less, 20 base in length or less, 19 base in length or less, 18 base in length or less, 17 base in length or less, 16 base in length or less, 15 base in length, or 14 base in length or less. The overhanging region may be, for example, from 5 to 20 base in length, from 6 to 18 base in length, from 7 to 17 base in length, from 8 to 12 base in length, or from 9 to 15 base in length. In a case where an overhanging region exists on each of the 5' end side and the 3' end side of the complementary region, the lengths of the respective overhanging regions may be the same or different.

In general, a "nucleoside" is a combination of a base and a sugar. The nucleobase (also known as a base) moiety of a nucleoside is usually a heterocyclic base moiety. A "nucleotide" further comprises a phosphate group covalently bonded to the sugar moiety of the nucleoside. In a nucleoside comprising a pentofuranosyl sugar, a phosphate group is linkable to the 2', 3', or 5' hydroxyl portion of the sugar. An oligonucleotide is formed by contiguous nucleosides linked by a covalent bond, forming a linear polymer oligonucleotide. Inside the oligonucleotide structure, it is conceived that a phosphate group generally forms an internucleoside bond in the oligonucleotide.

A nucleic acid strand can comprise a natural nucleotide and/or a non-natural nucleotide. A "natural nucleotide" comprises deoxyribonucleotide found in DNA and ribonucleotide found in RNA. The "deoxyribonucleotide" and "ribonucleotide" may be also occasionally referred to as "DNA nucleotide" and "RNA nucleotide", respectively.

Similarly, a "natural nucleoside" comprises deoxyribonucleoside found in DNA and ribonucleoside found in RNA. The "deoxyribonucleoside" and "ribonucleoside" may be also occasionally referred to as "DNA nucleoside" and "RNA nucleoside," respectively.

A "non-natural nucleotide" refers to any nucleotide other than natural nucleotide and comprises a modified nucleotide or a nucleotide mimic. Similarly, a "non-natural nucleoside" refers to any nucleoside other than natural nucleoside, and comprises a modified nucleoside, or a nucleoside mimic. A "modified nucleotide" means a nucleotide having one or more of a modified sugar moiety, a modified internucleoside bond, and a modified nucleobase. A "modified nucleoside" means a nucleoside having a modified sugar moiety and/or a modified nucleobase. A nucleic acid strand comprising a non-natural oligonucleotide is in many cases more preferable than a natural type, because of such desirable characteristics as enhanced cellular uptake, enhanced affinity for a nucleic acid target, increased stability in the presence of a nuclease, or increased inhibitory activity.

The term "modified internucleoside bond" refers to an internucleoside bond having a substitution or any change from a naturally occurring internucleoside bond (i.e., phosphodiester bond). The modified internucleoside bond comprises an internucleoside bond comprising a phosphorus atom, and an internucleoside bond without a phosphorus atom. Examples of a typical phosphorus-containing internucleoside bond include, but not limited to, a phosphodiester bond, a phosphorothioate bond, a phosphorodithioate bond, a phosphotriester bond, a methylphosphonate bond, a methylthiophosphonate bond, a boranophosphate bond, and a phosphoramidate bond. A phosphorothioate bond refers to an internucleoside bond in which a non-bridging oxygen atom of a phosphodiester bond is substituted with a sulfur atom. A method for preparing a phosphorus-containing bond or a phosphorus-free bond is well known. A modified internucleoside bond should preferably be a bond whose nuclease resistance is higher than a naturally occurring internucleoside bond.

A "modified nucleobase" or a "modified base" means any nucleobase other than adenine, cytosine, guanine, thymine, or uracil. An "unmodified nucleobase" or an "unmodified base" (natural nucleobase) means adenine (A) and guanine (G), which are purine bases, as well as thymine (T), cytosine (C), and uracil (U), which are pyrimidine bases. Examples of a modified nucleobase include, but not limited to, 5-methylcytosine, 5-fluorocytosine, 5-bromocytosine, 5-iodocytosine, N4-methylcytosine, N6-methyladenine, 8-bromoadenine, N2-methylguanine, and 8-bromoguanine. A modified nucleobase is preferably 5-methylcytosine.

The term "modified sugar" refers to a sugar having a substitution and/or any change from a natural sugar moiety (i.e., a sugar moiety found in DNA(2'-H) or RNA(2'-OH)). A nucleic acid strand may, in some cases, comprise one or more modified nucleoside including a modified sugar. Such a sugar-modified nucleoside can impart beneficial biological properties, such as an enhanced nuclease stability, an increased binding affinity, or the like to a nucleic acid strand. In a certain embodiment, a nucleoside comprises a chemically modified ribofuranose ring moiety. Examples of a chemically modified ribofuranose ring include, but not limited to, addition of a substituent (including 5' or 2' substituent), formation of a bicyclic nucleic acid (bridged nucleic acid, BNA) by forming a bridge between non-geminal ring atoms, and substitution of a ribosyl ring oxygen atom with S, N(R), or C(R1)(R2) (wherein R, R1 and R2 independently represent H, a $C_1$ to $C_{12}$ alkyl, or a protective group), and a combination thereof.

Examples of a nucleoside having a modified sugar moiety include, but not limited to, a nucleoside having a substituent, such as 5'-vinyl, 5'-methyl(R or S), 4'-S, 2'-F (2'-fluoro group), 2'-OCH$_3$ (2'-OMe group, or 2'-O-methyl group), and 2'-O(CH$_2$)$_2$OCH$_3$. A substituent at the 2' position may be selected from allyl, amino, azide, thio, —O-allyl, —O—(C$_1$-C$_{10}$ alkyl), —OCF$_3$, —O(CH$_2$)$_2$SCH$_3$, —O(CH$_2$)$_2$—O—N(Rm)(Rn), and —O—CH$_2$—C(=O)—N(Rm)(Rn), wherein each Rm and Rn is independently H or a substituted or unsubstituted C$_1$-C$_{10}$ alkyl. A "2'-modified sugar" means a furanosyl sugar modified at the 2' position.

The term "bicyclic nucleoside" refers to a modified nucleoside comprising a bicyclic sugar moiety. A nucleic acid comprising a bicyclic sugar moiety is generally referred to as bridged nucleic acid (BNA). A nucleoside comprising a bicyclic sugar moiety is sometimes referred to as "bridged nucleoside".

A bicyclic sugar may be a sugar in which the carbon atom at the 2' position and the carbon atom at the 4' position are bridged via two or more atoms. Examples of a bicyclic sugar are publicly known to those skilled in the art. A subgroup of nucleic acid (BNA) comprising a bicyclic sugar may be described as having a carbon atom at the 2' position and a carbon atom at the 4' position bridged by 4'-(CH$_2$)$_p$—O-2', 4'-(CH$_2$)$_p$—CH$_2$-2', 4'-(CH$_2$)$_p$—S-2', 4'-(CH$_2$)$_p$—OCO-2', or 4'-(CH$_2$)$_n$—N(R$_3$)—O—(CH$_2$)$_m$-2' [in the formula, p, m, and n respectively represent an integer of 1 to 4, an integer of 0 to 2, and an integer of 1 to 3; and R3 represents a hydrogen atom, an alkyl group, an alkenyl group, a cycloalkyl group, an aryl group, an aralkyl group, an acyl group, a sulfonyl group, or a unit substituent (such as a fluorescently or chemiluminescently labeled molecule, a functional group having nucleic acid cleavage activity, and intracellular or intranuclear localization signal peptide)]. Further, regarding the BNA according to a specific embodiment, in an OR$_2$ substituent on the carbon atom at the 3' position and an OR' substituent on the carbon atom at the 5' position, R$_1$ and R$_2$ are typically a hydrogen atom, but they may be the same as or different from each other, and further, a protecting group for a hydroxyl group for nucleic acid synthesis, an alkyl group, an alkenyl group, a cycloalkyl, an aryl group, an aralkyl group, an acyl group, a sulfonyl group, a silyl group, a phosphate group, a phosphate group protected by a protecting group for nucleic acid synthesis, or —P(R$_4$)R$_5$ [where R$_4$ and R$_5$ may be the same as or different from each other, and respectively are a hydroxyl group, a hydroxyl group protected by a protecting group for nucleic acid synthesis, a mercapto group, a mercapto group protected by a protecting group for nucleic acid synthesis, an amino group, an alkoxy group having 1 to 5 carbon atoms, an alkylthio group having 1 to 5 carbon atoms, a cyanoalkoxy group having 1 to 6 carbon atoms, or an amino group substituted with an alkyl group having 1 to 5 carbon atoms]. Non-limiting examples of such BNA include methyleneoxy (4'-CH$_2$—O-2') BNA (LNA (Locked Nucleic Acid®, also known as 2',4'-BNA), e.g., α-L-methyleneoxy (4'-CH$_2$—O-2') BNA, or β-D-methyleneoxy (4'-CH$_2$—O-2') BNA, ethyleneoxy (4'-(CH$_2$)$_2$—O-2') BNA (also known as ENA), β-D-thio (4'-CH$_2$—S-2') BNA, aminooxy (4'-CH$_2$—O—N(R$_3$)-2') BNA, oxyamino (4'-CH$_2$—N(R$_3$)—O-2') BNA (also known as 2',4'-BNA$^{NC}$), 2',4'-BNA$^{coc}$, 3'-amino-2',4'-BNA, 5'-methyl BNA, (4'-CH(CH$_3$)—O-2') BNA (also known as cEt BNA), (4'-CH(CH$_2$OCH$_3$)—O-2')BNA (also known as cMOE BNA), amide BNA (4'-C(O)—N(R)-2') BNA (R=H, Me) (also known as AmNA), 2'-O,4'-C-spirocyclopropylene bridged nucleic acid (also known as scpBNA), and other BNAs known to those skilled in the art.

A bicyclic nucleoside having a methyleneoxy (4'-CH$_2$—O-2') bridge is sometimes referred to as LNA nucleoside.

The method for preparing a modified sugar is well known to those skilled in the art. In a nucleotide having a modified sugar moiety, the nucleobase moiety (natural one, modified one, or a combination thereof) may be maintained for hybridization with an appropriate nucleic acid target.

Figure 6:
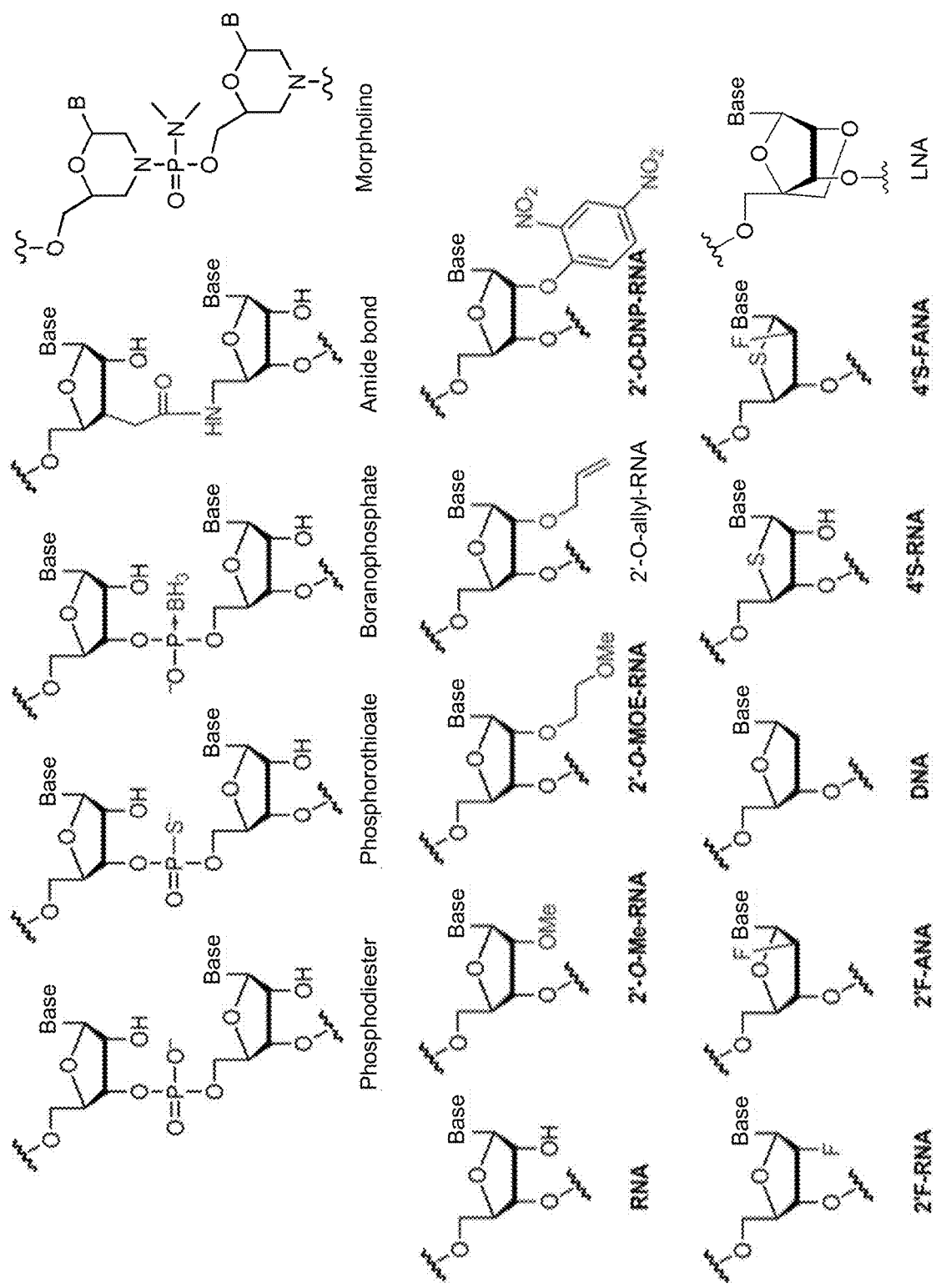
FIG. 6 is a diagram showing the structures of various natural nucleotides or non-natural nucleotides.

The "nucleoside mimic" comprises a structure used for substituting a sugar, or a sugar and a base, and, not mandatorily, a bond at one or more positions of an oligomeric compound. The term "oligomeric compound" means a polymer of linked monomeric subunits capable of hybridizing to at least one region of a nucleic acid molecule. Example of a nucleoside mimic include morpholino, cyclohexenyl, cyclohexyl, tetrahydropyranyl, bicyclic or tricyclic sugar mimic, for example, a nucleoside mimic having a non-furanose sugar unit. The "nucleotide mimic" includes a structure used for substituting a nucleoside and a bond at one or more positions of an oligomeric compound. Examples of a nucleotide mimic include a peptide nucleic acid, and a morpholino nucleic acid (a morpholino linked with —N(H)—C(=O)—O— or other non-phosphodiester bonds). A peptide nucleic acid (PNA) is a nucleotide mimic having a main chain in which N-(2-aminoethyl)glycine is linked by an amide bond in place of a sugar. An example of the structure of a morpholino nucleic acid is shown in FIG. 6. A "mimic" refers to a group that substitutes one or more of a sugar, a nucleobase, and an internucleoside bond. In general, a mimic is used in place of a sugar or a combination of sugar and an internucleoside bond, and a nucleobase is maintained for hybridization to a selected target.

In general, modifications can be performed such that nucleotides in the same strand can independently undergo different modifications. In addition, to confer resistance to enzymatic cleavage, the same nucleotide may have a modified internucleoside bond (e.g., phosphorothioate bond), and also have a modified sugar (e.g., 2'-O-methyl modified sugar, or bicyclic sugar). Further, the same nucleotide can have a modified nucleobase (e.g., 5-methylcytosine), and also have a modified sugar (e.g., 2'-O-methyl modified sugar, or bicyclic sugar).

The number, type, and position of a non-natural nucleotide in a nucleic acid strand can influence the antisense effect or the like provided by a nucleic acid complex. Selection of a modification may vary depending on the sequence of a target gene or the like, but one skilled in the art can determine a suitable embodiment by referring to the description of a literature related to the antisense method (for example, WO 2007/143315, WO 2008/043753, and WO 2008/049085). Furthermore, when the antisense effect of the nucleic acid complex after the modification is measured, if the measurement value thus obtained is not significantly lower than the measurement value of the nucleic acid complex before the modification (for example, in a case where the measurement value obtained after the modification are 70% or more, 80% or more, or 90% or more with respect to the measurement value of the nucleic acid complex before the modification), a relevant modification may be evaluated.

The measurement of an antisense effect may be performed, for example, by administering a test nucleic acid compound to a subject (e.g., mouse), and measuring the expression amount of a target gene whose expression is modulated by the antisense effect provided by the test nucleic acid compound, or the level (amount) of the target transcriptional product (for example, the amount of mRNA, or the amount of RNA such as microRNA, the amount of cDNA, or the amount of protein), for example, several days to several months after the administration (for example, after 2 to 7 days or 1 month)

For example, in a case where the expression amount of a target gene, or the level of a target transcriptional product measured is reduced by at least 10%, at least 20%, at least 25%, at least 30%, or at least 40% compared to the negative control (e.g., vehicle administration), it is demonstrated that the test nucleic acid compound can produce an antisense effect (reduction of target transcriptional product amount).

The internucleoside bond in the first nucleic acid strand may be a naturally occurring internucleoside bond and/or a modified internucleoside bond.

At least one, at least two, or at least three internucleoside bonds from the 5' end of the first nucleic acid strand may be modified internucleoside bonds. At least one, at least two, or at least three internucleoside bonds from the 3' end of the first nucleic acid strand may be modified internucleoside bonds. For example, two internucleoside bonds from the end of a nucleic acid strand refers to an internucleoside bond closest to the end of the nucleic acid strand, and an internucleoside bond positioned next thereto and located in the direction opposite to the end of the nucleic acid strand. A modified internucleoside bond(s) at the terminal region of a nucleic acid strand is preferred because they can reduce or inhibit undesired degradation of the nucleic acid strand.

The modified internucleoside bond(s) may be at least 70%, at least 80%, at least 85%, at least 90%, at least 93%, at least 95%, at least 98%, or 100% of the internucleoside bonds of the antisense oligonucleotide region in the first nucleic acid strand. The modified internucleoside bond may be a phosphorothioate bond.

The nucleoside in the first nucleic acid strand may be a natural nucleoside (comprising deoxyribonucleoside, ribonucleoside, or both) and/or a non-natural nucleoside.

The antisense oligonucleotide region in the first nucleic acid strand may be an antisense oligonucleotide region of a gapmer type (a gapmer type antisense oligonucleotide region). A "gapmer type" refers to a nucleoside constitution consisting of a central region (DNA gap region) including at least four contiguous deoxyribonucleosides, and regions (5' wing region, and 3' wing region) which comprise non-natural nucleosides and are located on the 5' end side and the 3' end side of the central region. The gapmer in which a non-natural nucleoside is constituted with a bridged nucleoside is specifically referred to as "BNA/DNA gapmer". The length of the DNA gap region may be 4 to 20 base in length, 5 base in length, 6 to 16 base in length, 7 to 14 base in length, or 8 to 12 base in length. The lengths of the 5' wing region and the 3' wing region may independently be usually 1 to 10 base in length, 1 to 7 base in length, 2 to 5 base in length, or 2 to 3 base in length. The 5' wing region and the 3' wing region are required to comprise at least one non-natural nucleoside, and may further comprise a natural nucleoside. A gapmer type antisense oligonucleotide region may have a BNA/DNA gapmer type nucleoside constitution comprising a 5' wing region comprising two or three bridged nucleosides, a 3' wing region comprising two or three bridged nucleosides, and a DNA gap region therebetween. The bridged nucleoside may comprise a modified nucleobase (e.g., 5-methylcytosine). The gapmer may be a "LNA/DNA gapmer" in which the bridged nucleoside is constituted by LNA nucleoside.

The antisense oligonucleotide region in the first nucleic acid strand may be an antisense oligonucleotide region of a mixmer type (a mixmer type antisense oligonucleotide region). A "mixmer" means herein a nucleic acid strand which comprises alternate natural nucleosides and non-natural nucleosides having periodic or random segment lengths, and does not comprise four or more contiguous deoxyribonucleosides or ribonucleosides. Among mixmers, a mixmer in which the non-natural nucleoside is a bridged nucleoside, and the natural nucleoside is a deoxyribonucleoside, is specifically called "BNA/DNA mixmer". A mixmer is not limited to comprise only two kinds of nucleosides. A mixmer may comprise any number of kinds of nucleosides, irrespective of a natural or modified nucleoside, or a nucleoside mimic. For example, it may comprise one or two contiguous deoxyribonucleosides separated by a bridged nucleoside (e.g., LNA nucleoside). A bridged nucleoside may further comprise a modified nucleobase (e.g., 5-methylcytosine).

The first nucleic acid strand may comprise entirely or partly a nucleoside mimic or a nucleotide mimic. A nucleotide mimic may be a peptide nucleic acid and/or a morpholino nucleic acid. The first nucleic acid strand may comprise at least one modified nucleoside. The modified nucleoside may comprise a 2'-modified sugar. The 2'-modified sugar may be a sugar comprising a 2'-O-methyl group.

An internucleoside bond in the second nucleic acid strand may be a naturally occurring internucleoside bond and/or a modified internucleoside bond.

All of the internucleoside bonds in the second nucleic acid strand may be modified internucleoside bonds. Alternatively, all of the internucleoside bonds in the second nucleic acid strand may be natural internucleoside bonds.

At least one, at least two, or at least three internucleoside bonds from the 5' end of the second nucleic acid strand may be modified internucleoside bonds. At least one, at least two, or at least three internucleoside bonds from the 3' end of the second nucleic acid strand may be modified internucleoside bonds.

Figure 2:
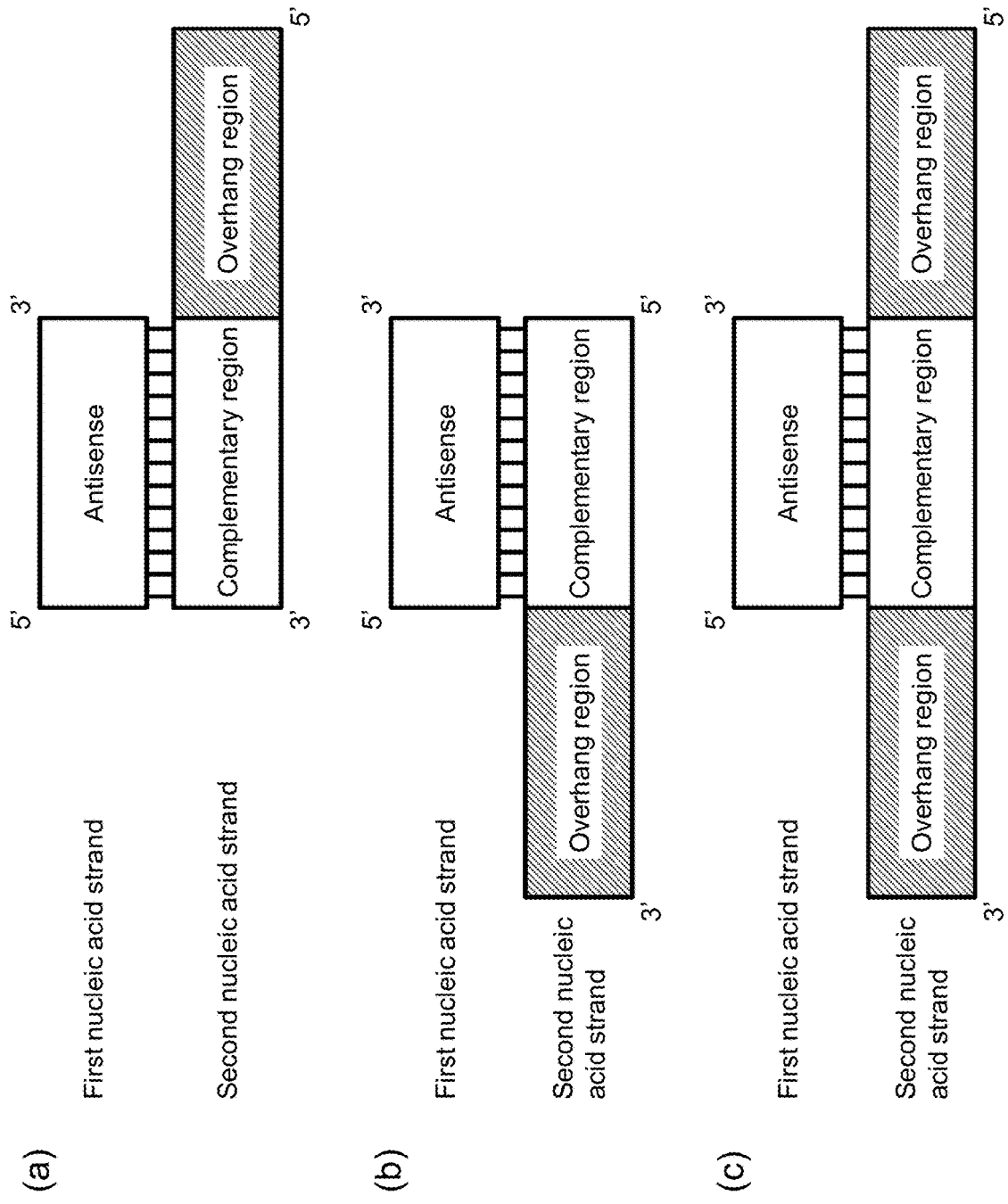
FIGS. 2(a) to (c) are each a schematic diagram showing an example of a specific embodiment of a nucleic acid complex according to the present invention, where the second nucleic acid strand comprises a complementary region and an overhanging region.

In an embodiment where the second nucleic acid strand comprises an overhanging region, at least one, at least two, or at least three internucleoside bonds from the free end of the overhanging region in the second nucleic acid strand may be modified internucleoside bonds. The "free end of the overhanging region" refers to herein the end of the overhanging region that is not bound to the complementary region. For example, in an embodiment where the overhanging region is located on the 5' end side of the complementary region as shown in FIG. 2(a), since the 3' end of the overhanging region is bound to the complementary region, the free end of the overhanging region means the 5' end of the second nucleic acid strand. Conversely, in an embodiment where the overhanging region is located on the 3' end side of the complementary region as shown in FIG. 2(b), the free end of the overhanging region means the 3' end of the second nucleic acid strand. Further, in an embodiment where the overhanging regions are located on both the 5' end side and the 3' end side of the complementary region as shown in FIG. 2(c), the free ends of the overhanging regions are both the ends (5' end and 3' end) of the second nucleic acid strand. For example, two internucleoside bonds from the free end of the overhanging region in the second nucleic acid strand means the internucleoside bond closest to the free end of the overhanging region in the second nucleic acid strand, and the internucleoside bond contiguous thereto and positioned away from the free end. Such terminal modified internucleoside bonds are preferred because they can reduce or inhibit undesired degradation of the overhanging region. The modified internucleoside bond may be a phosphorothioate bond.

Modified internucleoside bonds may be at least 50%, at least 60%, at least 70%, at least 75%, at least 80%, at least 85%, at least 90%, at least 95% (e.g., at least 96%, at least 97%, at least 98%, or at least 99%), or preferably 100% of the internucleoside bonds in the overhanging region in the second nucleic acid strand. An internucleoside bond in the overhanging region in the second nucleic acid strand means a bond between the nucleosides constituting the overhanging region, while an internucleoside bond between the overhanging region and the complementary region in the second nucleic acid strand is not included. For example, when an overhanging region consists of 10 nucleotides, then the number of internucleoside bonds in the region is 9. However, the internucleoside bond between the overhanging region and the complementary region may be a modified internucleoside bond, or a natural internucleoside bond. The modified internucleoside bond may be a phosphorothioate bond.

In an embodiment where the second nucleic acid strand comprises an overhanging region, at least one, at least two, or at least three internucleoside bonds from the free end of the complementary region in the second nucleic acid strand may be modified internucleoside bonds. The "free end of the complementary region" refers to the end on the side not bound to the overhanging region in the complementary region. For example, in an embodiment where the overhanging region is located on the 5' end side of the complementary region as shown in FIG. 2(a), the free end of the complementary region refers to the 3' end of the second nucleic acid strand. Conversely, in an embodiment where the overhanging region is located on the 3' end side of the complementary region as shown in FIG. 2(b), the free end of the complementary region refers to the 5' end of the second nucleic acid strand. On the other hand, in an embodiment where overhanging regions are located on both the 5' end side and the 3' end side of the complementary region as shown in FIG. 2(c), a free end of the complementary region does not exist. The modified internucleoside bond may be a phosphorothioate bond.

In a preferred embodiment, all the internucleoside bonds in the overhanging region in the second nucleic acid strand are modified internucleoside bonds, and at least two internucleoside bonds from the free end of the complementary region are modified internucleoside bonds.

Nucleosides in the second nucleic acid strand may be natural nucleosides (comprising deoxyribonucleoside, ribonucleoside, or both) and/or non-natural nucleosides.

The complementary region in the second nucleic acid strand may comprise natural nucleosides (including deoxyribonucleoside, ribonucleoside, or both) and/or non-natural nucleosides.

In an embodiment, the complementary region in the second nucleic acid strand may comprise at least two, at least three, at least four, or at least five contiguous ribonucleosides. Such contiguous ribonucleosides can form a double strand with a DNA gap region of a gapmer type oligonucleotide region in the first nucleic acid strand. The double strand can be recognized by RNase H and facilitate cleavage of the second nucleic acid strand by RNase H. The contiguous ribonucleosides may be linked by a phosphodiester bond. The nucleosides in the complementary region in the second nucleic acid strand may consist of ribonucleosides.

In another embodiment, the complementary region in the second nucleic acid strand may be without at least two contiguous ribonucleosides. The nucleosides in the complementary region in the second nucleic acid strand may consist of ribonucleosides.

The complementary region in the second nucleic acid strand may comprise at least one, at least two, or at least three modified nucleosides from the 5' end. The complementary region in the second nucleic acid strand may comprise at least one, at least two, or at least three modified nucleosides from the 3' end. The complementary region in the second nucleic acid strand may comprise at least one, at least two, or at least three modified nucleosides from the 5' end, and comprise at least one, at least two, or at least three modified nucleosides from the 3' end. The modified nucleosides may comprise a modified sugar and/or a modified nucleobase. The modified sugar may be a bicyclic sugar, or a 2'-modified sugar (e.g., a sugar containing a 2'-O-methyl group). The modified nucleobase may be 5-methylcytosine.

In an embodiment where the second nucleic acid strand comprises an overhanging region, at least one, at least two, or at least three nucleosides from the free end of the complementary region may be modified nucleosides. Specifically, one to three nucleosides from the free end of the complementary region may be modified nucleosides (e.g., nucleoside containing 2'-modified sugar, such as sugar that contains a 2'-O-methyl group), and other nucleosides in the complementary region may be a natural nucleoside (containing deoxyribonucleoside, ribonucleoside, or both).

In an embodiment, one to three nucleosides from the free end of the complementary region in the second nucleic acid strand may be modified nucleosides (e.g., a nucleoside comprising 2'-modified sugar, such as sugar comprising a 2'-O-methyl group), and other nucleosides in the complementary region may be deoxyribonucleosides. In another embodiment, at least 50%, at least 60%, at least 70%, at least 80%, at least 90%, or at least 95% of the nucleosides of the complementary region in the second nucleic acid strand may be natural nucleosides.

In an embodiment in which the second nucleic acid strand comprises an overhanging region, the overhanging region in the second nucleic acid strand may comprise a natural nucleoside (comprising deoxyribonucleoside, ribonucleoside, or both) and/or a non-natural nucleoside.

In an embodiment, nucleosides of an overhanging region may comprise a deoxyribonucleoside, or consist of deoxyribonucleosides. In another embodiment, at least one, at least two, or at least three, more specifically one to three nucleosides from the free end of an overhanging region may be modified nucleosides. Further, at least one, at least two, or at least three, more specifically one to three nucleosides from the bound end of the overhanging region may be modified nucleosides. The "bound end of the overhanging region" herein refers to the end of the overhanging region, which is bound to the complementary region. A modified nucleoside may comprise a modified sugar and/or a modified nucleobase. The modified sugar may be a bicyclic sugar (e.g., a sugar comprising a 4'-CH$_2$—O-2' group). The modified nucleobase may be 5-methylcytosine.

In an embodiment, at least two nucleosides from the free end of an overhanging region may be modified nucleosides (e.g., a nucleoside containing a bicyclic sugar such as a sugar containing a 4'-CH$_2$—O-2' group). When a bicyclic sugar is comprised in an overhanging region, the strand length of the overhanging region may be, for example, from 9 to 12 bases.

In an embodiment, the nucleosides of an overhanging region may be free of a bicyclic sugar.

Furthermore, in another embodiment, the nucleosides in an overhanging region may be free of a modified nucleoside, and consist of natural deoxyribonucleosides and/or ribonucleosides. It can be advantageous in terms of synthesis cost to use natural deoxyribonucleosides and/or ribonucleosides. It can be also advantageous in terms of avoiding hybridization with an undesirable transcriptional product to use natural deoxyribonucleosides and/or ribonucleosides. When a bicyclic sugar is not comprised in the overhanging region, the strand length of the overhanging region can be, for example, from 9 to 17 bases.

The first nucleic acid strand and the second nucleic acid strand may comprise any combination of the modified internucleoside bonds and modified nucleosides described above.

Figure 3:
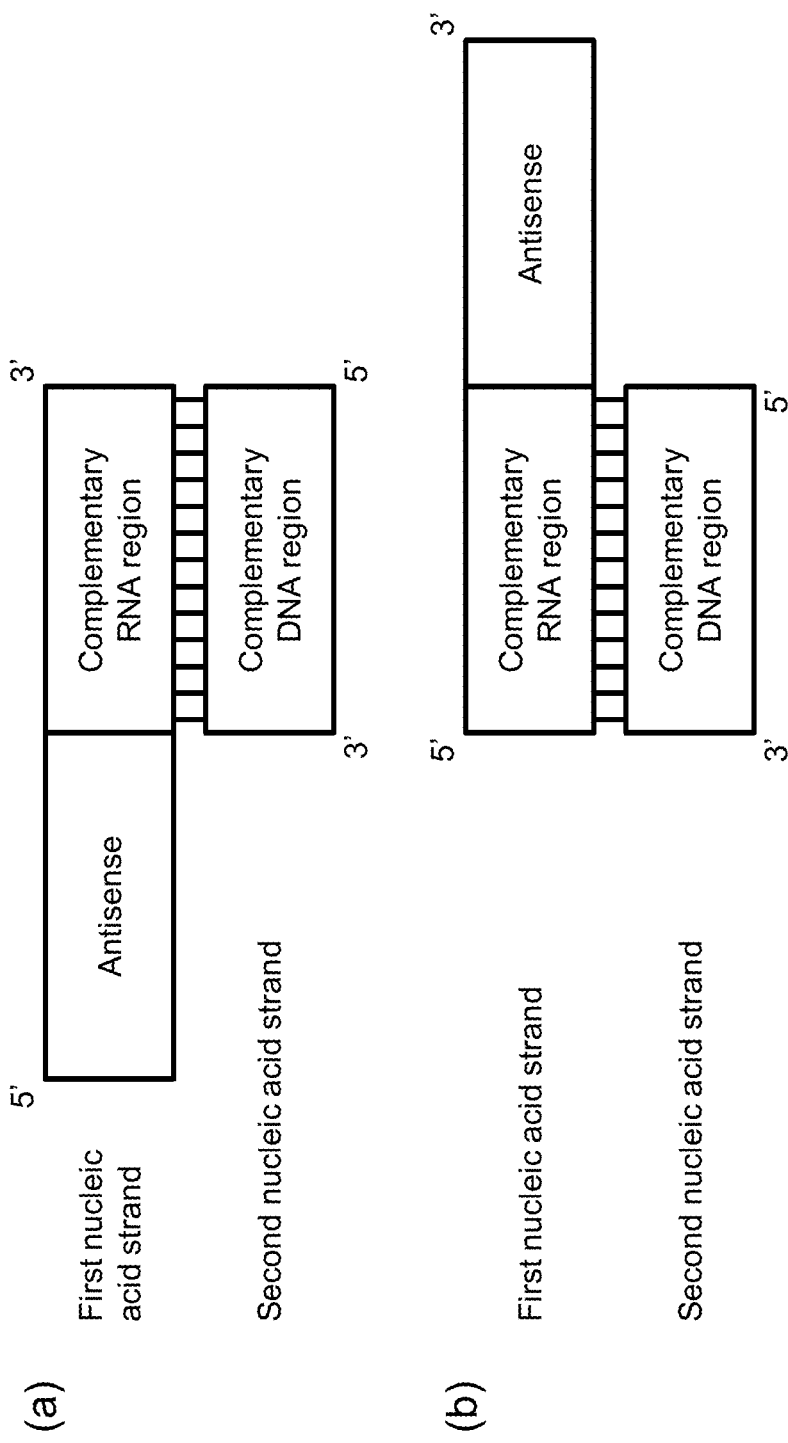
FIGS. 3(a) and (b) are each a schematic diagram showing an example of a specific embodiment of a nucleic acid complex according to the present invention, where the first nucleic acid strand comprises an antisense oligonucleotide region and a complementary RNA region.

In another specific embodiment, the first nucleic acid strand further comprises a complementary RNA region, and the complementary RNA region has at least two contiguous RNA nucleotides that can be recognized by RNase H when the first nucleic acid strand is hybridized to the second nucleic acid strand; the complementary region in the second nucleic acid strand is a complementary DNA region, and the complementary DNA region can hybridize to the complementary RNA region of the first nucleic acid strand to facilitate the recognition of at least two contiguous RNA nucleotides in the first nucleic acid strand by RNase H, and further the antisense oligonucleotide region in the first nucleic acid strand cannot hybridize with the second nucleic acid strand. As an example of this embodiment, there is a hetero-chimera-duplex oligonucleotide (HCDO) disclosed in International Publication No. WO 2014/192310. The antisense oligonucleotide region in the first nucleic acid strand may be located on the 5' end side of the complementary RNA region (FIG. 3(a)), or may be located on the 3' end side of the complementary RNA region (FIG. 3(b)). When a nucleic acid complex of this embodiment is introduced into a cell, the complementary RNA region is cleaved by RNase H to release the antisense oligonucleotide, and then the antisense oligonucleotide can function, for example, to modify the activity or the function of a transcriptional product (see International Publication No. WO 2014/192310).

The complementary DNA region is complementary to part or all of the complementary RNA region, and in some cases it may be complementary to part of the antisense oligonucleotide region. However, it is not required that the complementary RNA region is completely complementary to the complementary DNA region, or it has the same number of bases as the complementary DNA region.

The complementary RNA region may comprise 2, 3, 4, or 5, or even more, for example 5 to 20, 5 to 16, or 5 to 12 contiguous RNA nucleotides (natural RNA), which optionally may be flanked on one or both sides by modified RNA nucleotides.

The complementary DNA region may have a nucleoside constitution of gapmer type as described herein elsewhere.

Although there is no particular restriction on the length of the complementary RNA region or the complementary DNA region, it is usually at least 8 bases, at least 10 bases, at least 12 bases, or at least 13 bases. The length of the complementary RNA region or the complementary DNA region may be 20 bases or less, 25 bases or less, or 35 bases or less.

Figure 4:
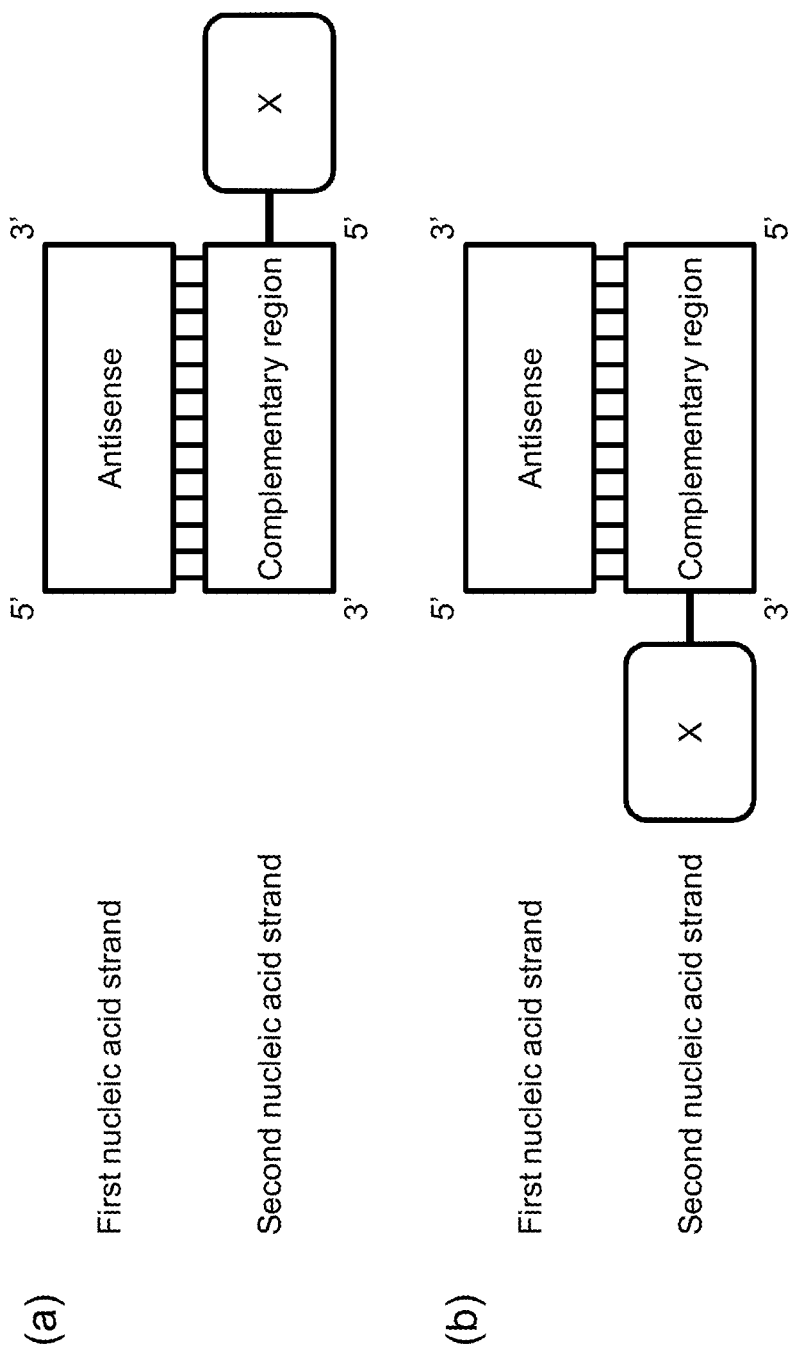
FIGS. 4(a) and (b) are each a schematic diagram showing an example of an embodiment of a portion of a nucleic acid complex comprising a functional moiety ("X").

In an embodiment, the second nucleic acid strand may comprise at least one functional moiety bound to a polynucleotide. The functional moiety as indicated by "X" in FIG. 4 may be linked to the 5' end of the second nucleic acid strand (FIG. 4(a), or linked to the 3' end (FIG. 4(b)). Alternatively, the functional moiety may be linked to a nucleotide internally positioned in the polynucleotide. In other embodiments, the second nucleic acid strand includes two or more functional moieties, which may be linked to a plurality of positions of the polynucleotide and/or linked as a group to one position of the polynucleotide.

The bond between the second nucleic acid strand and the functional moiety may be a direct bond or an indirect bond mediated by another substance. However, in a specific embodiment, it is preferable that the functional moiety is directly bound to the second nucleic acid strand via a covalent bond, an ionic bond, a hydrogen bond, or the like, and a covalent bond is more preferable considering that a more stable bond can be obtained. The functional moiety may also be linked to the second nucleic acid strand via a cleavable linking group. For example, the functional moiety may be linked via a disulfide bond.

There is no particular restriction on the structure of a "functional moiety" in a specific embodiment insofar as the functional moiety confers a desired function to a nucleic acid complex and/or the strand to which the functional moiety is bound. Examples of the desired function include a labeling function, a purifying function, and a delivering function. Examples of a moiety that provides a labeling function include compounds such as a fluorescent protein, and luciferase. Examples of a moiety that provides a purifying function include compounds such as biotin, avidin, His-tag peptide, GST-tag peptide, and FLAG-tag peptide.

In some embodiments, a functional moiety serves to enhance transport to a cell or a cell nucleus. For example, it has been demonstrated that a certain peptide tag, when it is conjugated with an oligonucleotide, enhances cellular uptake of an oligonucleotide. Examples thereof include the arginine-rich peptide P007 and B-peptide disclosed in Hai-Fang Yin, et al., Human Molecular Genetics, Vol. 17(24), 3909-3918 (2008), and the references therein. Intranuclear transport can be enhanced by conjugating a moiety such as m3G-CAP (see Pedro M. D. Moreno, et al., Nucleic Acids Res., Vol. 37, 1925-1935 (2009)) with an oligonucleotide.

It is preferable that a molecule having an activity of delivering a nucleic acid complex of some embodiments of the present invention to a "target site" in the body is bound to the second nucleic acid strand as a functional moiety, from the viewpoint of delivering a nucleic acid complex to a target site or a target region in the body with high specificity and high efficiency, so as to suppress quite efficiently expression of a target transcriptional product by a relevant nucleic acid (e.g., target gene).

The moiety having a "target delivering function" may be, for example, a lipid. Examples of such a lipid include a lipid such as cholesterol and a fatty acid (e.g., vitamin E (tocopherol, tocotrienol), vitamin A, and vitamin D); a liposoluble vitamin, such as vitamin K (e.g., acylcarnitine); an intermediate metabolite such as acyl-CoA; a glycolipid, a glyceride, and a derivative or an analog thereof. Among these, cholesterol and vitamin E (tocopherol and tocotrienol) are used in certain embodiments, considering that they have higher safety. However, a nucleic acid complex of a certain embodiment of the present invention may be not be bound to a lipid.

Also, from the viewpoint that a nucleic acid complex can be delivered to various organs with high specificity and high efficiency by binding to various proteins present on the cell surface of various organs, examples of a "functional moiety" of a certain embodiment include a peptide or a protein (e.g., a receptor ligand, and an antibody, and/or fragments thereof).

One skilled in the art can produce the first nucleic acid strand and the second nucleic acid strand constituting a nucleic acid complex by appropriately selecting known methods. For example, a nucleic acid can be produced by designing the base sequence of each nucleic acid based on the information about the base sequence of a target transcriptional product (or, in some examples, the base sequence of a target gene), synthesizing the nucleic acid using a commercial automatic nucleic acid synthesizer (such as product of Applied Biosystems, Inc., or product of Beckman Coulter, Inc.), and then purifying the thus obtained oligonucleotides using a reversed phase column or the like. The nucleic acid produced by this method is mixed in an appropriate buffer solution and denatured at about 90° C. to 98° C. for several min (e.g., 5 min), and then the nucleic acid is annealed at about 30° C. to 70° C. for about 1 to 8 hours, so that a nucleic acid complex can be produced in this manner. Production of an annealed nucleic acid complex is not limited to such time and temperature protocols. Conditions suitable for promoting annealing of strands are well known in the art. A nucleic acid complex to which a functional moiety is bound can be produced by using a nucleic acid species to which a functional moiety has been bound in advance, and performing the synthesis, purification, and annealing as described above. A large number of methods for linking a functional moiety to a nucleic acid are well known in the art. Alternatively, a nucleic acid strand is available on demand from a manufacturer (e.g., GeneDesign Inc.) by specifying a base sequence and a modification site or type.

<Composition for Administration to Central Nervous System>

A composition for administration to a central nervous system for modulating expression of a target transcriptional product in the central nervous system of a subject, comprising the above-described nucleic acid complex is provided. This composition is characterized in that the toxicity (side effect) associated with administration of a nucleic acid to the central nervous system of a subject is reduced (or non-toxic).

"Toxicity" means an effect of causing an objective or subjective symptom or functional abnormality undesirable to a subject, such as death, pain, tremor, convulsion, motor impairment, cognitive dysfunction, impaired consciousness, general malaise, fatigue, nausea or vomiting, dizziness, numbness, and wobbling. Toxicity may be toxicity to any organ. The toxicity may be neurotoxicity. The "neurotoxicity" means an effect that causes damage to a nervous tissue, including a central nervous tissue (including neurons) and a peripheral nervous tissue, and interferes with the normal activity of the nervous system. The neurotoxicity may cause any symptom selected from death, breathing abnormality, cardiovascular abnormality, headache, nausea or vomiting, unresponsiveness or low responsiveness, impaired consciousness, mental disorder, personality change, hallucination, delusion, cognitive dysfunction, abnormal posture, involuntary movement, tremor, convulsion, hyperactivity, disturbance of motor function, paralysis, sensory abnormality, or autonomic nervous system dysfunction. The neurotoxicity may be acute neurotoxicity. Acute neurotoxicity can be neurotoxicity that occurs within 1, 3, 6, 9, 12, 24, or 48 hours from the administration. The toxicity can be evaluated for example by an acute phase tolerability score, a side-effect event rate, or the mortality, as described in Examples below.

The present composition can exhibit reduced toxicity compared to administration of a single-stranded antisense oligonucleotide to the central nervous system of a subject. Here, the "single-stranded antisense oligonucleotide" means a nucleotide strand consisting solely of an antisense oligonucleotide region in the first nucleic acid strand constituting a nucleic acid complex of the present invention.

The present composition is for administration to the central nervous system of a subject. The administration to the central nervous system may be an administration via any administration route capable of administering the present composition to any tissue or body fluid of the central nervous system. For example, it may be intrathecal (or intraspinal) administration, or intraventricular administration.

A subject may be any animal, including human. However, there is no specific limitation on animal other than human. It may be any vertebrate such as mammals, birds, reptiles, amphibians, fish, and agnathonae, or invertebrate such as arthropods, molluscs, and echinoderms. For example, various livestock, poultry, pets, and laboratory animals can be a subject. The subject may be a subject in need of modulation of expression of a target transcriptional product in the central nervous system. The subject may also be a subject in need of a treatment of a central nervous system disease.

The present composition may be formulated by a known formulation method. For example, the composition can be made into an injectable agent, a peroral agent, or a topical preparation.

The present composition may appropriately incorporate a pharmaceutically acceptable carrier, specifically a surfactant, a pH regulator, a stabilizer, an excipient, a vehicle, a preservative, a diluent, an isotonizing agent, a sedative, a buffer, and other additives, as well as a pharmaceutically acceptable solvent, specifically sterile water, a physiological saline solution, a buffer solution (including phosphate buffer), and other solvents.

The dose of the present composition may be selected appropriately according to the age, body weight, symptoms, and health status of a subject, the dosage form, etc. The dose of the present composition may be, for example, in terms of nucleic acid complex, from 0.0000001 mg/kg/day to 1,000,000 mg/kg/day, from 0.00001 mg/kg/day to 10,000 mg/kg/day, or from 0.001 mg/kg/day to 100 mg/kg/day.

The present composition may be a pharmaceutical composition. The present composition may be for treating a central nervous system disease.

The present composition may be also a pharmaceutical composition for treating or preventing, for example, diseases (degenerative disease, vascular disorder, immune disease, endocrine and metabolic disease, tumor, or infectious disease) related to genetic abnormalities (e.g., gene mutation, gene deletion, gene insertion, gene conversion, or abnormality in the number of repetitive sequences), or, for example, abnormality in expression of a target gene (increase, decrease, or abnormality in gene variant).

In an embodiment, a pharmaceutical composition may be for treating or preventing a central nervous system disease, or a disease in which the nerve root or the dorsal root ganglion in the medullary cavity is impaired.

In an embodiment, a nucleic acid complex comprised in a composition for administration to the central nervous system may be free of a lipid such as vitamin E (tocopherol, tocotrienol), or cholesterol.

A disease to be treated with the present composition can be a disease of the nervous system related to genetic abnormality. The nervous system can be divided into the central nervous system and the peripheral nervous system, but a disease to be treated with the present composition may be primarily a central nervous system disease. The central nervous system consists of the brain and the spinal cord. The brain includes the cerebrum (cerebral cortex, cerebral white matter, and basal ganglion), the diencephalon (thalamus, subthalamic nucleus), the cerebellum (cerebellar cortex, cerebellar nucleus), and the brainstem (midbrain, substantia nigra, bridge, medulla oblongata). The spinal cord includes the cervical spinal cord, the thoracic spinal cord, the lumbar spinal cord, the sacral spinal cord, and the coccygeal spinal cord. Although the central nervous system herein may be any of these regions, it may be particularly the cerebral cortex (frontal lobe, temporal lobe, parietal lobe, or occipital lobe), the cerebellum, striatum, globus pallidus, claustrum, hippocampus, parahippocampal gyrus, brainstem, cervical spinal cord, thoracic spinal cord, or lumbar spinal cord. The peripheral nerve consists of the cranial nerve, and the spinal nerve. Thus, the target disease to be treated can be a disease in which the nerve root or the cauda equina in the medullary cavity, or the dorsal root ganglion is affected (e.g., carcinomatous meningitis).

Examples of a central nervous system disease include, but not limited to, brain tumor, Alzheimer's disease, Parkinson's disease, amyotrophic lateral sclerosis, multiple sclerosis, and Huntington's disease. For example, in a treatment of Alzheimer's disease, drug delivery to the hippocampus and/or the parietal lobe may be effective. In a treatment of frontotemporal dementia (FTD) (frontotemporal lobar degeneration (FTLD), semantic dementia (SD), or progressive nonfluent aphasia (PNFA)), and Pick disease, drug delivery to at least one of the frontal lobe, the temporal lobe, and the substantia nigra may be effective. In a treatment of dementia with Lewy bodies (DLB), or Parkinson's disease dementia, drug delivery to at least one of the occipital lobe, the substantia nigra, and the striatum may be effective. In a treatment of Parkinson's disease, drug delivery to the substantia nigra and/or the striatum may be effective. In a treatment of cortical basal ganglia degeneration (CBD), drug delivery to at least one of the frontal lobe, the parietal lobe, the basal ganglion, and the substantia nigra may be effective. In a treatment of progressive supranuclear paralysis (PSP), drug delivery to at least one of the frontal lobe, the basal ganglion, and the substantia nigra may be effective. In a treatment of amyotrophic lateral sclerosis, or spinal muscular atrophy, drug delivery to at least one of the frontal lobe, the parietal lobe, the substantia nigra, the basal ganglion, and the spinal cord may be effective. In a treatment of spinocerebellar degeneration (SCD) SCA1 type through SCA34 type, drug delivery to the brainstem and/or the cerebellum may be effective. In a treatment of dentatorubral-pallidoluysian atrophy (DRPLA), drug delivery to at least one of the brainstem, the basal ganglion, and the cerebellum may be effective. In a treatment of spinal and bulbar muscular atrophy (SBMA), drug delivery to at least one of the skeletal muscle, the brainstem, and the spinal cord may be effective. In a treatment of Friedreich's ataxia (FA), drug delivery to the brainstem and/or the cerebellum may be effective. In a treatment of Huntington's disease, drug delivery to at least one of the striatum, the frontal lobe, the parietal lobe, and the basal ganglion may be effective. In a treatment of a prion disease (mad cow disease, GSS), drug delivery to at least one of the cerebral cortex, the cerebral white matter, the basal ganglion, and the substantia nigra may be effective. In a treatment of cerebral white matter encephalopathy, drug delivery to the cerebral white matter may be effective. In particular it may be effective in a treatment of progressive multifocal leukoencephalopathy. In a treatment of encephalitis (viral, bacterial, fungal, or tuberculous), or meningitis (viral, bacterial, fungal, or tuberculous), drug delivery to the whole brain may be effective. In a treatment of metabolic encephalopathy, toxic encephalopathy, or trophopathic encephalopathy, drug delivery to the whole brain may be effective. In a treatment of cerebral infarction, cerebral hemorrhage, subarachnoid hemorrhage, moyamoya disease, anoxic encephalopathy, drug delivery to the whole brain may be effective. In a treatment of diffuse axonal injury, drug delivery to the cerebral white matter may be effective. In a treatment of head trauma, drug delivery to the whole brain may be effective. In a treatment of multiple sclerosis (MS) or neuromyelitis optica (NMO), drug delivery to at least one of the cerebral white matter, the cerebral cortex, the optic nerve, and the spinal cord may be effective. In a treatment of myotonic dystrophy (DM1, DM2), drug delivery to at least one of the skeletal muscle, the cardiac muscle, the cerebral cortex, and the cerebral white matter may be effective. In a treatment of hereditary spastic paraparesis (HSP), drug delivery to the parietal lobe and/or the spinal cord may be effective. In a treatment of Fukuyama muscular dystrophy, drug delivery to at least one of the skeletal muscles, the cerebral cortex, and the cerebral white matter may be effective. In a treatment of DLB, drug delivery to the frontal lobe and/or the parietal lobe may be effective. In a treatment of multiple system atrophy (MSA), drug delivery to at least one of the striatum, the basal ganglion, the cerebellum, the substantia nigra, the frontal lobe, and the temporal lobe may be effective. In a treatment of Alexander's disease, drug delivery to the cerebral white matter may be effective. In a treatment of CADASIL and CARASIL, drug delivery to the cerebral white matter may be effective.

Examples of a disease that targets the nerve root and the cauda equina include, but not limited to, Guillain-Barre syndrome, Fisher syndrome, chronic inflammatory demyelinating polyneuropathy, and cervical spondylotic radiculopathy. Further, peripheral neurogenic pain disease, Sjogren's syndrome, and paraneoplastic syndrome may be included.

Thus, a composition for treating each of the above diseases, or a method of treatment that includes administration of the composition is provided. Also a composition for modulating expression of a target transcriptional product (for example, for reducing the expression amount of a transcriptional product) at each of the above sites is provided.

Also a method of administering a low toxicity antisense nucleic acid medicine to the central nervous system of a subject, including a step of administering the above composition to the central nervous system of a subject is provided. This method may be a method of treating a central nervous system disease in a subject.

Also, a use of a nucleic acid strand including a complementary region that is complementary to at least part of an antisense oligonucleotide (such as a gapmer type or a mixmer type) for reducing the toxicity of the antisense oligonucleotide (such as a gapmer type or a mixmer type) is provided.

Further provided is a method for producing a low toxicity antisense nucleic acid medicine comprising:
(i) a step of preparing a first nucleic acid strand comprising an antisense oligonucleotide (such as a gapmer type or a mixmer type) region with respect to a target transcriptional product;
(ii) a step of preparing a second nucleic acid strand comprising a complementary region that is complementary to at least part of the first nucleic acid strand;
(iii) a step of forming a nucleic acid complex by annealing together the first nucleic acid strand and the second nucleic acid strand; and
(iv) a step of preparing an antisense nucleic acid medicine comprising the nucleic acid complex.
<Low Toxicity Composition>

A low toxicity composition, comprising the above-described nucleic acid complex, for modulating expression of a target transcriptional product in a subject is provided. This composition can exhibit a reduced toxicity compared to a case where a single-stranded antisense oligonucleotide is administered to a subject.

Such administration of the composition can be performed, for example, by either of a parenteral route, or a peroral route. Specific examples of parenteral administration include intravenous administration, intraarterial administration, intraperitoneal administration, subcutaneous administration, intradermal administration, tracheal/bronchial administration, rectal administration, and intramuscular administration, as well as administration by blood transfusion. Administration may be performed by, but not limited to, intravenous administration or subcutaneous administration. Administration by intramuscular injection, intravenous infusion, or implanted continuous subcutaneous administration is also possible. Since self-injection by a patient is possible in the case of subcutaneous administration, it is suitable. In the case of intravenous administration, the amount of a nucleic acid complex contained in a single dose of the composition, namely the single dose of a nucleic acid complex may be, for example, 0.001 mg/kg or more, 0.005 mg/kg or more, 0.01 mg/kg or more, 0.25 mg/kg or more, 0.5 mg/kg or more, 1 mg/kg or more, 2.5 mg/kg or more, 5 mg/kg or more, 10 mg/kg or more, 20 mg/kg or more, 30 mg/kg or more, 40 mg/kg or more, 50 mg/kg or more, 75 mg/kg or more, 100 mg/kg or more, 150 mg/kg or more, 200 mg/kg or more, 300 mg/kg or more, 400 mg/kg or more, or 500 mg/kg or more. For example, any amount within the range of 0.001 to 500 mg/kg (e.g., 0.001 mg/kg, 0.01 mg/kg, 0.1 mg/kg, 1 mg/kg, 5 mg/kg, 10 mg/kg, 50 mg/kg, 100 mg/kg, or 200 mg/kg) can be selected as appropriate. The toxicity that can be mitigated by such a low toxicity composition may be, for example, neurotoxicity or nephrotoxicity. Nephrotoxicity refers to a property that causes functional abnormality and/or functional reduction in the kidney. Evaluation of the renal function can be conducted by any technique known to those skill in the art, such as a serological and biochemical test.

EXAMPLES

The present invention will be described in more detail below by way of Examples. However, the technical scope of the present invention is not limited to these Examples.

Example 1

Experiments in vivo were conducted for examining side effects in the central nervous system due to the intraventricular administration of a double-stranded nucleic acid agent of an embodiment.

In this Example, side effects in the central nervous system were evaluated using four kinds of double-stranded agents shown in FIGS. 7(b) to (e) having a form of heteroduplex oligonucleotide (hereinafter referred to as "HDO"; see International Publication No. WO 2013/089283), and a single-stranded LNA/DNA gapmer type antisense oligonucleotide (hereafter referred to as "ASO") shown in FIG. 7(a) as a control.
(Preparation of a Nucleic Acid Agent)

The single-stranded ASO used as a control was a 13mer LNA/DNA gapmer (ASO (BACE1) 13mer in Table 1, FIG. 7(a)) comprising two LNA nucleosides from the 5' end, and three LNA nucleosides from the 3' end, and eight DNA nucleosides between them. This LNA/DNA gapmer is complementary to position 1569 to 1581 of the murine β-secretase 1 (BACE1) mRNA (SEQ ID NO: 1). By annealing the LNA/DNA gapmer (first strand) to the complementary strand (second strand), the following four kinds of double-stranded agent HDO were prepared.

Double-stranded agent (HDO cRNA all PO, FIG. 7(b)): consists of the first strand, and the second strand (cRNA (BACE1) all PO) in which 13 RNA nucleosides are linked by phosphodiester bonds.

Double-stranded agent (HDO cRNA all PS, FIG. 7(c)): consists of the first strand, and the second strand (cRNA (BACE1) all PS) in which 13 RNA nucleosides are linked by phosphorothioate bonds.

Double-stranded agent (HDO cDNA all PO, FIG. 7(d)): consists of the first strand, and the second strand (cDNA (BACE1) all PO) in which 13 DNA nucleosides are linked by phosphodiester bonds.

Double-stranded agent (HDO cDNA all PS, FIG. 7(e)): consists of the first strand, and the second strand (cDNA (BACE1) all PS) in which 13 DNA nucleosides are linked by phosphorothioate bonds.

Figure 7:
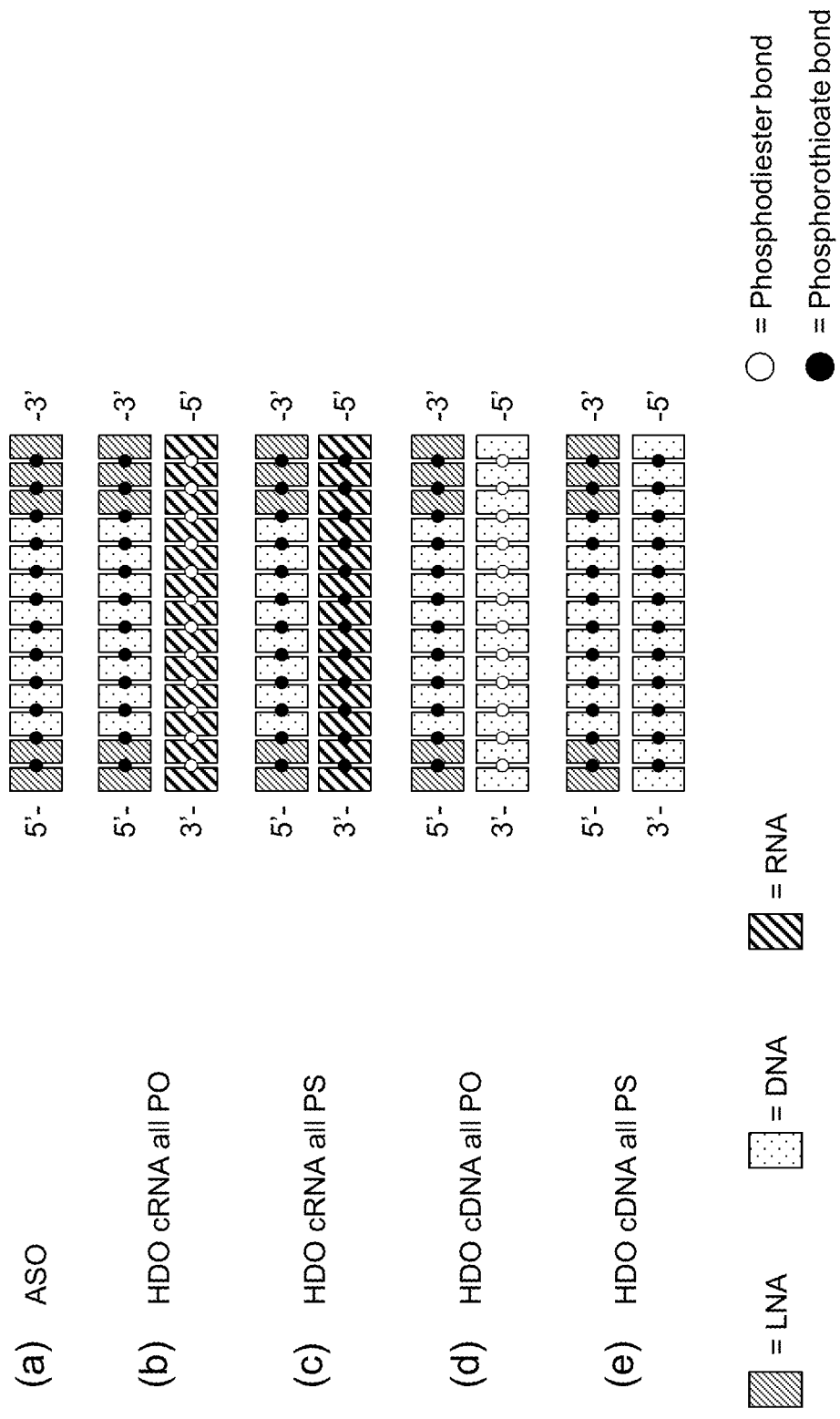
FIG. 7 shows schematic diagrams of the structures of the nucleic acids used in Example 1.

The sequences, chemical modifications and structures of the oligonucleotides used in Example 1 are shown in Table 1 and FIG. 7.

TABLE 1

Oligonucleotides used in Example 1

| Oligonucleotide name | Sequence (5'-3') | SEQ ID NO: |
|---|---|---|
| ASO (BACE1) 13mer | G(L)^T(L)^a^t^t^g^c^t^g^ a^G(L)^G(L)^A(L) | 12 |
| cRNA (BACE1) all PO | UCCUCAGCAAUAC | 13 |
| cRNA (BACE1) all PS | U^C^C^U^C^A^G^C^A^A^U^A^C | 13 |
| cDNA (BACE1) all PO | tcctcagcaatac | 14 |
| cDNA (BACE1) all PS | t^c^c^t^c^a^g^c^a^a^t^a^c | 14 |

Uppercase letter (L): LNA
Lowercase letter: DNA
Uppercase letter: RNA
^Phosphorothioate bond Synthesis of all the oligonucleotides was entrusted to GeneDesign Inc. (Osaka, Japan). To prepare the above-described double-stranded agent, the first strand and the second strand were mixed in an equimolar amount, and the solution was heated at 95° C. for 5 min, then cooled down to 37° C., and held for 1 hour, thereby annealing the nucleic acid strands. The annealed nucleic acids were stored at 4° C., or on ice.

(Experiments In Vivo)

Under 2.5 to 4% isoflurane anesthesia, 7-week-old female ICR mice were fixed with a brain stereotaxic apparatus. Subsequently, a 2 to 3 cm anteroposterior skin incision was made between the ears, and drilling was performed with a 1 mm-diameter drill at 1 mm leftward and 0.2 mm backward from the bregma. A Hamilton syringe was filled with a nucleic acid agent. The needle was inserted by about 3 mm into the perforation, the nucleic acid agent was administered into the left lateral ventricle at a rate of 2 to 3 μL/min to the dosage of 12 μmol per mouse (n=4 to 7), and the skin was sutured with a nylon thread. PBS (negative control) was administered to mice in the cerebral ventricle in the same manner.

At 1, 3, and 6 hours after administration, side effects (tolerability) in the central nervous system were assessed by the following 11 behavioral assessment items.
(1) Alert, bright and responsive.
(2) Standing or hunching without stimuli.
(3) Shows movements without stimuli.
(4) Shows forward movement after being lifted up.
(5) Shows any movements after being lifted up.
(6) Responds to tail pinch.
(7) Regular breathing.
(8) No hyperactivity.
(9) No motor dysfunction and ataxia.
(10) Normal posture.
(11) No tremors/convulsions.

Scoring was performed for each item with "abnormal" (1 point) or "normal" (0 point) for a mouse, and a score of each mouse was calculated as the total points (0 to 11 points) to obtain the acute tolerability score. Further, the percentage of mice in which any one of the 11 items above was found abnormal was calculated as the side-effect event rate (%). In addition, the number of mice that died within one day after the administration was recorded. The results of the respective groups were compared, and significant differences were further assessed by a Bonferroni test.

(Results)

The results of Example 1 are shown in Tables 2 to 4.

TABLE 2

| | Acute tolerability score | | |
|---|---|---|---|
| | 1 hour | 3 hours | 6 hours |
| PBS | 0 ± 0 | 0 ± 0 | 0 ± 0 |
| ASO | 7.4 ± 0.9 | 6.0 ± 0.7 | 2.4 ± 2.9 |
| HDO cRNA all PO | 0 ± 0 | 0 ± 0 | 0 ± 0 |
| HDO cRNA all PS | 0 ± 0 | 0 ± 0 | 0 ± 0 |
| HDO cDNA all PO | 0 ± 0 | 0 ± 0 | 0 ± 0 |
| HDO cDNA all PS | 0 ± 0 | 0 ± 0 | 0 ± 0 |

(n = 4, mean value ± SD)

TABLE 3

| | Side-effect event rate (%) | | |
|---|---|---|---|
| | 1 hour | 3 hours | 6 hours |
| PBS | 0 | 0 | 0 |
| ASO | 100 | 100 | 100 |
| HDO cRNA all PO | 0 | 0 | 0 |
| HDO cRNA all PS | 0 | 0 | 0 |
| HDO cDNA all PO | 0 | 0 | 0 |
| HDO cDNA all PS | 0 | 0 | 0 |

TABLE 4

| | Number of deaths/number of doses |
|---|---|
| PBS | 0/4 |
| ASO | 2/6 |
| HDO cRNA all PO | 0/4 |
| HDO cRNA all PS | 0/4 |
| HDO cDNA all PO | 0/4 |
| HDO cDNA all PS | 0/4 |

With respect to the acute tolerability scores shown in Table 2, a higher numerical value indicates a drug with lower tolerability. In the ASO administration group, rise of the acute tolerability score at 1 hour after the administration was observed, which thereafter decreased gradually, however the rise remained up to 6 hours. On the other hand, in the group of PBS administration (negative control) and the groups of administration of the four kinds of double-stranded agent HDO, the acute tolerability scores did not rise.

With respect to the side-effect event rates shown in Table 3, the side-effect event rate of the group of ASO administration was 100%, namely a side-effect was observed in all the mice, whereas the side-effect event rates in the group of PBS administration (negative control) and the groups of administration of the four kinds of double-stranded agent HDO were 0%, and no side effects were observed in these groups.

Two of the six mice in the ASO administration group died, whereas none of the mice in the PBS group (negative control) and the groups of administration of the four kinds of double-stranded agent HDO died (Table 4).

These results indicate that HDO which is a double-stranded agent can avoid a side effect (toxicity) in the central nervous system seen in the case of a single-stranded agent. The avoidance effect was found regardless of the nucleic acid species (RNA or DNA) or the type of the internucleoside bond comprised in the complementary strand (second strand) in HDO.

Example 2

An experiment in vivo for examining a side effect in the central nervous system due to the intraventricular administration of a double-stranded agent of an embodiment having a complementary strand (second strand) of various lengths was conducted.

(Preparation of a Nucleic Acid Agent)

The target was the same BACE1 mRNA as in Example 1. The control (ASO) was also the same single-stranded LNA/DNA gapmer as in Example 1 (ASO (BACE1) 13mer in Table 5, FIG. 8(a)). By annealing the LNA/DNA gapmer (first strand) to the complementary strand (second strand), the following four kinds of double-stranded agent HDO were prepared.

Double-stranded agent (HDO 13mer, FIG. 8(b)): consists of the first strand and the second strand (cRNA (BACE1) 13mer), wherein the second strand comprises thirteen RNA nucleosides, and the internucleoside bonds of the second strand are, from the 5' end, two phosphorothioate bonds, eight phosphodiester bonds, and two phosphorothioate bonds.

Double-stranded agent (HDO 12mer, FIG. 8(c)): consists of the first strand and the second strand (cRNA (BACE1) 12mer) wherein the second strand comprises twelve RNA nucleosides, and the internucleoside bonds of the second strand are, from the 5' end, two phosphorothioate bonds, seven phosphodiester bonds, and two phosphorothioate bonds.

Double-stranded agent (HDO 11 mer, FIG. 8(d)): consists of the first strand and the second strand (cRNA (BACE1) 11 mer), wherein the second strand comprises eleven RNA nucleosides, and the internucleoside bonds of the second strand are, from the 5' end, two phosphorothioate bonds, six phosphodiester bonds, and two phosphorothioate bonds.

Double-stranded agent (HDO 10 mer, FIG. 8(e)): consists of the first strand and the second strand (cRNA (BACE1) 10 mer), wherein the second strand comprises ten RNA nucleosides, and the internucleoside bonds of the second strand are, from the 5' end, two phosphorothioate bonds, five phosphodiester bonds, and two phosphorothioate bonds.

Figure 8:
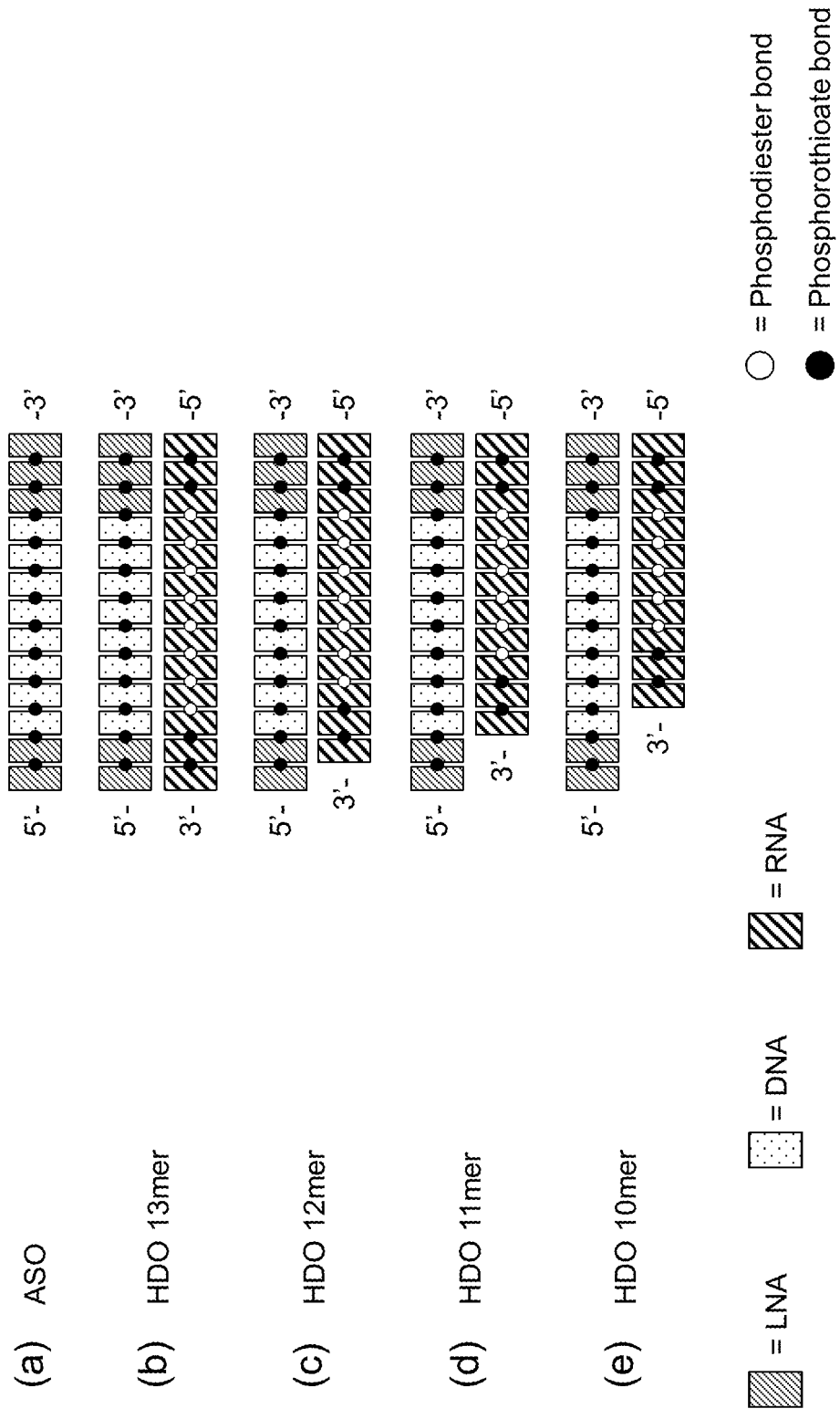
FIG. 8 shows schematic diagrams of the structures of the nucleic acids used in Example 2.

The sequences, chemical modifications and structures of the oligonucleotides used in Example 2 are shown in Table 5 and FIG. 8. The double-stranded agents were prepared in the same manner as in Example 1.

TABLE 5

Oligonucleotides used in Example 2

| Oligonucleotide name | Sequence (5'-3') | SEQ ID NO: |
|---|---|---|
| ASO (BACE1) 13mer | G(L)^T(L)^a^t^t^g^c^t^ g^a^G(L)^G(L)^A(L) | 12 |
| cRNA (BACE1) 13mer | U^C^CUCAGCAAU^A^C | 13 |
| cRNA (BACE1) 12mer | U^C^CUCAGCAA^U^A | 15 |
| cRNA (BACE1) 11mer | U^C^CUCAGCA^A^U | 16 |
| cRNA (BACE1) 10mer | U^C^CUCAGC^A^A | 17 |

Uppercase letter (L): LNA
Lowercase letter: DNA
Uppercase letter: RNA
^Phosphorothioate bond (Experiments In Vivo)

A nucleic acid agent was administered to mice at a dose of 12 μmol/mouse (n=4 to 5) into the left lateral ventricle. The mice used, the method of administration, and the analysis method of side effects were as described in Example 1.

(Results)

The results in Example 2 are shown in Tables 6 to 8.

TABLE 6

Acute tolerability score

|  | 1 hour | 3 hours | 6 hours |
|---|---|---|---|
| PBS | 0 ± 0 | 0 ± 0 | 0 ± 0 |
| ASO | 6.0 ± 0.8 | 5.0 ± 1.9 | 2.4 ± 2.9 |
| HDO 13mer | 2.3 ± 1.5 | 1.0 ± 0.8 | 0.5 ± 2.9 |
| HDO 12mer | 0.3 ± 0.5 | 0 ± 0 | 0 ± 0 |
| HDO 11mer | 0.3 ± 0.5 | 0 ± 0 | 0 ± 0 |
| HDO 10mer | 0.3 ± 0.5 | 0 ± 0 | 0 ± 0 |

(n = 4, mean value ± SD)

TABLE 7

Side-effect event rate (%)

|  | 1 hour | 3 hours | 6 hours |
|---|---|---|---|
| PBS | 0 | 0 | 0 |
| ASO | 100 | 100 | 50 |
| HDO 13mer | 75 | 75 | 75 |
| HDO 12mer | 25 | 0 | 0 |
| HDO 11mer | 25 | 0 | 0 |
| HDO 10mer | 0 | 0 | 0 |

TABLE 8

| | Number of deaths/number of doses |
|---|---|
| PBS | 0/4 |
| ASO | 1/5 |
| HDO 13mer | 0/4 |
| HDO 12mer | 0/4 |
| HDO 11mer | 0/4 |
| HDO 10mer | 0/4 |

With respect to the acute tolerability scores shown in Table 6, a rise was observed at 1 hour after the administration in the ASO administration group, which thereafter decreased gradually, however the rise remained up to 6 hours. On the other hand, in the groups of administration of four kinds of double-stranded agent HDO, the acute tolerability scores rose, but were lower than the ASO administration group.

The side-effect event rates shown in Table 7 also tended to be lower in the double-stranded agent HDO administration groups than in the ASO administration group.

As for the relationship between the number of administrations and number of deaths shown in Table 8, one out of five mice in the ASO administration group died, while none of the mice in the PBS administration group (negative control) and the four double-stranded agent HDO administration groups died.

These results indicate that the reduction of side effects in the double-stranded agent HDO is observed even when the complementary strand (second strand) is shorter than the antisense oligonucleotide (first strand).

Example 3

Experiments were conducted to confirm that the double-stranded agent HDO used in Examples 1 and 2 actually formed a double strand.

The single-stranded ASO and the double-stranded agents HDO used in Examples 1 and 2 were electrophoresed (100 V, 60 min) in a Tris-borate-EDTA buffer using a 15% acrylamide native gel. The gel was stained with GelRed (Wako Pure Chemical Industries, Ltd.), and detection was performed under UV light using a ChemiDoc Touch imaging system (Bio-Rad Laboratories, Inc.).

Figure 9:
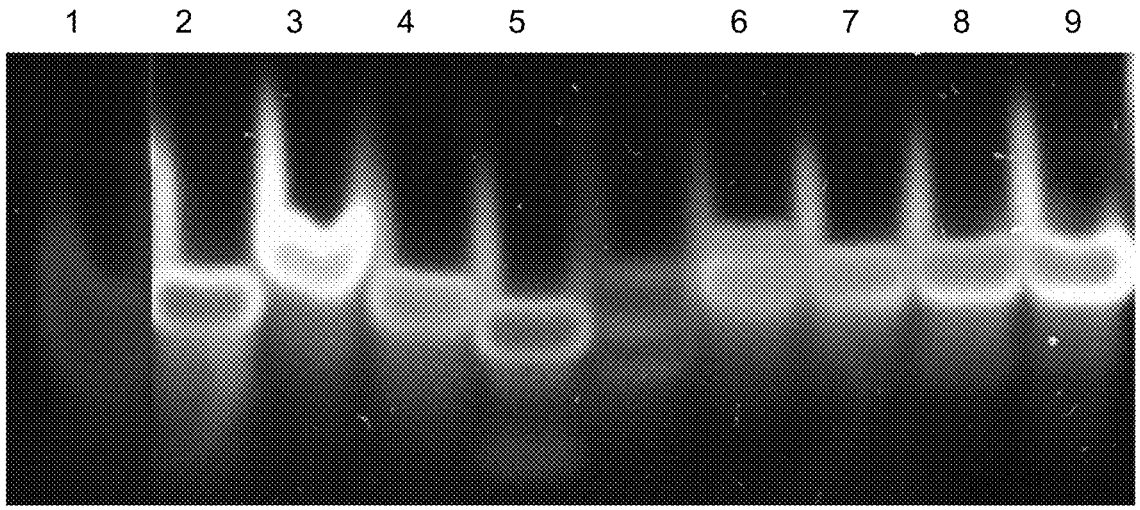
FIG. 9 is a photograph of the results of the experiment described in Example 3, in which it was confirmed that a nucleic acid complex formed a double strand.

The results of Example 3 are shown in FIG. 9. FIG. 9 shows the results of the single-stranded ASO (lane 1), HDO cRNA all PO (lane 2), HDO cRNA all PS (lane 3), HDO cDNA all PO (lane 4), HDO cDNA all PS (lane 5), HDO 10 mer (lane 6), HDO 11 mer (lane 7), HDO 12mer (lane 8), and HDO 13mer (lane 9). When a double strand is formed, staining (brightness) by a staining agent is increased. The brightness of HDO used in Examples 1 and 2 was increased compared to that of ASO, demonstrating that a double strand was actually formed.

Example 4

Experiments in vivo were conducted for examining a side effect in the central nervous system due to the intraventricular administration of a double-stranded agent of an embodiment having an overhanging region.
(Preparation of Nucleic Acid Agent)

The target was the same BACE1 mRNA as in Example 1. The control (ASO) was also the same single-stranded LNA/DNA gapmer as in Example 1 (ASO (BACE1) 13mer in Table 9, FIG. 10(a)). By annealing the LNA/DNA gapmer (first strand) to the second strand to prepare the following six kinds of double-stranded agents in the form of an overhanging-duplex oligonucleotide (hereinafter referred to as "Overhang" or "OH; see PCT/JP2017/035553).

Double-stranded agent (OH 26mer, FIG. 10(b)): consists of the first strand and the second strand (overhanging cRNA (BACE1) Gapmer 26mer), wherein the second strand consists of a region (13 base in length) complementary to the first strand and an overhanging region (13 base in length) located on its 5' end side, the overhanging region comprises, from the 5' end side, two LNA nucleosides, eight DNA nucleosides, and three LNA nucleosides, and all the internucleoside bonds in the overhanging region are phosphorothioate bonds.

Double-stranded agent (OH 26mer PS-4, FIG. 10(c)): consists of the first strand and the second strand (overhanging cRNA (BACE1) Gapmer 26mer PS-4), wherein the second strand is a strand, in which four phosphorothioate bonds other than the six phosphorothioate bonds from the 5' end and two phosphorothioate bonds from the 3' end are substituted with phosphodiester bonds, in the overhanging region of the above-described oligonucleotide overhanging cRNA (BACE1) Gapmer 26mer.

Double-stranded agent (OH 26mer PS-8, FIG. 10(d)): consists of the first strand and the second strand (overhanging cRNA (BACE1) Gapmer 26mer PS-8), wherein the second strand is a strand, in which eight phosphorothioate bonds other than the two phosphorothioate bonds from the 5' end and two phosphorothioate bonds from the 3' end are substituted with phosphodiester bonds, in the overhanging region of the above-described oligonucleotide overhanging cRNA (BACE1) Gapmer 26mer.

Double-stranded agent (OH 30mer, FIG. 10(e)): consists of the first strand and the second strand (overhanging cRNA (BACE1) Gapmer 30mer), wherein the second strand consists of a region (13 base in length) complementary to the first strand and an overhanging region (17 base in length) located on the 5' end side, the overhanging region comprises, from the 5' end, two LNA nucleosides, twelve DNA nucleosides, and three LNA nucleosides, and all the internucleoside bonds in the overhanging region are phosphorothioate bonds.

Double-stranded agent (OH 22mer, FIG. 10(f)): consists of the first strand and the second strand (overhanging cRNA (BACE1) Gapmer 22mer), wherein the second strand consists of a region (13 base in length) complementary to the first strand and an overhanging region (9 base in length) located on the 5' end side, the overhanging region comprises, from the 5' end, two LNA nucleosides, four DNA nucleosides, and three LNA nucleosides, and all the internucleoside bonds in the overhanging region are phosphorothioate bonds.

Double-stranded agent (OH 18mer, FIG. 10(g)): consists of the first strand and the second strand (overhanging cRNA (BACE1) Gapmer 18mer), wherein the second strand consists of a region (13 base in length) complementary to the first strand, and an overhanging region (5 base in length) located on the 5' end side, the overhanging region comprises five LNA nucleosides, and all the internucleoside bonds in the overhanging region are phosphorothioate bonds.

The sequences, chemical modifications and structures of the oligonucleotides used in Example 4 are shown in Table 9 and FIG. 10. The double-stranded agents were prepared in the same manner as in Example 1.

TABLE 9

Oligonucleotides used in Example 4

| Oligonucleotide name | Sequence (5'-3') | SEQ ID NO: |
|---|---|---|
| ASO (BACE1) 13mer | G(L)^T(L)^a^t^t^g^c^t^g^a^ G(L)^G(L)^A(L) | 12 |
| overhanging cRNA (BACE1)Gapmer 26mer | C(L)^T(L)^a^g^g^t^c^a^t^ g^C(L)^G(L)^T(L)UCCUCAG CAAU^A^C | 18 |
| overhanging cRNA (BACE1)Gapmer 26mer PS-4 | C(L)^T(L)^a^g^g^t^catg C(L)^G(L)^T(L)UCCUCAG CAAU^A^C | 18 |
| overhanging cRNA (BACE1)Gapmer 26mer PS-8 | C(L)^T(L)^aggtcatgC(L)^ G(L)^T(L)UCCUCAGCAAU^A^C | 18 |

TABLE 9-continued

Oligonucleotides used in Example 4

| Oligonucleotide name | Sequence (5'-3') | SEQ ID NO: |
|---|---|---|
| overhanging cRNA (BACE1)Gapmer 30mer | C(L)^T(L)^a^g^g^t^c^a^t^g^ t^t^t^t^C(L)^G(L)^T(L)UCCU CAGCAAU^A^C | 19 |
| overhanging cRNA (BACE1)Gapmer 22mer | C(L)^T(L)^a^g^g^t^C(L)^ G(L)^T(L)UCCUCAGCAAU^A^C | 20 |
| overhanging cRNA (BACE1)Gapmer 18mer | C(L)^T(L)^C(L)^G(L)^T(L) UCCUCAGCAAU^A^C | 21 |

Uppercase letter (L): LNA (C(L) represents 5-methylcytosine LNA.)
Lowercase letter: DNA
Uppercase letter: RNA
^Phosphorothioate bond (Experiments In Vivo)

A nucleic acid agent was administered to mice at a dose of 12 μmol/mouse (n=4 to 5) into the left lateral ventricle. The mice used, the method of administration, and the analysis method of side effects were as described in Example 1.

(Evaluation of Gene Inhibitory Effect)

Seven days after the injection, the mice were perfused with PBS, and then the mouse was dissected and the left hippocampus was isolated. RNA was extracted using the Isogen I kit (GeneDesign Inc.) according to the protocol. The cDNA was synthesized using the Transcriptor Universal cDNA Master, DNase (Roche Diagnostics) according to the protocol. A quantitative RT-PCR was performed with TaqMan (Roche Applied Science). The primers used in the quantitative RT-PCR were the products designed and produced by Thermo Fisher Scientific (formerly Life Technologies Corp.) according to various gene numbers. The amplification conditions (temperature and time) were as follows: 95° C. for 15 sec, 60° C. for 30 sec, and 72° C. for 1 sec (1 cycle), which was repeated for 40 cycles. Based on the results of the quantitative RT-PCR thus obtained, the expression amount of BACE1/the expression amount of ACTB (internal standard gene) was calculated respectively.

(Results)

Figure 11:
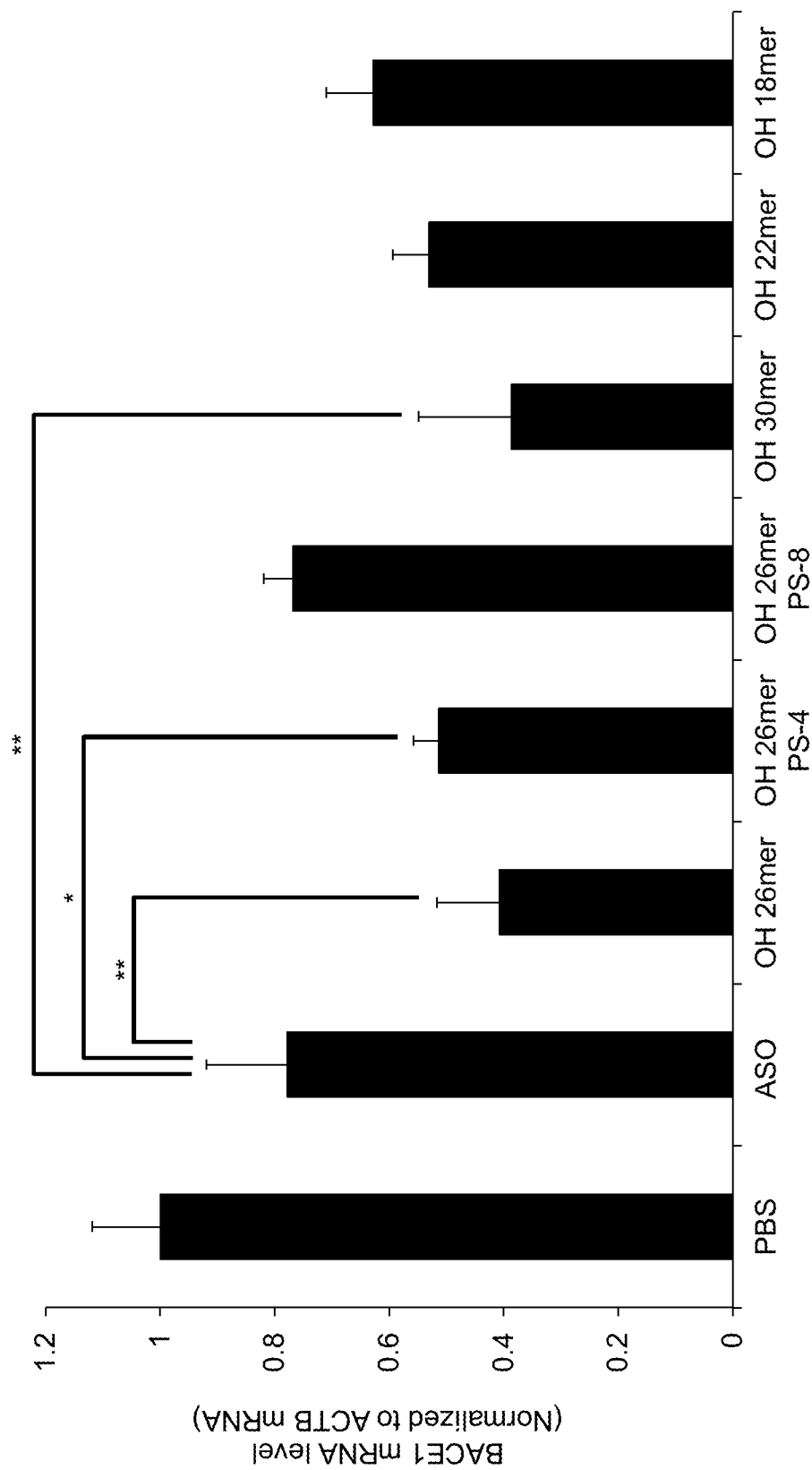
FIG. 11 is a graph showing the results of the experiments described in Example 4, comparing the expression inhibitory effects on the target gene (BACE1) by nucleic acid complexes. The "**" indicates $p<0.01$. The "*" indicates $p<0.05$.

The results in Example 4 are shown in Tables 10 to 12 and FIG. 11.

TABLE 10

Acute tolerability score

| | 1 hour | 3 hours | 6 hours |
|---|---|---|---|
| PBS | 0 ± 0 | 0 ± 0 | 0 ± 0 |
| ASO | 7.5 ± 0.9 | 5.5 ± 0.9 | 0.5 ± 2.3 |
| OH 26mer | 0 ± 0 | 0 ± 0 | 0 ± 0 |
| OH 26mer PS-4 | 0 ± 0 | 0 ± 0 | 0 ± 0 |
| OH 26mer PS-8 | 0 ± 0 | 0 ± 0 | 0 ± 0 |
| OH 30mer | 0 ± 0 | 0 ± 0 | 0 ± 0 |
| OH 22mer | 0 ± 0 | 0 ± 0 | 0 ± 0 |
| OH 18mer | 0 ± 0 | 0 ± 0 | 0 ± 0 |

(n = 4-5, mean value ± SD)

TABLE 11

Side-effect event rate (%)

| | 1 hour | 3 hours | 6 hours |
|---|---|---|---|
| PBS | 0 | 0 | 0 |
| ASO | 100 | 100 | 50 |
| OH 26mer | 0 | 0 | 0 |
| OH 26mer PS-4 | 0 | 0 | 0 |
| OH 26mer PS-8 | 0 | 0 | 0 |
| OH 30mer | 0 | 0 | 0 |
| OH 22mer | 0 | 0 | 0 |
| OH 18mer | 0 | 0 | 0 |

TABLE 12

| | Number of deaths/number of doses |
|---|---|
| PBS | 0/4 |
| ASO | 2/6 |
| OH 26mer | 0/4 |
| OH 26mer PS-4 | 0/4 |
| OH 26mer PS-8 | 0/4 |
| OH 30mer | 0/4 |
| OH 22mer | 0/4 |
| OH 18mer | 0/4 |

With respect to the acute tolerability scores shown in Table 10, rise at 1 hour after the administration was observed in the ASO administration group, which was thereafter reduced gradually, however the rise remained up to 6 hours. Meanwhile, in any of the PBS administration group (negative control) and the groups of administration of six kinds of double-stranded agent, the acute tolerability scores did not increase.

With respect to the side-effect event rates shown in Table 11, in many mice in the ASO administration group side effects were observed, however in any of the mice in the PBS administration group (negative control), and the groups of administration of six kinds of double-stranded agent, side-effect was not observed.

As for the relationship between the number of administrations and the number of deaths shown in Table 12 shows that two out of six mice in the ASO administration group died, while none of the mice in the PBS administration group (negative control) and the groups of administration of six kinds of double-stranded agent died.

Further, all the double-stranded agents having an overhanging region tended to exhibit a higher target gene (BACE1) inhibitory effect than ASO (FIG. 11). In particular, as the strand length of the overhanging region increases, the gene inhibitory effect tends to become higher, and as the number of the phosphorothioate bond increases, the gene inhibitory effect also tends to become higher. These trends are consistent with a previous patent application (PCT/JP2017/035553).

These results demonstrate that a double-stranded agent having an overhanging region improves side effects in the central nervous system, and enhances a gene inhibitory effect compared to a single-stranded agent ASO.

Example 5

Experiments in vivo were conducted for examining side effects in the central nervous system due to intraventricular administration of a double-stranded agent of an embodiment targeting a gene different from that in Example 1.

(Preparation of Nucleic Acid Agent)

The single-stranded ASO to be used as a control was a 16mer LNA/DNA gapmer comprising three LNA nucleosides from the 5' end, and three LNA nucleosides from the 3' end and ten DNA nucleosides between them (ASO (Tau) 16mer in Table 13, FIG. 12(a)). This LNA/DNA gapmer is complementary to positions 3339 to 3354 of the murine microtubule-associated protein tau (Tau) mRNA (SEQ ID NO: 3). By annealing the LNA/DNA gapmer (first strand) to the second strand, the following double-stranded agent HDO, and OH (Overhang) were prepared.

Double stranded agent HDO (FIG. 12(b)): consists of the first strand and the second strand (HDO cRNA (Tau) 16mer), wherein the second strand comprises sixteen RNA nucleosides, and the internucleoside bonds in the second strand are, from the 5' end, two phosphorothioate bonds, eleven phosphodiester bonds, and two phosphorothioate bonds.

Double stranded agent OH (FIG. 12(c)): consists of the first strand and the second strand (overhanging cRNA (Tau) DNA 29mer), wherein the second strand consists of a region (16 base in length) complementary to the first strand, and an overhanging region (13 base in length) on its 5' end side, and the overhanging region comprises thirteen DNA nucleosides, while all of the internucleoside bonds in the overhanging region are phosphorothioate bonds.

Figure 12:
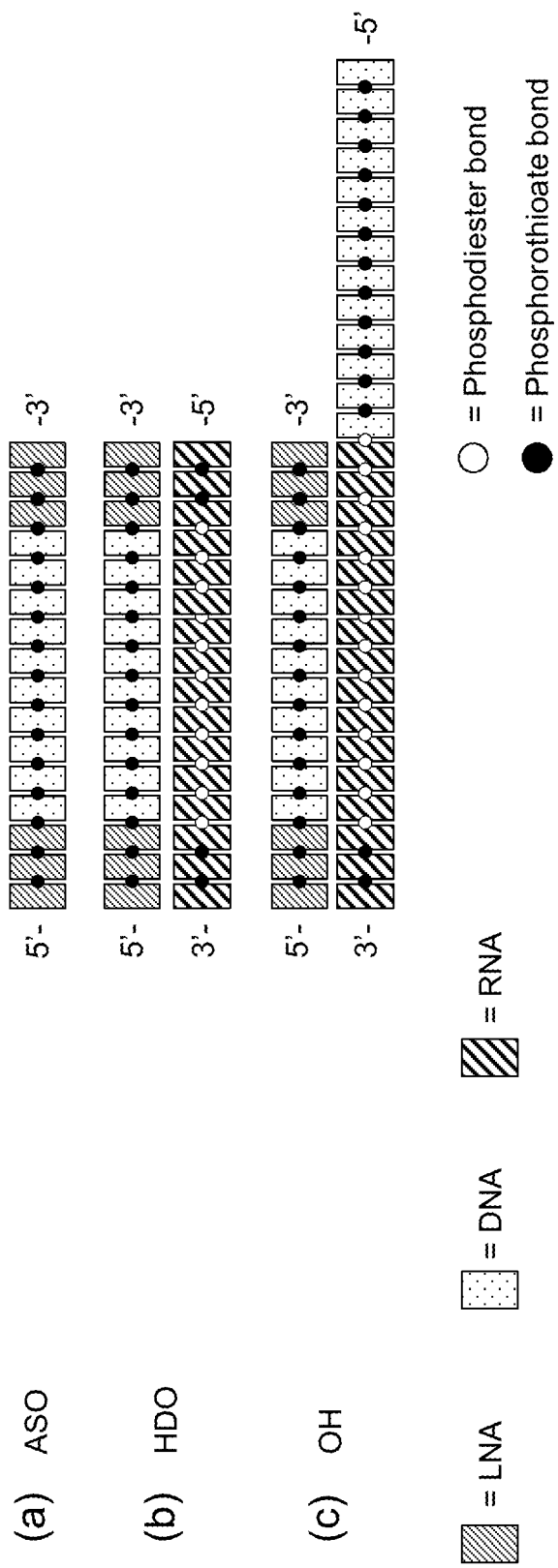
FIG. 12 shows schematic diagrams of the structures of the nucleic acids used in Example 5.

The sequences, chemical modifications and structures of the oligonucleotides used in Example 5 are shown in Table 13 and FIG. 12. The double-stranded agents were prepared in the same manner as in Example 1.

TABLE 13

Oligonucleotides used in Example 5

| Oligonucleotide name | Sequence (5'-3') | SEQ ID NO: |
|---|---|---|
| ASO (Tau) 16mer | A(L)^T(L)^A(L)^g^t^c^a^c^t^c^t^g^g^T(L)^G(L)^A(L) | 22 |
| HDO cRNA (Tau) 16mer | U^C^ACCAGAGUGACU^A^U | 23 |
| overhanging cRNA (Tau) DNA 29mer | g^t^a^g^g^t^c^a^t^g^c^g^tUCACCAGAGUGACU^A^U | 24 |

Uppercase letter (L): LNA
Lowercase letter: DNA
Uppercase letter: RNA
^Phosphorothioate bond (Experiments In Vivo)

A nucleic acid agent was administered to mice at a dose of 6 μmol/mouse (n=4) into the left lateral ventricle. The mice used, the method of administration, and the analysis method of side effects were as described in Example 1.

(Results)

The results of Example 5 are shown in Tables 14 to 16.

TABLE 14

| | Acute tolerability score | | |
|---|---|---|---|
| | 1 hour | 3 hours | 6 hours |
| PBS | 0 ± 0 | 0 ± 0 | 0 ± 0 |
| ASO | 3.5 ± 1.0 | 1.5 ± 1.7 | 0 ± 0 |
| HDO | 0 ± 0 | 0 ± 0 | 0 ± 0 |
| OH | 0 ± 0 | 0 ± 0 | 0 ± 0 |

(n = 3-4, mean value ± SD)

TABLE 15

| | Side-effect event rate (%) | | |
|---|---|---|---|
| | 1 hour | 3 hours | 6 hours |
| PBS | 0 | 0 | 0 |
| ASO | 100 | 50 | 0 |
| HDO | 0 | 0 | 0 |
| OH | 0 | 0 | 0 |

TABLE 16

| | Number of deaths/number of doses |
|---|---|
| PBS | 0/4 |
| ASO | 1/4 |
| HDO | 0/4 |
| OH | 0/4 |

With respect to the acute tolerability scores shown in Table 14, rise at 1 hour after the administration was observed in the ASO administration group, which was thereafter decreased gradually, and improved after 6 hours. Meanwhile, in any of the PBS-administered group (negative control) and the groups of administration of two kinds of double-stranded agent (HDO and OH), the acute tolerability scores did not rise.

With respect to the side-effect event rates shown in Table 15, side effects were observed in many mice in the ASO administration group, however side-effects were not observed in any mice of the PBS administration group (negative control) and the groups of administration of two kinds of double-stranded agent.

As for the relationship between the number of administrations and the number of deaths shown in Table 16, one out of four mice in the ASO administration group died, while none of the mice in the PBS administration group (negative control) and the groups of administration of two kinds of double-stranded agent died.

These results indicate that the side effect improving effect in the central nervous system by a double-stranded agent is not dependent on a target gene, and is applicable to a variety of target genes.

Example 6

Experiments in vivo were conducted for examining side effects in the central nervous system due to intraventricular administration of a double-stranded agent of an embodiment different from those in Examples 1 to 5.

(Preparation of Nucleic Acid Agent)

The target was the same BACE1 mRNA as in Example 1. The control (ASO) was also the same single-stranded LNA/DNA gapmer as in Example 1 (ASO (BACE1) 13mer in Table 17, FIG. 13(a)). By annealing the LNA/DNA gapmer (first strand) to the second strand, a double-stranded agent in the form of OH (Overhang) was prepared. In addition, a double-stranded agent in the form of a hetero-chimera-duplex oligonucleotide having a double-stranded nucleic acid structure of 13 base in length on the 3' end side of the LNA/DNA gapmer (hereinafter referred to as "HCDO"; see International Publication No. WO 2014/192310) was also prepared. The double-stranded agent in the form of OH, and the double-stranded agent in the form of HCDO used in this Example will be described below.

Double stranded agent OH (FIG. 13(b)): consists of the first strand (ASO (BACE1) 13mer) and the second strand (over cRNA (BACE1) OAT3-2 G 26mer), wherein the second strand consists of a region (13 base in length) complementary to the first strand, and an overhanging region (13 base in length) on the 5' end side, while the complementary region comprises two 2'-O-methylated RNA nucleosides from the 3' end, the overhanging region comprises, from the 5' end, two LNA nucleosides, eight DNA nucleosides, and three LNA nucleosides, and all of the internucleoside bonds in the overhanging region are phosphorothioate bonds.

Double stranded agent HCDO (FIG. 13(c)): consists of the first strand (HCDO cRNA (OAT3 1-2) 26mer), and the second strand (OAT3-2 G 13mer). This HCDO has a double-stranded nucleic acid structure of 13 base in length on the 3' end side of the antisense oligo region (indicated by † in FIG. 13(c)) complementary to BACE1 mRNA.

Figure 13:
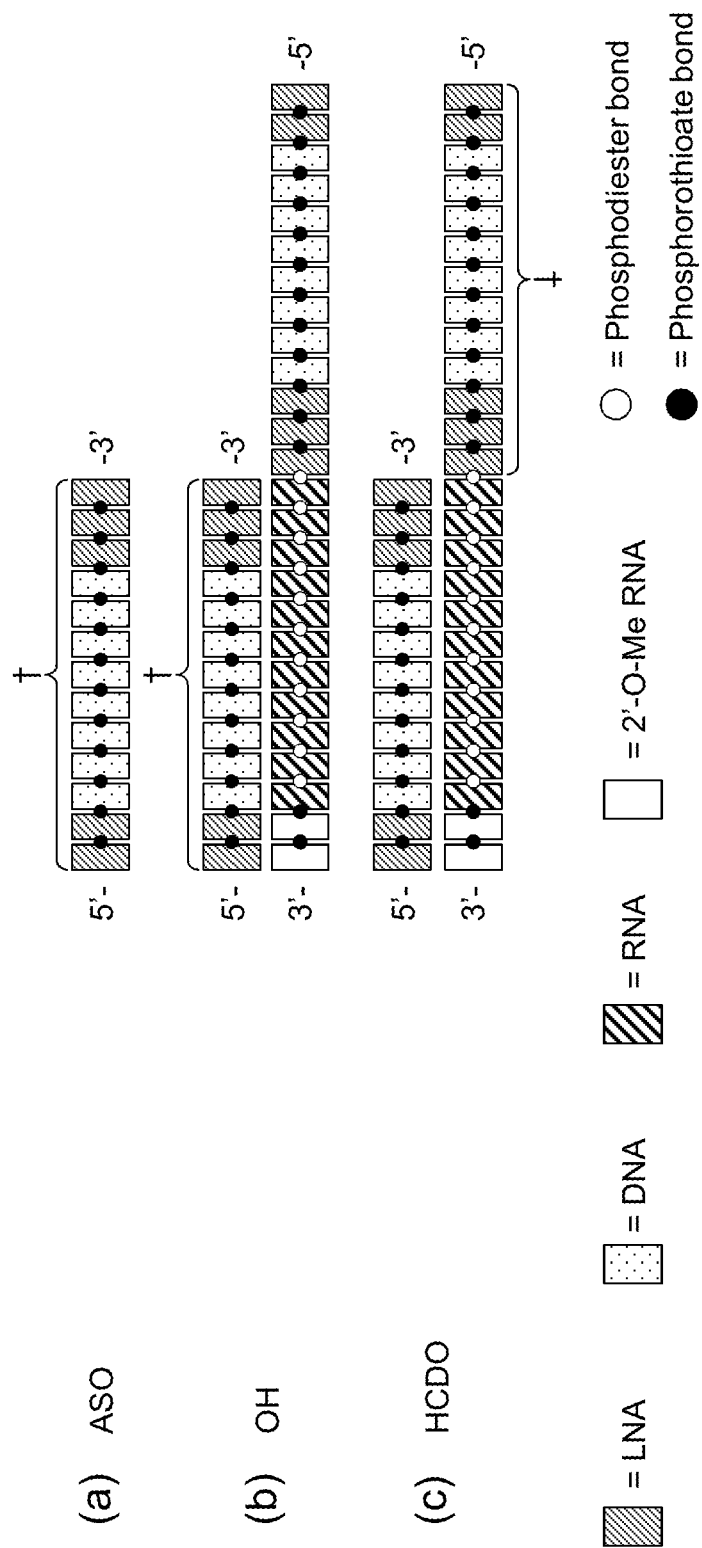
FIG. 13 shows schematic diagrams of the structures of the nucleic acids used in Example 6. The "†" indicates an antisense oligonucleotide region.

The sequences, chemical modifications and structures of the oligonucleotides used in Example 6 are shown in Table 17 and FIG. 13. The double-stranded agents were prepared in the same manner as in Example 1.

TABLE 17

Oligonucleotides used in Example 6

| Oligonucleotide name | Sequence (5'-3') | SEQ ID NO: |
|---|---|---|
| ASO (BACE1) 13mer | G(L)^T(L)^a^t^t^g^c^t^g^a^ G(L)^G(L)^A(L) | 12 |
| over cRNA (BACE1) OAT3-2 G 26mer | G(L)^T(L)^a^g^g^t^c^a^t^g^ C(L)^G(L)^T(L)UCCUCAGCAAU^ A(M)^C(M) | 25 |
| OAT3-2 G 13mer | C(L)^T(L)^a^g^g^t^c^a^t^g^ C(L)^G(L)^T(L) | 26 |
| HCDO cRNA(OAT3 1-2) 26mer | G(L)^T(L)^a^t^t^g^c^t^g^a^ G(L)^G(L)^A(L)ACGCAUGACCU^ A(M)^G(M) | 27 |

Uppercase letter (L): LNA (C(L) represents 5-methylcytosine LNA.)
Lowercase letter: DNA
Uppercase letter: RNA
Uppercase letter (M): 2'-O-Me RNA
^Phosphorothioate bond (Experiments In Vivo)
A nucleic acid agent was administered to mice at a dose of 12 µmol/mouse (n=4 to 11) into the left lateral ventricle. As a side effect, the number of mice that died within one day after the administration was recorded. The mice used, the method of administration, and the analysis method of side effects were as described in Example 1.
(Results)
The results of Example 6 are shown in Table 18.

TABLE 18

| | Number of deaths/number of doses |
|---|---|
| PBS | 0/4 |
| ASO | 6/11 |
| OH | 0/5 |
| HCDO | 0/5 |

Six out of the 11 mice in the ASO administration group died, however none of the mice in the PBS administration group (negative control) and the groups of administration of two kinds of double-stranded agent (OH and HCDO) died (Table 18). These results indicated that a double-stranded agent having an overhanging region, and a double-stranded agent having a double-stranded nucleic acid structure bound to the 3' end side of the antisense oligo region were able to improve the side effects compared to a single-stranded agent ASO.

Example 7

Experiments in vivo were conducted for examining side effects in the central nervous system due to intrathecal administration of a double-stranded nucleic acid agent of an embodiment.
(Preparation of Nucleic Acid Agent)
The single-stranded ASO to be used as a control was a 16mer LNA/DNA gapmer comprising three LNA nucleosides from the 5' end, and three LNA nucleosides from the 3' end, and 10 DNA nucleosides between them (ASO (MALAT) 16mer in Table 19, FIG. 14(a)). This LNA/DNA gapmer is complementary to positions 1316 to 1331 of the murine metastasis associated lung adenocarcinoma transcript 1 (MALAT1) non-coding RNA (SEQ ID NO: 5). By annealing the LNA/DNA gapmer (first strand) to a tocopherol-bound second strand (Tocopherol-cRNA (MALAT) 16mer), the double-stranded agent HDO (FIG. 14(b)) was prepared. This second strand comprises, from the 5' end, three 2'-O-methylated RNA nucleosides, ten RNA nucleosides, and three 2'-O-methylated RNA nucleosides, and the internucleoside bonds in the second strand comprise, from the 5' end, three phosphorothioate bonds, nine phosphodiester bonds, and three phosphorothioate bonds.

Figure 14:
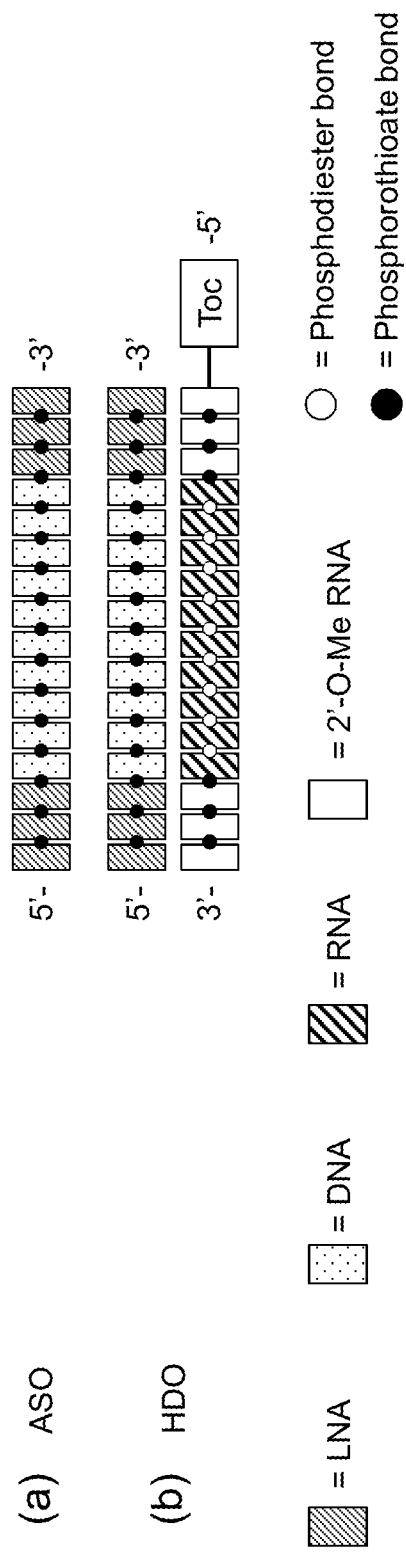
FIG. 14 shows schematic diagrams of the structures of the nucleic acids used in Examples 7 and 8. The "Toc" indicates tocopherol.

The sequences, chemical modifications and structures of the oligonucleotides used in Example 7 are shown in Table 19 and FIG. 14. The double-stranded agents were prepared in the same manner as in Example 1.

TABLE 19

Oligonucleotides used in Example 7

| Oligonucleotide name | Sequence (5'-3') | SEQ ID NO: |
|---|---|---|
| ASO(MALAT) 16mer | C(L)^T(L)^A(L)^g^t^t^c^a^c^ t^g^a^a^T(L)^G(L)^C(L) | 28 |
| Tocopherol-cRNA (MALAT) 16mer | Toc-G(M)^C(M)^A(M)^UUCAGUG AAC^U(M)^A(M)^G(M) | 29 |

Uppercase letter (L): LNA (C(L) represents 5-methylcytosine LNA.)
Lowercase letter: DNA
Uppercase letter: RNA
Uppercase letter (M): 2'-O-Me RNA
^Phosphorothioate bond
Toc: Tocopherol (Experiments In Vivo)
A nucleic acid agent was administered to mice intrathecally in the lumbar region at a dose of 4 mg/kg (n=4 to 9). As a side effect, the number of mice that died within one day after the administration was recorded. The mice used, and the analysis method of side effects were as described in Example 1.
(Results)
The results of Example 7 are shown in Table 20.

TABLE 20

| | Number of deaths/number of doses |
|---|---|
| PBS | 0/4 |
| ASO | 4/9 |
| HDO | 0/5 |

Four out of nine mice in the ASO administration group died, however none of the mice in the PBS administration group (negative control) and the group of administration of tocopherol-bound double-stranded agent HDO died (Table 20). These results indicated that a tocopherol-bound double-stranded agent HDO administered intrathecally was able to improve the side effects compared to a single-stranded agent ASO.

Example 8

Experiments in vivo were conducted for examining side effects of intravenous administration of the double-stranded nucleic acid agent of an embodiment in a primate.
(Preparation of Nucleic Acid Agent)

The single-stranded ASO to be used as a control was a 16mer LNA/DNA gapmer comprising three LNA nucleosides from the 5' end, and three LNA nucleosides from the 3' end and ten DNA nucleosides between them (ASO (mfMALAT1) in Table 21, FIG. 14(a)). This LNA/DNA gapmer targets the MALAT1 non-coding RNA of the cynomolgus monkey. The base sequence of the LNA/DNA gapmer was designed referring to Hung G, et al., (Characterization of Target mRNA Reduction Through In Situ RNA Hybridization in Multiple Organ Systems Following Systemic Antisense Treatment in Animals, Nucleic Acid Therapeutics, 23(6): 369-378 (2013)). By annealing this LNA/DNA gapmer (first strand) to a tocopherol-bound second strand (Tocopherol-cRNA (mfMALAT1)), the double-stranded agent HDO (FIG. 14(b)) was prepared. This second strand comprises three 2'-O-methylated RNA nucleosides, ten RNA nucleosides, and three 2'-O-methylated RNA nucleosides from the 5' end. The double-stranded agent was prepared in the same manner as in Example 1.

The sequences, chemical modifications, and structures of the oligonucleotides used in Example 8 are shown in Table 21 and FIG. 14.

TABLE 21

Oligonucleotides used in Example 8

| Oligonucleotide name | Sequence (5'-3') | SEQ ID NO: |
|---|---|---|
| ASO(mfMALAT1) | A(L)^G(L)^T(L)^a^c^t^a^t^ a^g^c^a^t^C(L)^T(L)^G(L) | 30 |
| Tocopherol-cRNA(mfMALAT1) | Toc-C(M)^A(M)^G(M)^AUGCUA UAGU^A(M)^C(M)^U(M) | 31 |

Uppercase letter (L): LNA (C(L) represents 5-methylcytosine LNA.)
Lowercase letter: DNA
Uppercase letter: RNA
Uppercase letter (M): 2'-O-Me RNA
^Phosphorothioate bond
Toc: Tocopherol (Experiments In Vivo)

The cynomolgus monkey was a male with a weight of 1.8 kg. All experiments were conducted with n=1. Each nucleic acid agent was injected intravenously into the cynomolgus monkey at a dose of 50 mg/kg through the saphenous vein. In addition, a cynomolgus monkey injected solely with PBS or the first strand (ASO) was produced as a negative control group.

On day 3 after the intravenous administration, BUN (blood urea nitrogen), and a creatinine level (Cre) were measured by a serologic biochemical test. When these values are higher, the renal function is indicated to be lowered.

(Results)

After intravenous administration, frequent vomiting was seen in an ASO administered individual, while vomiting was not seen in an HDO administered individual.

The results of the evaluation of renal function by a serologic biochemical test on day 3 after the intravenous administration are shown in Table 22.

TABLE 22

| | BUN (mg/dl) | | Cre (mg/dl) | |
|---|---|---|---|---|
| | Before administration | After administration | Before administration | After administration |
| PBS | 15.5 | 20.2 | 0.5 | 0.5 |
| ASO | 18.9 | 178.8 | 0.5 | 8.5 |
| HDO | 20.6 | 23.3 | 0.5 | 0.6 |

As shown in Table 22 in an ASO-administered individual, the blood urea nitrogen (BUN) and the creatinine level (Cre) were increased after the administration compared to those before the administration. On the other hand, in an HDO-administered individual, neither blood urea nitrogen (BUN) nor creatinine (Cre) showed clear increase after the administration.

These results indicated that a double-stranded HDO was able to avoid vomiting and decrease in the renal function which were seen with a single-stranded ASO.

Example 9

Experiments in vivo were conducted for examining side effects of intravenous administration or subcutaneous administration of a double-stranded nucleic acid agent of an embodiment.
(Preparation of Nucleic Acid Agent)

The single-stranded ASO to be used as a control was a 13mer LNA/DNA mixmer in which one DNA nucleoside and one LNA nucleoside are repeated alternately (ASO (dystrophin) 13mer in Table 23, FIG. 15 (a))). This LNA/DNA mixmer targets a murine dystrophin mRNA. By annealing this LNA/DNA mixmer (first strand) to a tocopherol-bound second strand (tocopherol-cRNA (dystrophin) 13mer), the double-stranded agent HDO (FIG. 15(b)) was prepared. This second strand comprises, from the 5' end, three 2'-O-methylated RNA nucleosides, seven RNA nucleosides, and three 2'-O-methylated RNA nucleosides. The double-stranded agent was prepared in the same manner as in Example 1.

The sequences, chemical modifications, and structures of the oligonucleotides used in Example 9 are shown in Table 23 and FIG. 15.

TABLE 23

Oligonucleotides used in Example 9

| Oligonucleotide name | Sequence (5'-3') | SEQ ID NO: |
|---|---|---|
| ASO (dystrophin) 13mer | a^A(L)^c^C(L)^t^C(L)^g^ G(L)^c^T(L)^t^A(L)^c | 32 |

TABLE 23-continued

Oligonucleotides used in Example 9

| Oligonucleotide name | Sequence (5'-3') | SEQ ID NO: |
|---|---|---|
| Tocopherol-cRNA (dystrophin) 13mer | Toc-G(M)^U(M)^A(M)^AGCCGAG^G(M)^U(M)^U(M) | 33 |

Uppercase letter (L): LNA (C(L) represents 5-methylcytosine LNA.)
Lowercase letter: DNA
Uppercase letter: RNA
Uppercase letter (M): 2'-O-Me RNA
^Phosphorothioate bond
Toc: Tocopherol (Experiments In Vivo)
ASO was administered to mice intravenously at a dose of 100 mg/kg, or administered subcutaneously at a dose of 25, 50, or 100 mg/kg. Further, HDO was administered to mice intravenously, or subcutaneously at a dose of 100 mg/kg. They were observed for any change of conditions during 2 weeks after the administration.
(Results)
The results in Example 9 are shown in Table 24.

TABLE 24

| Nucleic acid | Administration method | Dose | Changes after administration |
|---|---|---|---|
| ASO | iv | 100 mg/kg | Responsiveness gradually decreased in less than 10 min after administration. Occasionally generalized convulsion. Died in about 30 min. |
| ASO | sc | 100 mg/kg | Same as above |
| ASO | sc | 50 mg/kg | Same as above |
| ASO | sc | 25 mg/kg | No hypoactivity, no convulsion, no death. |
| HDO | iv | 100 mg/kg | No hyporesponsiveness, no convulsion, no death. |
| HDO | sc | 100 mg/kg | No hyporesponsiveness, no convulsion, no death. |

As shown in Table 24, in an individual who received ASO intravenously (iv) at a dose of 100 mg/kg, or an individual who received it subcutaneously (sc) at a dose of 50 or 100 mg/kg, hyporesponsiveness and convulsion occurred in 10 min or less, and these individuals died after about 30 min. On the other hand, in the individual who received HDO intravenously (iv) at a dose of 100 mg/kg, and the individual who received it subcutaneously (sc) at a dose of 100 mg/kg, neither hyporesponsiveness nor death was observed for 2 weeks after the administration.

These results indicated that a double-stranded HDO avoided acute toxicity at the time of systemic administration (such as intravenous administration, or subcutaneous administration) which is seen with a single-stranded ASO.

All publications, patents, and patent applications cited herein are hereby incorporated by reference directly herein.

The invention claimed is:

1. A method for modulating expression of a target transcriptional product in the central nervous system of a subject, comprising injecting a low toxicity composition to a central nervous system intrathecally or intraventricularly, wherein the composition comprises a nucleic acid complex formed by annealing together a first nucleic acid strand comprising an antisense oligonucleotide region with respect to the target transcriptional product, and a second nucleic acid strand comprising a complementary region that is complementary to at least part of the first nucleic acid strand, and:
   wherein the antisense oligonucleotide region is a gapmer type antisense oligonucleotide region of 12 to 26 bases in length, and the second nucleic acid strand is not bound to a lipid, or
   wherein the antisense oligonucleotide region is a mixmer type antisense oligonucleotide region of 12 to 26 bases in length.

2. The method according to claim 1, wherein the toxicity is neurotoxicity.

3. The method according to claim 2, wherein the neurotoxicity produces a symptom selected from the group consisting of death, breathing abnormality, cardiovascular abnormality, headache, nausea or vomiting, unresponsiveness or low responsiveness, impaired consciousness, mental disorder, personality change, hallucination, delusion, cognitive dysfunction, abnormal posture, involuntary movement, tremor, convulsion, hyperactivity, disturbance of motor function, paralysis, sensory abnormality, and autonomic nervous system dysfunction.

4. The method according to claim 1, wherein said antisense oligonucleotide region in the first nucleic acid strand is 12-16 bases in length.

5. The method according to claim 1, wherein the second nucleic acid strand is 9 to 50 bases in length.

6. The method according to claim 1, wherein said complementary region in the second nucleic acid strand is complementary to at least part of said antisense oligonucleotide region in the first nucleic acid strand.

7. The method according to claim 1, wherein the first nucleic acid strand is a nucleic acid strand comprising:
   (a) at least four contiguous DNA nucleotides or modified DNA nucleotides recognized by RNase H when hybridized to said transcriptional product, and further comprising:
   (b) a 5' wing region comprising one or multiple modified nucleotides placed on the 5' end side of said at least four contiguous DNA nucleotides or modified DNA nucleotides recognized by RNase H; and/or (c) a 3' wing region comprising one or multiple modified nucleotides placed on the 3' end side of said at least four contiguous DNA nucleotides or modified DNA nucleotides recognized by RNase H.

8. The method according to claim 1, wherein the second nucleic acid strand is a nucleic acid strand comprising:
(a) at least four contiguous RNA nucleosides, and further comprising:
(b) one or multiple modified nucleotides placed on the 5' end side of said at least four contiguous RNA nucleosides, and/or
(c) one or multiple modified nucleotides placed on the 3' end side of said at least four contiguous RNA nucleosides.

9. The method according to claim 1, wherein the second nucleic acid strand further comprises at least one overhanging region located on one or both of the 5' end side and the 3' end side of said complementary region.

10. The method according to claim 9, wherein the overhanging region in the second nucleic acid strand is at least 5 bases in length.

11. The method according to claim 1, wherein:
the first nucleic acid strand further comprises a complementary RNA region, and said complementary RNA region has at least two contiguous RNA nucleotides that can be recognized by RNase H when the first nucleic acid strand is hybridized with the second nucleic acid strand,
said complementary region in the second nucleic acid strand is a complementary DNA region, and said complementary DNA region can hybridize with the complementary RNA region in the first nucleic acid strand to promote the recognition of at least two contiguous RNA nucleotides in the first nucleic acid strand by RNase H, and further
said antisense oligonucleotide region in the first nucleic acid strand cannot hybridize with the second nucleic acid strand.

12. The method according to claim 1, wherein the expression modulation of the target transcriptional product is reduction of the amount of the target transcriptional product.

13. The method according to claim 1, for treating a central nervous system disease.

14. The method according to claim 1, wherein the antisense oligonucleotide region comprises an LNA nucleoside.

15. The method according to claim 1, wherein the low toxicity composition exhibits a reduced toxicity when injected into the subject, relative to the toxicity of a single-stranded antisense oligonucleotide that is administered to the subject.

* * * * *